US008431349B2

(12) United States Patent
Mathialagan et al.

(10) Patent No.: US 8,431,349 B2
(45) Date of Patent: Apr. 30, 2013

(54) COMPOSITIONS AND METHODS FOR EARLY PREGNANCY DIAGNOSIS

(75) Inventors: Nagappan Mathialagan, Ballwin, MO (US); Robert M. Roberts, Columbia, MO (US); Michael F. McGrath, Clearwater, FL (US); Jonathan Green, Columbia, MO (US)

(73) Assignees: Monsanto Technology LLC, St. Louis, MO (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 12/747,514

(22) PCT Filed: Dec. 12, 2008

(86) PCT No.: PCT/US2008/086674
§ 371 (c)(1),
(2), (4) Date: Oct. 20, 2010

(87) PCT Pub. No.: WO2009/076632
PCT Pub. Date: Jun. 18, 2009

(65) Prior Publication Data
US 2011/0076705 A1 Mar. 31, 2011

Related U.S. Application Data

(60) Provisional application No. 61/013,603, filed on Dec. 13, 2007.

(51) Int. Cl.
*G01N 33/53* (2006.01)
*C12N 5/20* (2006.01)
*C07K 16/42* (2006.01)
*C07K 16/24* (2006.01)

(52) U.S. Cl.
USPC ......... 435/7.1; 435/326; 435/810; 530/387.1; 530/387.3; 530/388.23

(58) Field of Classification Search .................. None
See application file for complete search history.

(56) References Cited

U.S. PATENT DOCUMENTS

| | | | |
|---|---|---|---|
| 4,208,479 A | 6/1980 | Zuk et al. | 435/7 |
| 4,271,140 A | 6/1981 | Bunting | 436/500 |
| 4,755,460 A | 7/1988 | Bostwick et al. | 435/7 |
| 4,895,804 A | 1/1990 | Bostwick et al. | 435/240.27 |
| 5,859,205 A * | 1/1999 | Adair et al. | 530/387.3 |
| 6,787,324 B2 | 9/2004 | Jordan et al. | 436/518 |
| 6,869,770 B1 | 3/2005 | Roberts et al. | 435/7.1 |
| 7,241,873 B2 * | 7/2007 | Uede et al. | 530/387.3 |
| 7,393,696 B2 | 7/2008 | Roth et al. | 436/510 |
| 7,575,861 B2 | 8/2009 | Lucy et al. | 435/7.1 |
| 7,687,281 B2 | 3/2010 | Roth et al. | 436/510 |
| 7,763,432 B2 | 7/2010 | Roberts et al. | 435/7.1 |
| 2001/0024799 A1 | 9/2001 | Jordan et al. | 435/7.9 |
| 2003/0073248 A1 | 4/2003 | Roth et al. | 436/510 |
| 2005/0100975 A1 | 5/2005 | Roberts et al. | 435/7.92 |
| 2006/0199235 A1 | 9/2006 | Lucy et al. | 435/7.1 |
| 2007/0166773 A1 | 7/2007 | Roberts et al. | 530/387.1 |
| 2007/0184558 A1 | 8/2007 | Roth et al. | 436/510 |
| 2009/0258375 A1 | 10/2009 | Green et al. | 435/23 |

FOREIGN PATENT DOCUMENTS

| | | |
|---|---|---|
| WO | WO 99/06038 | 2/1999 |
| WO | WO 99/47934 | 9/1999 |

OTHER PUBLICATIONS

Ackermann, M et al. Influence of cell- and media-derived factors on the intergrity of a human monoclonal. antibody after secretion into serum-free cell culture supernatants Biotechnology and Bioengineering 45 (1995) S.97-106.*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Eduardo Padlan, Anatomy of the antibody molecule. Mol Immunol. Feb. 1994;31(3):169-217.*
Paul, Fundamental Immunology, 3rd Edition, 1993, pp. 292-295.*
Rudikoff et al Single amino acid substitution altering antigen-binding specificity. Proc Natl Acad Sci U S A. Mar. 1982;79(6):1979-83.*
Bendayan M. Possibilities of false immunocytochemical results generated by the use of monoclonal antibodies: the example of the anti-proinsulin antibody. J Histochem Cytochem. 43(9):881-6, 1995.*
U.S. Appl. No. 12/825,223, filed Jun. 28, 2010, Roberts et al.
Atkinson et al., "Characterization of placentation-specific binucleate cell glycoproteins processing a novel carbohydrate," *J. Biol. Chem.*, 268(35):26679-26685, 1993.
Avalle et al., "Development of monoclonal and polyclonal antibodies against bovine pregnancy-associated glycoproteins (PAG) for use as reagents in localization of PAG expression and for pregnancy detection," *Biology of Reproduction, Society for the Study of Reproduction*, 64 (Suppl. 1):341, 2001. Abstract.
Ayad et al., "Correlation of five radioimmunoassay systems for measurement of bovine plasma pregnancy-associated glycoprotein concentrations at early pregnancy period," *Res. Vet. Sci.*, doi:10.1016/j. rvsc.2008.10.003, 2008.
Beal et al., "The use of ultrasound in monitoring reproductive physiology of beef cattle," *J. Anim. Sci.*, 70-924-929, 1992.
Birch et al., "Homology cloning of aspartic proteases from an endocrine cell line using the polymerase chain reaction," *Biochem. Biophys. Res. Commun.*, 177(3):920-926, 1993.

(Continued)

*Primary Examiner* — Maher Haddad
(74) *Attorney, Agent, or Firm* — SNR Denton US LLP

(57) ABSTRACT

Disclosed are antibodies and methods for detecting pregnancy in an animal. In certain aspects antibodies used binds immunologically to at least two PAGs selected from PAG4, PAG6, PAG9, PAG16, PAG17, PAG19, PAG20 and PAG21. Antibody encoding nucleic acids are also provided, as are kits, methods of use and additional antibody related compositions.

28 Claims, 21 Drawing Sheets

OTHER PUBLICATIONS

Blast search results using a sequence comprising SEQ ID No. 3 as a query, dated Mar. 11, 2007.
Blast search results using SEQ ID No. 3 as a query, dated Mar. 11, 2007.
Bork, "Powers and pitfalls in sequence analysis: the 70% hurdle," *Genome Research*, 10:398-400, 2000.
Brenner, "Errors in genome annotation," *Trends in Genetics*, 15(4):132-133, 1999.
Butler et al., "Detection and partial characterization of two bovine pregnancy-specific proteins," *Biol. of Reprod.*, 26:925-933, 1982.
Cameron et al., "Evaluation of an ultrasonic Doppler probe for pregnancy diagnosis in cattle," *Austr. Vet. J.*, 70:109-111, 1993.
Campbell, Monoclonal Antibody Technology, Elsevier, New York, pp. 1-31, 1984.
Davies, "The structure and function of the aspartic proteinases," *Ann. Rev. Biophys. Chem.*, 19:189-215, 1990.
Decision on Appeal for Appeal 2007-4137 regarding U.S. Appl. No. 10/655,547, dated Nov. 8, 2007.
Garbayo et al., "Caprine pregnancy-associated glycoproteins (PAG): Their cloning expression and evolutionary relationship to other PAG," *Mol. Reprod Dev*, 57:311-322, 2000.
GenBank Accession No. A61232, dated May 12, 1994.
GenBank Accession No. AF020506, dated Mar. 29, 2000.
GenBank Accession No. AF020507, dated Mar. 29, 2000.
GenBank Accession No. AF020508, dated Mar. 29, 2000.
GenBank Accession No. AF020509, dated Sep. 7, 2007.
GenBank Accession No. AF020510, dated Mar. 29, 2000.
GenBank Accession No. AF020511, dated Mar. 29, 2000.
GenBank Accession No. AF020512, dated Aug. 20, 2007.
GenBank Accession No. AF020513, dated Mar. 29, 2000.
GenBank Accession No. AF020514, dated Mar. 29, 2000.
GenBank Accession No. L06151, dated May 5, 1995.
GenBank Accession No. L06153, dated Sep. 22, 1993.
GenBank Accession No. M73961, dated Apr. 29, 1997.
GenBank Accession No. U30251, dated Aug. 1, 1995.
GenBank Accession No. U94789, dated Apr. 30, 1997.
GenBank Accession No. U94790, dated Apr. 30, 1997.
GenBank Accession No. U94791, dated Apr. 30, 1997.
GenBank Accession No. U94792, dated Apr. 30, 1997.
GenBank Accession No. U94793, dated Apr. 30, 1997.
GenBank Accession No. U94794, dated Apr. 30, 1997.
GenBank Accession No. U94795, dated Apr. 30, 1997.
Gerrie et al., "Pregnancy-associated alpha-2 glycoprotein: development of a sensitive enzyme-linked immunoassay and comparison of serum concentrations in adults and children," *Clinical Chimica. Acta*, 155:51-60, 1986.
Green et al., "Bovine pregnancy-associated glycoproteins (PAG) exhibit distinct expression patterns during gestation," *Biol. Reprod.*, 60 (Suppl. 1):497, 1999.
Green et al., "Identification of a family of Kunitz domain proteins expressed in bovine and ovine trophoblast," *Biol. Reprod.*, 58 (Suppl. 1):310.
Green et al., "Identification of a new aspartic proteinase expressed by the outer chorionic cell layer of the equine placenta," *Biol. Reprod.*, 60:1069-1077, 1999.
Green et al., "Pregnancy-associated bovine and ovine glycoproteins exhibit spatially and temporally distinct expression patterns during pregnancy," *Biol. of Repro.*, 62:1624-1631, 2000.
Green et al., "Pregnancy-associated glycoproteins of the horse," *Biol. Reprod.*, 50 (Suppl. 1):152, 1994.
Green et al., "Pregnancy-associated glycoproteins: A family of catalytically inactive aspartic proteinases," *Mol Biol Cell*, 6 (Suppl 1):454, 1995.
Green et al., "The establishment for an ELISA for the detection of pregnancy-associated glycoproteins (PAGs) in the serum of pregnant cows and heifers," Departments of Animal Sciences and Biochemistry, University of Missouri-Columbia.
Green et al., "The establishment for an ELISA for the detection of pregnancy-associated glycoproteins (PAGs) in the serum of pregnant cows and heifers," *Theriogenology*, 63:1481-1503, 2005.

Guillomot, "Cellular interactions during implantation in domestic ruminants," *J. Reprod. Fertil.*, 49 (Supp.):39-51, 1995.
Guruprasad et al., "Comparative modeling and analysis of amino acid substitutions suggests that the family of pregnancy-associated glycoproteins includes both active and inactive aspartic proteinases," *Protein Engin.*, 9:849-856, 1996.
Haig, "Genetic conflicts in human pregnancy," *Rev. Biol.*, 68:495-532, 1993.
Holdsworth et al., "A rapid direct radioimmunoassay for the measurement of oestrone sulphate in the milk of dary cows and its use in pregnancy diagnosis," *J. Endocr.*, 95:7-12, 1982.
Hughes et al., "Adaptive diversification within a large family of recently duplicated, placentally expressed genes," *Proc. Natl. Acad. Sci., USA*, 97:3319-3323, 2000.
Hughes et al., "Aspartic proteinase phylogeny and the origin of pregnancy-associated glycoproteins," *Mol. Biol. Evol.*, 20:1940-1945, 2003.
Humblot et al., "Diagnosis of pregnancy by radioimmunoassay of a pregnancy-specific protein in the plasma of dairy cows," *Theriogenology*, 30(2):257-268, 1988.
Humblot et al., "Pregnancy-specific protein B, progesterone concentrations and embryonic mortality during early pregnancy in dairy cows," *J. Reprod. Fert.*, 83:215-223, 1988.
Humblot, "Protéines spécifiques de la gestation chez les ruminants," *Reprod. Nutr. Dévelop.*, 28(6B):1753-1762, 1988.
Humblot, "Proteins specific for gestation in ruminants," *Reprod. Nutr. Develop.*, 28(6B):1753-1762, 1988. (English translation).
Inoue et al., *Aspergillus niger* var. Macrospores proteinase B. cDNA cloning, expression, and activation of the proteinases, *Aspartic Proteinases*, 581-587, 1995.
Ishiwata et al., "Characterization of gene expression profiles in early bovine pregnancy using a custom cDNA microarray," *Mo.l Reprod. Dev.*, 65(1):9-18, 2003.
Karen et al., "Early pregnancy diagnosis in sheep by progesterone and pregnancy-associated glycoprotein tests," *Theriogenology*, 59:1941-1948, 2003.
King et al., "Development of the bovine placentome from days 20 to 29 of gestation," *J. Reprod. Gertil.*, 59:95-100, 1980.
Kiracofe et al., "Pregnancy-specific protein B in serum of postpartum beef cows," *J. Anim. Sci.*, 71:2199-2205, 1993.
Klisch et al., "Pregnancy associated glycoprotein-1,-6,-7, and -17 are major products of bovine binucleate trophoblast giant cells at midpregnancy," *Mol. Rep. and Develop.*, 71(4):453-460, 2005.
Li et al., "Mutational analysis of the vesicular stomatitis virus glycoprotein G for membrane fusion domains," *J. Virol.*, 67(7):4070-4077, 1993.
Losman et al., "Generation of high producing clone of humanized anti-B-cell lymphoma monoclonal antibody (hLL2)," Sixth Conference on Radioimmunodectection and Radioimmunotherapy of Cancer, *Cancer*, 80(12 Suppl.):2660-2666, 1997.
Lu et al., "Direct radioimmunoassay of progesterone in saliva," *J. Immunoassay*, 18(2):149-63, 1997.
Mialon et al., "Detection of pregnancy by radioimmunoassay of a pregnancy serum protein (PSP60) in cattle," *Reprod. Nutr. Dev.*, 34:65-72, 1994.
Mialon et al., "Peripheral concentrations of a 60-kDa pregnancy serum protein during gestation and after calving and in relationship to embryonic mortality in cattle," *Reprod. Nutr. Dev.*, 33:269-282, 1993.
NCBI Accession No. NM__176617, dated Jun. 6, 2010.
NCBI Accession No. NP__788788, dated Jun. 27, 2010.
NCBI Accession No. NP__788790, dated Jun. 6, 2010.
NCBI Accession No. NP__788793, dated May 30, 2010.
NCBI Accession No. NP__788802, dated Jun. 6, 2010.
NCBI Accession No. NP__788803, dated May 30, 2010.
Ngo et al., "Chapter 14: Complexity Protein Structure Prediction, and the Levinthal Paradox," In: The Protein Folding Problem and Tertiary Structure Prediction, (Merz et al., Eds.), Birkhauser, Boston, MA, pp. 433-506, 1994.
Patel et al., "Effect of fetal mass, number, and stage of gestation on pregnancy-specific protein B concentrations in the bovine," *Theriogenol.*, 44:827-833, 1995.
Patel et al., "Plasma bovine pregnancy-associated glycoprotein concentrations throughout gestation in relationship to fetal number in the cow," *Eur. J. Endoc.*, 137:423-428, 1997.

Ranilla et al., "Plasmatic profiles of pregnancy associated glycoprotein and progesterone levels during gestation in churra and merino sheep," *Theriology*, 42(3):537-545, 1994.

Roberts et al., "Glycoproteins of the aspartyl proteinase gene family secreted by the developing placenta," *Aspartic Prot., Struct., Funct., Biol., Biom., Impl.*, 231-240, 1995.

Roberts et al., "Maternal Recognition of pregnancy," *Biol. Reprod.*, 54:294-302, 1996.

Roberts et al., "New and atypical families of type I interferons in mammals: comparative functions, structures, and evolutionary relationships," *Prog. Nucl. Acid Res. Mol. Biol.*, 56:287-326, 1997.

Sasser et al., "Characterizations of pregnancy-specific protein B in cattle," *J. Reprod. Fertil.*, 37(suppl.):109-113, 1989.

Sasser et al., "Detection of pregnancy by radioimmunoassay of a novel pregnancy-specific protein in serum of cows and a profile of serum concentrations during gestation," *Biol. Reprod.*, 35(4):936-942, 1986.

Scott et al., "Serum levels of pregnancy-associated alpha 2-glycoprotein during pregnancy in autoimmune thyroid disease: relationship to disease activity," *Clinical and Experimental Immunology*, 59:564-570, 1985.

Skolnick et al., "From gene to protein structure and function: novel applications of computational approaches in genomi," *Trends in Biotech.*, 18(1):34-39, 2000.

Smith et al., "The challenges of genome sequence annotation or The Devil is in the details," *Nature Biotechnology*, 15:1222-1223, 1997.

Stanley et al., "Use of a new and rapid milk progesterone assay to monitor reproductive activity in the cow," *Veterinary Record*, 664-667, 1986.

Stefanakis et al., "Development of a simple and reliable immuno-enzymatic technique for the estimation of progesterone concentration in cows milk and sows serum," *Bull. Hellenic Vet. Med. Soc.*, 45:37-43, 1994.

Swiss-Prot Accession No. Q29432, dated Nov. 2, 2010.
Swiss-Prot Accession No. Q46492, dated Oct. 31, 2006.
Swiss-Prot Accession No. Q46494, dated Nov. 2, 2010.
Swiss-Prot Accession No. Q46497, dated Nov. 2, 2010.
Swiss-Prot Accession No. Q9TTV3, dated Nov. 28, 2006.
Swiss-Prot Accession No. Q9TTV4, dated Nov. 28, 2006.
Swiss-Prot Accession No. Q9TTV5, dated Nov. 28, 2006.
Swiss-Prot Accession No. Q9TTV7, dated Nov. 28, 2006.
Swiss-Prot Accession No. Q9TTV8, dated Nov. 28, 2006.

Szafranska et al., "Chorionic expression of heterogeneous products of the PAG (pregnancy-associated glycoprotein) gene family secreted in vitro throughout embryonic and foetal development in the pig," *Reprod. Nutr. Dev.*, 43(6):497-516, 2003.

Szafranska et al., "Gene for porcine and bovine pregnancy-associated glycoprotein 2: Its structural organization and analysis of its promoter," *Mol. Reprod. Dev.*, 66:137-146, 2001.

Szafranska et al., Porcine pregnancy-associated glycoproteins: new members of the aspartic proteinase gene family expressed in trophectoderm, *Biol. Reprod.*, 53:21-28, 1995.

Szenci et al., "Evaluation of false ultrasonographic diagnoses in cows by measuring plasma levels of bovine pregnancy-associated glycoprotein 1," *Vet. Record*, 142(12):304-306, 1998.

Takahashi et al., "Simple purification procedure for bovine pregnancy-associated glycoprotein with pepstatin A-coupled affinity chromatography," *Journal of Reproduction and Fertility, Abstract Series*, 26:32, 2000. Abstract.

U.S. Board of Appeal and Interference Decision on Appeal regarding U.S. Appl. No. 10/187,744, dated Sep. 17, 2007.

Vienravi et al., "A direct radioimmunoassay for free progesterone in saliva," *J. Med. Assoc. Thai.*, 77(3):138-147, 1994.

Warnick et al., "The relationship of the interval from breeding to uterine palpation for pregnancy diagnosis with calving outcomes in holstein cows," *Theriogenology*, 44:811-825, 1995.

Wedemayer, "Structural insights into the evolution of an antibody combining site," *Science*, 276(5319):1665-1669, 1997.

Wells, "Additivity of mutational effects in proteins," *Biochemistry*, 29(37):8509-8517, 1990.

Wooding, "Current topic: the syneptitheliochorial placenta of ruminants: binucleate cell fusions and hormone production," *Placenta*, 13:101-113, 1992.

Xie et al., "A novel glycoprotein of the aspartic proteinase gene family expressed in bovine placental trophectoderm," *Biol. Reprod.*, 51:1145-1153, 1994.

Xie et al., "Identification of the major pregnancy-specific antigens of cattle and sheep as inactive members of the aspartic proteinase family," *Proc. Natl. Acad. Sci., USA*, 88:10247-10251, 1991.

Xie et al., "Multiple pregnancy-associated glycoproteins are secreted by day 100 ovine placental tissue," *Biol. Reprod.*, 57:1384-1393, 1997.

Xie et al., "The diversity and evolutionary relationships of the pregnancy-associated glycoproteins, an aspartic proteinase subfamily consisting of many trophoblast-expressed genes," *Proc. Natl. Acad. Sci., USA*, 94:12809-12816, 1997.

Xie et al., The gene encoding bovine pregnancy-associated glycoprotein-1, an inactive member of the aspartic proteinase family,: *Gene*, 159:193-197, 1995.

Xie et al., "Trophoblast-specific processing ans phosphorylation of pregnancy-associated glycoprotein-1 in day 15 to 25 sheep placenta," *Biol. Reprod.*, 54:122-129, 1996.

Zoli et al., "Light and electron microscopic immunolocalization of bovine pregnancy-associated glycoprotein in the bovine placentome," *Biol. Reprod.*, 46:623-629, 1992.

Zoli et al., "Purification and characterization of a bovine pregnancy-associated glycoprotein," *Biol. Reprod.*, 45:1-10, 1991.

Zoli et al., "Radioimmunoassay of a bovine pregnancy-associated glycoprotein in serum: its application for pregnancy diagnosis," *Biol. Reprod.*, 46:83-92, 1992.

Akagawa et al., "Bispecific Abs against modified protein and DNA with oxidized lipids," *PNAS*, 103(16):6160-6165, 2006.

Liu et aL, "Kinetic and genetic bases for the heteroclitic recognition of mouse cytochrome c by mouse anti-pigeon cytochrome c monoclonal antibodies," *Mol. Immunol.*, 37(14):847-859, 2000.

* cited by examiner

>2D9 Light Chain
CGGTTCCTGCTTCCAGCAGTGATGTTTTGATGACCCAAACTCCACTCTCCCTGCCTGTCAGTCTT
GGAGATCAAGCCTCCATTTCTTGCAGATCTAGGCAGAGCATTGTACATAGTAATGGAAACACCTATTTAG
AATGGTTCCTGCAGAAACCAGGCCAGTCTCCAAAGCTCCTGATCTACAAAGTTTCCAACCGATTTTCTGG
GGTCCCAGACAGGTTCAGTGGCAGTGGATCAGGGACAGATTTCACACTCAAGATCAGCAGAGTGGAGGCT
GAGGATCTGGGAGTTTATTACTGCTTTCAAGGTTCACATGTTCCGCTCACGTTCGGTGCTGGGACCAAGC
TGGAGCTGAAACGGGCTGATGCTGCACCAACTGTATCCATCTTCCCACCATCCAGTGAGCAGTTAACATC
TGGAGGTGCCTCAGTCGTGTGCTTCTTGAACAACTTCTACCCCAAAGACATCAATGTCAAGTGGAAGATT
GATGGCAGTGAACGACAAAATGGCGTCCTGAACAGTTGGACTGATCAGGACAGCAAAGACAGCACCTACA
GCATGAGCAGCACCCTCACGTTGACCAAGGACGAGTATGAACGACATAACAGCTATACCTGTGAGGCCAC
TCACAAGACATCTACTTCACCCATTGTCAAGAGCTTCAACAGGAATGAGTGTTAGAGACAAAGGTCCTGA

FIG. 1

\>2D9 Heavy Chain
GCTACAGGTGTCCACTCCCAGGTTCAGCTGCAGCAGTCTGGAGCTGAGCTGATGAAGCCTGGGGCCTCAG
TGAAGATATCCTGCAAGGCTACTGGCTACATATTCAGTAACTACTGGATGGAGTGGGTAAAGCAGAGGCC
TGGACATGGCCTTGAGTGGATTGGAGAGATTTTACCTGGAAGTGATATTACTAACTACAATGAGAAGTTC
AAGGACAAGGCCACATTCACTGCAGATTCATCCTCCAACACGGCCTACATGCAACTCAGCAGCCTGACAT
CTGAGGACTCTGCCGTCTATTACTGTGCAAGAGCTGGGAGTGGTTACTACGGGGTATATTACTATGCTAT
GGACTACTGGGGTCAAGGAACCTCAGTCACCGTCTCCTCAGCCAAAACGACACCCCCATCTGTCTATCCA
CTGGCCCCTGGATCTGCTGCCCAAACTAACTCCATGGTGACCCTGGGATGCCTGGTCAAGGGCTATTTCC
CTGAGCCAGTGACAGTGACCTGGAACTCTGGATCCCTGTCCAGCGGTGTGCACACCTTCCCAGCTGTCCT
GCAGTCTGACCTCTACACTCTGAGCAGCTCAGTGACTGTCCCCTCCAGCACCTGGCCCAGCGAGACCGTC
ACCTGCAACGTTGCCCACCCGGCCAGCAGCACCAAGGTGGACAAGAAAATTGTGCCCAGGGATTGTGGTT
GTAAGCCTTGCATATGTACAGTCCCAGAAGTATCATCTGTCTTCATCTTCCCCCCAAAGCCCAAGGATGT
GCTCACCATTACTCTGACTCCTAAGGTCACGTGTGTTGTGGTAGACATCAGCAAGGATGATCCCGAGGTC
CAGTTCAGCTGGTTTGTAGATGATGTGGAGGTGCACACAGCTCAGACGCAACCCCGGGAGGAGCAGTTCA
ACAGCACTTTCCGCTCAGTCAGTGAACTTCCCATCATGCACCAGGACTGGCTCAATGGCAAGGAGTTCAA
ATGCAGGGTCAACAGTGCAGCTTTCCCTGCCCCCATCGAGAAAACCATCTCCAAAACCAAAGGCAGACCG
AAGGCTCCACAGGTGTACACCATTCCACCTCCCAAGGAGCAGATGGCCAAGGATAAAGTCAGTCTGACCT
GCATGATAACAGACTTCTTCCCTGAAGACATTACTGTGGAGTGGCAGTGGAATGGGCAGCCAGCGGAGAA
CTACAAGAACACTCAGCCCATCATGGACACAGATGGCTCTTACTTCGTCTACAGCAAGCTCAATGTGCAG
AAGAGCAACTGGGAGGCAGGAAATACTTTCACCTGCTCTGTGTTACATGAGGGCCTGCACAACCACCATA
CTGAGAAGAGCCTCTCCCACTCTCCTGGTAAATGATCCCAAAGTCCTTGGAGCCCTCTGGTCCTACAGGA
CTACTGCAGGTGTCCACTCCCCTCAAACA

FIG.2

Identification of 2D9 binding PAG antigen LC-MS-MS Analysis

Bos Taurus (NM176617) Pregnancy-associated glycoprotein 6

| Mz | Charge | Mr(calc) | Start | End | Score | Peptide sequence |
|---|---|---|---|---|---|---|
| 853.4334 | 2 | 1686.865 | 147 | 162 | 94.87% | IGDLVSTDQPFGLCLK (SEQ ID NO:7) |
| 615.2964 | 2 | 1210.602 | 183 | 193 | 95.45% | TFSGAFPIFDK (SEQ ID NO:8) |
| 886.4468 | 2 | 1752.872 | 196 | 211 | 98.95% | NEGAISEPVFAFYLSK (SEQ ID NO:9) |
| 592.9523 | 3 | 1757.815 | 212 | 227 | 89.57% | DKQEGSVVMFGGVDHR (SEQ ID NO:10) |
| 767.3938 | 3 | 2281.195 | 266 | 287 | 90.78% | ALVDTGTSDIVGPSTLVNNWK (SEQ ID NO:11) |
| 467.2134 | 2 | 914.4286 | 362 | 368 | 99% | YFSVFDR (SEQ ID NO:12) |

2D9 Binding PAG antigen

| Mz | Charge | Mr(calc) | Start | End | Score | Peptide sequence |
|---|---|---|---|---|---|---|
| 881.9511 | 2 | 1743.886 | 147 | 162 | 99.00% | IGDLVSTDQPFGLCLK (SEQ ID NO:13) |
| 615.311 | 2 | 1210.602 | 183 | 193 | 99.00% | TFSGAFPIFDK (SEQ ID NO:14) |
| 886.4475 | 2 | 1752.872 | 196 | 211 | 99.00% | NEGAISEPVFAFYLSK (SEQ ID NO:15) |
| 592.966 | 3 | 1757.815 | 212 | 227 | 95.84% | DKQEGSVVMFGGVDHR (SEQ ID NO:16) |
| 767.404 | 3 | 2281.195 | 266 | 287 | 97.54% | ALVDTGTSDIVGPSTLVNNWK (SEQ ID NO:17) |
| 467.235 | 2 | 914.4286 | 362 | 368 | 84.44% | YFSVFDR (SEQ ID NO:18) |

FIG.3A

β-Study Results
Day 28 PAG and US data

Wisconsin Site

|  | PAGs | | Percent |
|---|---|---|---|
| US | Preg | Open | Agree |
| Preg | 358 | 11 | 97.0 |
| Open | 44 | 464 | 91.3 |
|  | 402 | 475 | 877 |

| | | | |
|---|---|---|---|
| | 402 | 475 | 877 |

California Site

|  | PAGs | | Percent |
|---|---|---|---|
| US | Preg | Open | Agree |
| Preg | 391 | 18 | 95.6 |
| Open | 41 | 419 | 91.1 |
|  | 432 | 437 | 869 |

FIG. 6

*β*-Study Results:
Wisconsin-Synchronized breeding

| Characteristic | Early Resynch | Late Resynch | Significance |
|---|---|---|---|
| Number available after 1st TAI | 228 | 226 | |
| % Preg. to first insemination | 46.3 | 47.9 | NS |
| Days between inseminations | 35.1 | 42.0 | P<0.05 |
| Number of inseminations (NI) | 2.60 | 2.65 | NS |
| NI/Conception | 2.29 | 2.37 | NS |
| Days to pregnant (exclude 1st TAI) | 45.2 | 58.3 | P<0.05 |
| % Preg (exclude 1st TAI) | 46.1 | 51.4 | NS |

*Data for 30 cows to resolve

FIG.7

β-Study Results:
California–TAI+Breed to heat

| Characteristic | Early Resynch | Late Resynch | Significance |
|---|---|---|---|
| Number available after 1st TAI | 321 | 335 | |
| % Preg. to first insemination | 27.7 | 28.7 | NS |
| Days between inseminations | 28.9 | 32.3 | P<0.05 |
| Number of inseminations (NI) | 2.86 | 3.05 | P<0.05 |
| NI/Conception | 2.49 | 2.77 | P<0.05 |
| Days to pregnant (exclude 1st TAI) | 37.9 | 48.0 | P<0.05 |
| % Preg (exclude 1st TAI) | 36.6 | 36.2 | NS |

*Data for 42 cows to resolve

FIG.8

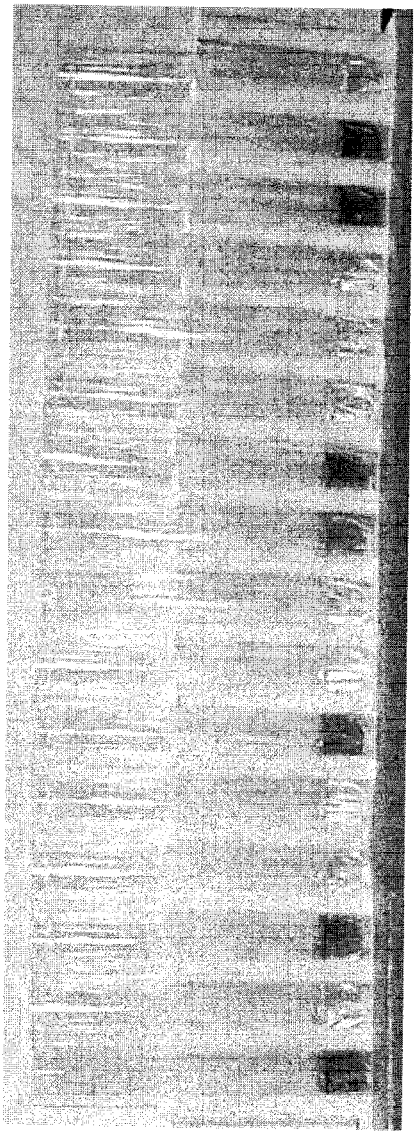

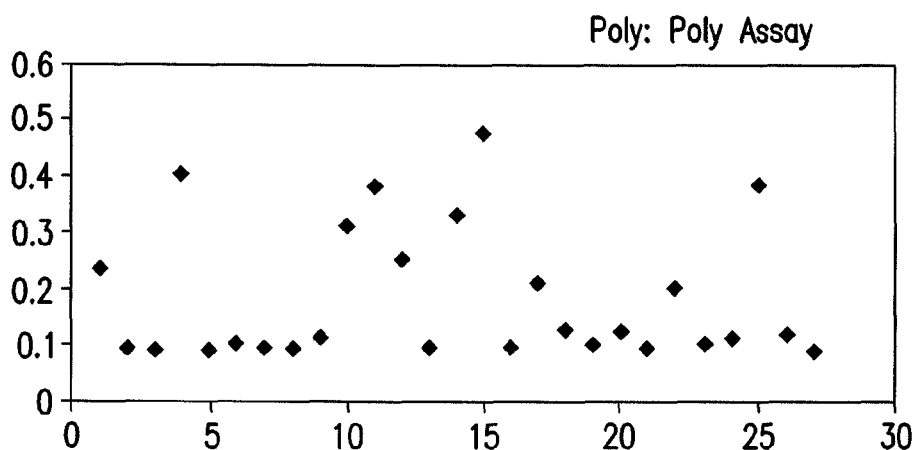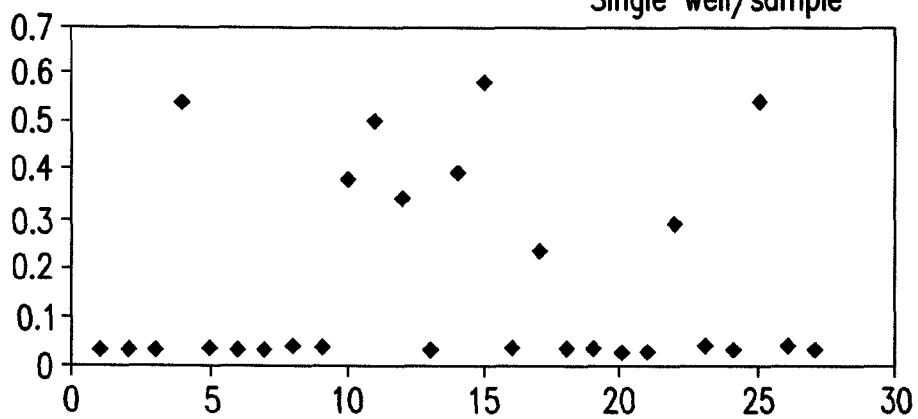
FIG.12

Color Test: Field testing
Total number of samples tested: 54
Days 33 to 34 after breeding

|  | Pregnant | Open | Recheck |
|---|---|---|---|
| PAGs | 15 | 37 | 2 |
| US | 14 | 40 | |
| Agreement | 14 | 36 | |

Test was read by 3 people
1 false-positive in tube test

|  | 10 | 20 | 30 | 40 | 50 | 60 |
|---|---|---|---|---|---|---|
| Btau\|O29432\|PAG1 | MKWLVLLGLV | AFSBCIVKIP | LRRLKTMRNV | VSGKNMLNNF | LKEHAYSLSQ | ISFRGSNLTT |
| Btau\|O46492\|PAG4 | .......... | .......... | ....V..... | L......T.I | V...R..... | .......... |
| Btau\|O46494\|PAG6 | .......... | .......... | ....V..... | ......A..I | ....R.P... | .........I |
| Btau\|A5PJW4\|PAG6 | .......... | .......... | ....V..... | ......A..I | ....R.P... | .........H |
| Btau\|A4PV16\|PAG9 | .......I.. | .......... | ...QV..KT. | L......K.. | ....P.R... | .........I |
| Btau\|O46497\|PAG9 | .......I.. | .......... | ...QV..KT. | L......K.. | ....P.R... | .........I |
| Btau\|O9TTV8\|PAG16 | ......W... | .......... | ....V..KT. | L......T.. | ....P.R.H. | .........I |
| Btau\|O9TTV7\|PAG17 | ......W... | .......... | ...QV..KT. | L......T.. | ....T..... | ........S. |
| Btau\|A7MBA4\|PAG17 | .......... | .......... | ...QV..KT. | L......T.. | ....T..... | ........S. |
| Btau\|O9TTV5\|PAG19 | .......V.. | .......F.. | ....V..KA. | L......... | ....R..... | .........I |
| Btau\|Q9TTV4\|PAG20 | .......... | .......... | ....V..KT. | L......... | ....P.K... | .........S |
| Btau\|Q9TTV3\|PAG21 | .......V.. | .......... | .......... | .......... | ..GNR..K.. | .......... |

|  | 70 | 80 | 90 | 100 | 110 | 120 |
|---|---|---|---|---|---|---|
| Btau\|O29432\|PAG1 | HPLRNIKDLV | YMGNITIGTP | PQBFQVVFDT | ASSDLWVPSD | FCTSPACSTH | VRFRHLQSST |
| Btau\|O46492\|PAG4 | PLRNIRDLFY | VGNITIGTP. | QBFQVIFDTG | S.DLWVASIF | CNS.SCAAHV | RFRH.QS.TF |
| Btau\|O46494\|PAG6 | .R.FF..V.. | .......... | ....I..... | .G.E.....I | .N.ST.K.D. | .....E.... |
| Btau\|A5PJW4\|PAG6 | PLRNIRDLFY | VGNITIGTP. | QBFQVIFDTG | S.DLWVASIF | CNS.SCAAHV | RFRH.QS.TF |
| Btau\|A4PV16\|PAG9 | .......... | .......... | .......... | G......... | ......F... | CTMPACSAPV | WFRQLQS.TF |
| Btau\|O46497\|PAG9 | .......... | .......... | .......... | G......... | ......F... | CTMPACSAPV | WFRQLQS.TF |
| Btau\|O9TTV8\|PAG16 | ....MN...V | .......... | .......... | G......... | .......... | .......F.. |
| Btau\|O9TTV7\|PAG17 | ....MN..... | .......... | .......... | G......... | .......... | .......... |
| Btau\|A7MBA4\|PAG17 | L....R.ML. | .......V.. | .......... | G......... | .....V.... | Q.L.A.K..M.I.H. |
| Btau\|O9TTV5\|PAG19 | .....M.ML. | .......V.. | .......... | G......... | .....V.... | Q.L.A.K..M.I.Y. |
| Btau\|Q9TTV4\|PAG20 | .....M.ML. | ........LA | .......FL. | G......... | .....G.K.. | ..I.I.N.ST... | .....R.... |
| Btau\|Q9TTV3\|PAG21 | L....W.IF. | .......I.T | .......... | G......F.. | .......... | .....D.I.. | .....QH... |

FIG. 16-1

```
                        130        140        150        160        170        180
                         |          |          |          |          |          |
Btau|029432|PAG1    FRLTNKTFRI TYGSGRMKGV VVHDTVRIGN LVSTDQPFGL SIEEYGFEGR IYDGVLGLNY
Btau|046492|PAG4    ....SRR.S. ....IBAL.. ........D. .........Q ..CL.S...M RF......S.
Btau|046494|PAG6    RPTNKTFRIT YGSGRMKGV. .HDTVRIGDL VSTDQPFGLC LKDSGFKGIP FDGILGLSYP
Btau|A5PJW4|PAG6    RPTNKTFRIT YGSGRMKGV. .HDTVRIGDL VSTDQPFGLC LKDSGFKGIP FDGILGLSYP
Btau|A4PV16|PAG9    QPTNKTFTIT YGSGSMKGFL AYDTVRIGDL VSTDQPFGLS VV.YGLEGRN YDGVLGLNYP
Btau|046497|PAG9    QPTNKTFTIT YGSGSMKGFL AYDTVRIGDL VSTDQPFGLS VV.YGLEGRN YDGVLGLNYP
Btau|Q9TTV8|PAG16   ..P.T..... .......... ......A... .......... .MA...L.S. RF.I......
Btau|Q9TTV7|PAG17   ..H.Q.V.N. K.NT...... ....L.Y... .......... .LA.V..D.I PF........
Btau|A7MBA4|PAG17   ..H.Q.V.N. K.NT...... ....L.Y... .......... .LA.V..D.I PF........
Btau|Q9TTV5|PAG19   ..........  ....S..... ......A... .......... .MA...L.HI PF.I......
Btau|Q9TTV4|PAG20   ..........  .......G.. ......R... .......... .VA....... RF........
Btau|Q9TTV3|PAG21   ..........  ....P..... ....S..... .......... .VS.....KD .A...I....

190        200        210        220        230        240
                         |          |          |          |          |          |
Btau|029432|PAG1    PNISFSGAIP IFDKLKNQRA ISBPVFAFYL SKDEREGSVV MFGGVDHRYY EGELNWVPLI
Btau|046492|PAG4    T...P..... ....Y..BG. .......... .......... ......A... ..K..I..M.
Btau|046494|PAG6    NKTFSGAFPI FDKLKNEGAI SBPVFAFYLS KDKQEGSV.M FG.VDHRY.K GELNWVPLIQ
Btau|A5PJW4|PAG6    NKTFSGAFPI FDKLKNEGAI SBPVFAFYLS KDKQEGSV.M FG.VDHRY.K GELNWVPLIQ
Btau|A4PV16|PAG9    NISFSGAIPI FDKLKNQGAI SBPVFAFYLS KDKQEGSV.M FG.VDHQY.K GELNWIPLIE
Btau|046497|PAG9    NISFSGAIPI FDKLKNQGAI SBPVFAFYLS KDKQEGSV.M FG.VDHQY.K GELNWIPLIE
Btau|Q9TTV8|PAG16   ..L.C..... .......... ....D.I... .......K.. .......... ..K.......
Btau|Q9TTV7|PAG17   ...M...... ....N..... .......... .......K.. .......... ..K.......
Btau|A7MBA4|PAG17   ...M...... ....N..... .......... .......K.. .......... ..K.......
Btau|Q9TTV5|PAG19   ..V.S..... .......G.. .......... ......KQ.. .......... ..R.K.....
Btau|Q9TTV4|PAG20   .......K.. ....E..BG. .......... ......KQK. .......... ..K.......
Btau|Q9TTV3|PAG21   .DE..E..... .......BG. .......I.. ......KK.. .......... ..K.......
```

```
                          250        260        270        280        290        300
                           |..........|..........|..........|..........|..........|
Btau|029432|PAG1     ..........QAGDWSVHMD RISIBRKIIA CSDGCKALVD TGTSDIVGPR RLVNNIHRLI GAIPRGSEHY
Btau|046492|PAG4     K.........               .MK..V....  .G........  .S........  ..S.T.....  .T.Q.....
Btau|046494|PAG6     VGDWFVHMDR TTMKRKV.AC SDGCKALVDT GTSDIVGPST LVN.IWKLIR ARPLGPQYFV
Btau|A5PJW4|PAG6     VGDWFVHMDR ITMKRKV.AC SDGCKALVDT GTSDIVGPST LVN.IWKLIR ARPLGPQYFV
Btau|A4PV16|PAG9     AGEWRVHMDR ISMKRTV.AC SDGCEALVHT GTSHIEGPG. LVN.IHRLIR TRPFDSKHYV
Btau|046497|PAG9     AGEWRVHMDR ISMKRTV.AC SDGCEALVHT GTSHIEGPG. LVN.IHRLIR TRPFDSKHYV
Btau|09TTV8|PAG16    R.........               .TMK.BV...  ........A.  ....L.Q.G.  .VID...K..  .T.....K..
Btau|09TTV7|PAG17    ...G.T..V.               .MK.......  ..G..E....  ....AL.K..  .....QK...  .TT....K..
Btau|A7MBA4|PAG17    ...G.T..V.               .MK.......  ..G..E....  ....AL.K..  .....QK...  .TT....K..
Btau|Q9TTV5|PAG19    ...N.II...               S.........  ..G..V.F..  I..AF.E..K  P..D.MOK..  R.K.WR.K..
```

FIG.16-2

SEQUENCE LISTING

```
<160> NUMBER OF SEQ ID NOS: 74

<210> SEQ ID NO 1
<211> LENGTH: 112
<212> TYPE: PRT
<213> ORGANISM: Artificial sequence
<220> FEATURE:
<223> OTHER INFORMATION: Artificial antibody fragment light chain
      peptide sequence

<400> SEQUENCE: 1

Asp Val Leu Met Thr Gln Thr Pro Leu Ser Leu Pro Val Ser Leu Gly
1               5                   10                  15

Asp Gln Ala Ser Ile Ser Cys Arg Ser Arg Gln Ser Ile Val His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 2
```

```
<211> LENGTH: 124
<212> TYPE: PRT
<213> ORGANISM: Artificial sequence
<220> FEATURE:
<223> OTHER INFORMATION: AArtificial antibody fragment heavy chain
      peptide sequence

<400> SEQUENCE: 2

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Ile Phe Ser Asn Tyr
                20                  25                  30

Trp Met Glu Trp Val Lys Gln Arg Pro Gly His Gly Leu Glu Trp Ile
            35                  40                  45

Gly Glu Ile Leu Pro Gly Ser Asp Ile Thr Asn Tyr Asn Glu Lys Phe
        50                  55                  60

Lys Asp Lys Ala Thr Phe Thr Ala Asp Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Gly Ser Gly Tyr Tyr Gly Val Tyr Tyr Ala Met Asp
            100                 105                 110

Tyr Trp Gly Gln Gly Thr Ser Val Thr Val Ser Ser
        115                 120

<210> SEQ ID NO 3
<211> LENGTH: 193
<212> TYPE: PRT
<213> ORGANISM: Artificial sequence
<220> FEATURE:
<223> OTHER INFORMATION: Artificial antibody fragment light chain
      peptide sequence

<400> SEQUENCE: 3

Asp Val Leu Met Thr Gln Thr Pro Leu Ser Leu Pro Val Ser Leu Gly
1               5                   10                  15

Asp Gln Ala Ser Ile Ser Cys Arg Ser Arg Gln Ser Ile Val His Ser
                20                  25                  30

Asn Gly Asn Thr Tyr Leu Glu Trp Phe Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190
```

Arg

<210> SEQ ID NO 4
<211> LENGTH: 448
<212> TYPE: PRT
<213> ORGANISM: Artificial sequence
<220> FEATURE:
<223> OTHER INFORMATION: Artificial antibody fragment heavy chain
      peptide sequence

<400> SEQUENCE: 4

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Ile Phe Ser Asn Tyr
                20                  25                  30

Trp Met Glu Trp Val Lys Gln Arg Pro Gly His Gly Leu Glu Trp Ile
            35                  40                  45

Gly Glu Ile Leu Pro Gly Ser Asp Ile Thr Asn Tyr Asn Glu Lys Phe
        50                  55                  60

Lys Asp Lys Ala Thr Phe Thr Ala Asp Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Gly Ser Gly Tyr Tyr Gly Val Tyr Tyr Ala Met Asp
                100                 105                 110

Tyr Trp Gly Gln Gly Thr Ser Val Thr Val Ser Ser Ala Lys Thr Thr
            115                 120                 125

Pro Pro Ser Val Tyr Pro Leu Ala Pro Gly Ser Ala Ala Gln Thr Asn
        130                 135                 140

Ser Met Val Thr Leu Gly Cys Leu Val Lys Gly Tyr Phe Pro Glu Pro
145                 150                 155                 160

Val Thr Val Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Pro Ser Ser Thr Trp Pro Ser Glu Thr Val Thr Cys Asn Val
        195                 200                 205

Ala His Pro Ala Ser Ser Thr Lys Val Asp Lys Lys Ile Val Pro Arg
    210                 215                 220

Asp Cys Gly Cys Lys Pro Cys Ile Cys Thr Val Pro Glu Val Ser Ser
225                 230                 235                 240

Val Phe Ile Phe Pro Pro Lys Pro Lys Asp Val Leu Thr Ile Thr Leu
                245                 250                 255

Thr Pro Lys Val Thr Cys Val Val Asp Ile Ser Lys Asp Asp Pro
            260                 265                 270

Glu Val Gln Phe Ser Trp Phe Val Asp Asp Val Glu Val His Thr Ala
        275                 280                 285

Gln Thr Gln Pro Arg Glu Glu Gln Phe Asn Ser Thr Phe Arg Ser Val
    290                 295                 300

Ser Glu Leu Pro Ile Met His Gln Asp Trp Leu Asn Gly Lys Glu Phe
305                 310                 315                 320

Lys Cys Arg Val Asn Ser Ala Ala Phe Pro Ala Pro Ile Glu Lys Thr
                325                 330                 335

Ile Ser Lys Thr Lys Gly Arg Pro Lys Ala Pro Gln Val Tyr Thr Ile
            340                 345                 350

Pro Pro Pro Lys Glu Gln Met Ala Lys Asp Lys Val Ser Leu Thr Cys
```

|  | 355 |  |  |  | 360 |  |  |  | 365 |  |  |
|---|---|---|---|---|---|---|---|---|---|---|---|
| Met | Ile | Thr | Asp | Phe | Phe | Pro | Glu | Asp | Ile | Thr | Val | Glu | Trp | Gln | Trp |
|  |  |  | 370 |  |  |  | 375 |  |  |  | 380 |

Asn Gly Gln Pro Ala Glu Asn Tyr Lys Asn Thr Gln Pro Ile Met Asp
385                 390                 395                 400

Thr Asp Gly Ser Tyr Phe Val Tyr Ser Lys Leu Asn Val Gln Lys Ser
                405                 410                 415

Asn Trp Glu Ala Gly Asn Thr Phe Thr Cys Ser Val Leu His Glu Gly
            420                 425                 430

Leu His Asn His His Thr Glu Lys Ser Leu Ser His Ser Pro Gly Lys
            435                 440                 445

<210> SEQ ID NO 5
<211> LENGTH: 695
<212> TYPE: DNA
<213> ORGANISM: Artificial sequence
<220> FEATURE:
<223> OTHER INFORMATION: Nucleic acid sequence encoding 2D9 antibody
      fragment light chain

<400> SEQUENCE: 5

```
cggttcctgc ttccagcagt gatgttttga tgacccaaac tccactctcc ctgcctgtca        60
gtcttggaga tcaagcctcc atttcttgca gatctaggca gagcattgta catagtaatg       120
gaaacaccta tttagaatgg ttcctgcaga accaggcca gtctccaaag ctcctgatct       180
acaaagtttc caaccgattt tctggggtcc cagacaggtt cagtggcagt ggatcaggga       240
cagatttcac actcaagatc agcagagtgg aggctgagga tctgggagtt tattactgct       300
ttcaaggttc acatgttccg ctcacgttcg gtgctgggac caagctggag ctgaaacggg       360
ctgatgctgc accaactgta tccatcttcc caccatccag tgagcagtta acatctggag       420
gtgcctcagt cgtgtgcttc ttgaacaact tctaccccaa agacatcaat gtcaagtgga       480
agattgatgg cagtgaacga caaaatggcg tcctgaacag ttggactgat caggacagca       540
aagacagcac ctacagcatg agcagcaccc tcacgttgac caaggacgag tatgaacgac       600
ataacagcta tacctgtgag gccactcaca agacatctac ttcacccatt gtcaagagct       660
tcaacaggaa tgagtgttag agacaaaggt cctga                                  695
```

<210> SEQ ID NO 6
<211> LENGTH: 1429
<212> TYPE: DNA
<213> ORGANISM: Artificial sequence
<220> FEATURE:
<223> OTHER INFORMATION: Nucleic acid sequence encoding 2D9 antibody
      fragment heavy chain

<400> SEQUENCE: 6

```
gctacaggtg tccactccca ggttcagctg cagcagtctg gagctgagct gatgaagcct        60
ggggcctcag tgaagatatc ctgcaaggct actggctaca tattcagtaa ctactggatg       120
gagtgggtaa agcagaggcc tggacatggc cttgagtgga ttggagagat tttacctgga       180
agtgatatta ctaactacaa tgagaagttc aaggacaagg ccacattcac tgcagattca       240
tcctccaaca cggcctacat gcaactcagc agcctgacat ctgaggactc tgccgtctat       300
tactgtgcaa gagctgggag tggttactac ggggtatatt actatgctat ggactactgg       360
ggtcaaggaa cctcagtcac cgtctcctca gccaaaacga cacccccatc tgtctatcca       420
ctggcccctg atctgctgc ccaaactaac tccatggtga ccctgggatg cctggtcaag       480
ggctatttcc ctgagccagt gacagtgacc tggaactctg gatccctgtc cagcggtgtg       540
```

-continued

```
cacaccttcc cagctgtcct gcagtctgac ctctacactc tgagcagctc agtgactgtc    600
ccctccagca cctggcccag cgagaccgtc acctgcaacg ttgcccaccc ggccagcagc    660
accaaggtgg acaagaaaat tgtgcccagg gattgtggtt gtaagccttg catatgtaca    720
gtcccagaag tatcatctgt cttcatcttc ccccaaagc ccaaggatgt gctcaccatt     780
actctgactc ctaaggtcac gtgtgttgtg gtagacatca gcaaggatga tcccgaggtc    840
cagttcagct ggtttgtaga tgatgtggag gtgcacacag ctcagacgca accccgggag    900
gagcagttca acagcacttt ccgctcagtc agtgaacttc ccatcatgca ccaggactgg    960
ctcaatggca aggagttcaa atgcagggtc aacagtgcag cttTccctgc ccccatcgag   1020
aaaaccatct ccaaaaccaa aggcagaccg aaggctccac aggtgtacac cattccacct   1080
cccaaggagc agatggccaa ggataaagtc agtctgacct gcatgataac agacttcttc   1140
cctgaagaca ttactgtgga gtggcagtgg aatgggcagc cagcggagaa ctacaagaac   1200
actcagccca tcatggacac agatggctct tacttcgtct acagcaagct caatgtgcag   1260
aagagcaact gggaggcagg aaatactttc acctgctctg tgttacatga gggcctgcac   1320
aaccaccata ctgagaagag cctctcccac tctcctggta atgatcccaa agtccttgg    1380 agccctctgg tcctacagga ctactgcagg tgtccactcc cctcaaaca               1429
```

<210> SEQ ID NO 7
<211> LENGTH: 16
<212> TYPE: PRT
<213> ORGANISM: Bos taurus

<400> SEQUENCE: 7

Ile Gly Asp Leu Val Ser Thr Asp Gln Pro Phe Gly Leu Cys Leu Lys
1               5                   10                  15

<210> SEQ ID NO 8
<211> LENGTH: 11
<212> TYPE: PRT
<213> ORGANISM: Bos taurus

<400> SEQUENCE: 8

Thr Phe Ser Gly Ala Phe Pro Ile Phe Asp Lys
1               5                   10

<210> SEQ ID NO 9
<211> LENGTH: 16
<212> TYPE: PRT
<213> ORGANISM: Bos taurus

<400> SEQUENCE: 9

Asn Glu Gly Ala Ile Ser Glu Pro Val Phe Ala Phe Tyr Leu Ser Lys
1               5                   10                  15

<210> SEQ ID NO 10
<211> LENGTH: 16
<212> TYPE: PRT
<213> ORGANISM: Bos taurus

<400> SEQUENCE: 10

Asp Lys Gln Glu Gly Ser Val Val Met Phe Gly Gly Val Asp His Arg
1               5                   10                  15

<210> SEQ ID NO 11
<211> LENGTH: 22
<212> TYPE: PRT
<213> ORGANISM: Bos taurus

<400> SEQUENCE: 11

Ala Leu Val Asp Thr Gly Thr Ser Asp Ile Val Gly Pro Ser Thr Leu
1               5                   10                  15

Val Asn Asn Ile Trp Lys
            20

<210> SEQ ID NO 12
<211> LENGTH: 7
<212> TYPE: PRT
<213> ORGANISM: Bos taurus

<400> SEQUENCE: 12

Tyr Phe Ser Val Phe Asp Arg
1               5

<210> SEQ ID NO 13
<211> LENGTH: 16
<212> TYPE: PRT
<213> ORGANISM: Bos taurus

<400> SEQUENCE: 13

Ile Gly Asp Leu Val Ser Thr Asp Gln Pro Phe Gly Leu Cys Leu Lys
1               5                   10                  15

<210> SEQ ID NO 14
<211> LENGTH: 11
<212> TYPE: PRT
<213> ORGANISM: Bos taurus

<400> SEQUENCE: 14

Thr Phe Ser Gly Ala Phe Pro Ile Phe Asp Lys
1               5                   10

<210> SEQ ID NO 15
<211> LENGTH: 16
<212> TYPE: PRT
<213> ORGANISM: Bos taurus

<400> SEQUENCE: 15

Asn Glu Gly Ala Ile Ser Glu Pro Val Phe Ala Phe Tyr Leu Ser Lys
1               5                   10                  15

<210> SEQ ID NO 16
<211> LENGTH: 16
<212> TYPE: PRT
<213> ORGANISM: Bos taurus

<400> SEQUENCE: 16

Asp Lys Gln Glu Gly Ser Val Val Met Phe Gly Gly Val Asp His Arg
1               5                   10                  15

<210> SEQ ID NO 17
<211> LENGTH: 22
<212> TYPE: PRT
<213> ORGANISM: Bos taurus

<400> SEQUENCE: 17

Ala Leu Val Asp Thr Gly Thr Ser Asp Ile Val Gly Pro Ser Thr Leu
1               5                   10                  15

Val Asn Asn Ile Trp Lys
            20

<210> SEQ ID NO 18

```
<211> LENGTH: 7
<212> TYPE: PRT
<213> ORGANISM: Bos taurus

<400> SEQUENCE: 18

Tyr Phe Ser Val Phe Asp Arg
1               5

<210> SEQ ID NO 19
<211> LENGTH: 9
<212> TYPE: PRT
<213> ORGANISM: Bos taurus

<400> SEQUENCE: 19

Val Pro Gly Gln Ala Tyr Ile Leu Lys
1               5

<210> SEQ ID NO 20
<211> LENGTH: 8
<212> TYPE: PRT
<213> ORGANISM: Bos taurus

<400> SEQUENCE: 20

Leu Tyr Phe Ser Val Phe Asp Arg
1               5

<210> SEQ ID NO 21
<211> LENGTH: 10
<212> TYPE: PRT
<213> ORGANISM: Bos taurus

<400> SEQUENCE: 21

Thr Phe Ser Ile Thr Tyr Gly Ser Gly Arg
1               5                   10

<210> SEQ ID NO 22
<211> LENGTH: 10
<212> TYPE: PRT
<213> ORGANISM: Bos taurus

<400> SEQUENCE: 22

Gly Glu Leu Asn Trp Ile Pro Leu Met Lys
1               5                   10

<210> SEQ ID NO 23
<211> LENGTH: 18
<212> TYPE: PRT
<213> ORGANISM: Bos taurus

<400> SEQUENCE: 23

Leu Lys Asn Glu Gly Ala Ile Ser Glu Pro Val Phe Ala Phe Tyr Leu
1               5                   10                  15

Ser Lys

<210> SEQ ID NO 24
<211> LENGTH: 23
<212> TYPE: PRT
<213> ORGANISM: Bos taurus

<400> SEQUENCE: 24

Phe Asp Gly Val Leu Gly Leu Ser Tyr Thr Asn Ile Ser Pro Ser Gly
1               5                   10                  15

Ala Ile Pro Ile Phe Tyr Lys
            20
```

```
<210> SEQ ID NO 25
<211> LENGTH: 16
<212> TYPE: PRT
<213> ORGANISM: Bos taurus

<400> SEQUENCE: 25

Asn Glu Gly Ala Ile Ser Glu Pro Val Phe Ala Phe Tyr Leu Ser Lys
1               5                   10                  15

<210> SEQ ID NO 26
<211> LENGTH: 16
<212> TYPE: PRT
<213> ORGANISM: Bos taurus

<400> SEQUENCE: 26

Ile Gly Asp Leu Val Ser Thr Asp Gln Pro Phe Gly Leu Cys Leu Lys
1               5                   10                  15

<210> SEQ ID NO 27
<211> LENGTH: 20
<212> TYPE: PRT
<213> ORGANISM: Bos taurus

<400> SEQUENCE: 27

Gly Glu Leu Asn Trp Val Pro Leu Ile Gln Val Gly Asp Trp Phe Val
1               5                   10                  15

His Met Asp Arg
            20

<210> SEQ ID NO 28
<211> LENGTH: 18
<212> TYPE: PRT
<213> ORGANISM: Bos taurus

<400> SEQUENCE: 28

Leu Lys Asn Glu Gly Ala Ile Ser Glu Pro Val Phe Ala Phe Tyr Leu
1               5                   10                  15

Ser Lys

<210> SEQ ID NO 29
<211> LENGTH: 11
<212> TYPE: PRT
<213> ORGANISM: Bos taurus

<400> SEQUENCE: 29

Thr Phe Ser Gly Ala Phe Pro Ile Phe Asp Lys
1               5                   10

<210> SEQ ID NO 30
<211> LENGTH: 16
<212> TYPE: PRT
<213> ORGANISM: Bos taurus

<400> SEQUENCE: 30

Asp Lys Gln Glu Gly Ser Val Val Met Phe Gly Gly Val Asp His Arg
1               5                   10                  15

<210> SEQ ID NO 31
<211> LENGTH: 14
<212> TYPE: PRT
<213> ORGANISM: Bos taurus

<400> SEQUENCE: 31

Gln Glu Gly Ser Val Val Met Phe Gly Gly Val Asp His Arg
```

```
<210> SEQ ID NO 32
<211> LENGTH: 7
<212> TYPE: PRT
<213> ORGANISM: Bos taurus

<400> SEQUENCE: 32

Tyr Phe Ser Val Phe Asp Arg
1               5

<210> SEQ ID NO 33
<211> LENGTH: 7
<212> TYPE: PRT
<213> ORGANISM: Bos taurus

<400> SEQUENCE: 33

Tyr Phe Ser Val Phe Asp Arg
1               5

<210> SEQ ID NO 34
<211> LENGTH: 9
<212> TYPE: PRT
<213> ORGANISM: Bos taurus

<400> SEQUENCE: 34

Gly Phe Leu Ala Tyr Asp Thr Val Arg
1               5

<210> SEQ ID NO 35
<211> LENGTH: 17
<212> TYPE: PRT
<213> ORGANISM: Bos taurus

<400> SEQUENCE: 35

Gln Glu Gly Ser Val Val Met Phe Gly Gly Val Asp His Gln Tyr Tyr
1               5                   10                  15

Lys

<210> SEQ ID NO 36
<211> LENGTH: 17
<212> TYPE: PRT
<213> ORGANISM: Bos taurus

<400> SEQUENCE: 36

Gln Glu Gly Ser Val Val Met Phe Gly Gly Val Asp His Gln Tyr Tyr
1               5                   10                  15

Lys

<210> SEQ ID NO 37
<211> LENGTH: 11
<212> TYPE: PRT
<213> ORGANISM: Bos taurus

<400> SEQUENCE: 37

Glu Thr Trp Ile Leu Gly Asp Ala Phe Leu Arg
1               5                   10

<210> SEQ ID NO 38
<211> LENGTH: 19
<212> TYPE: PRT
<213> ORGANISM: Bos taurus

<400> SEQUENCE: 38
```

```
Asn Lys Gln Glu Gly Ser Val Val Met Phe Gly Gly Val Asp His Gln
1               5                   10                  15

Tyr Tyr Lys

<210> SEQ ID NO 39
<211> LENGTH: 13
<212> TYPE: PRT
<213> ORGANISM: Bos taurus

<400> SEQUENCE: 39

Tyr Leu Pro Ser Ile Thr Phe Ile Ile Asn Gly Ile Lys
1               5                   10

<210> SEQ ID NO 40
<211> LENGTH: 23
<212> TYPE: PRT
<213> ORGANISM: Bos taurus

<400> SEQUENCE: 40

Ile Gly Asp Leu Val Ser Thr Asp Gln Pro Phe Gly Leu Ser Val Val
1               5                   10                  15

Glu Tyr Gly Leu Glu Gly Arg
            20

<210> SEQ ID NO 41
<211> LENGTH: 25
<212> TYPE: PRT
<213> ORGANISM: Bos taurus

<400> SEQUENCE: 41

Thr Val Ile Ala Cys Ser Asp Gly Cys Glu Ala Leu Val His Thr Gly
1               5                   10                  15

Thr Ser His Ile Glu Gly Pro Gly Arg
            20                  25

<210> SEQ ID NO 42
<211> LENGTH: 18
<212> TYPE: PRT
<213> ORGANISM: Bos taurus

<400> SEQUENCE: 42

Leu Lys Asn Glu Gly Ala Ile Ser Glu Pro Val Phe Ala Phe Tyr Leu
1               5                   10                  15

Ser Lys

<210> SEQ ID NO 43
<211> LENGTH: 14
<212> TYPE: PRT
<213> ORGANISM: Bos taurus

<400> SEQUENCE: 43

Gln Lys Gly Ser Val Val Met Phe Gly Gly Val Asp His Arg
1               5                   10

<210> SEQ ID NO 44
<211> LENGTH: 16
<212> TYPE: PRT
<213> ORGANISM: Bos taurus

<400> SEQUENCE: 44

Asn Glu Gly Ala Ile Ser Glu Pro Val Phe Ala Phe Tyr Leu Ser Lys
1               5                   10                  15
```

```
<210> SEQ ID NO 45
<211> LENGTH: 8
<212> TYPE: PRT
<213> ORGANISM: Bos taurus

<400> SEQUENCE: 45

Val Tyr Phe Ser Val Phe Asp Arg
1               5

<210> SEQ ID NO 46
<211> LENGTH: 10
<212> TYPE: PRT
<213> ORGANISM: Bos taurus

<400> SEQUENCE: 46

Thr Phe Ser Ile Thr Tyr Gly Ser Gly Arg
1               5                   10

<210> SEQ ID NO 47
<211> LENGTH: 20
<212> TYPE: PRT
<213> ORGANISM: Bos taurus

<400> SEQUENCE: 47

Val Val Ala Cys Ser Asp Gly Cys Glu Ala Val Val Asp Thr Gly Thr
1               5                   10                  15

Ser Leu Ile Lys
            20

<210> SEQ ID NO 48
<211> LENGTH: 21
<212> TYPE: PRT
<213> ORGANISM: Bos taurus

<400> SEQUENCE: 48

Ile Gly Asp Leu Val Ser Thr Asp Gln Pro Phe Gly Leu Ser Val Ser
1               5                   10                  15

Glu Tyr Gly Phe Lys
            20

<210> SEQ ID NO 49
<211> LENGTH: 24
<212> TYPE: PRT
<213> ORGANISM: Bos taurus

<400> SEQUENCE: 49

Ala Tyr Asp Gly Ile Leu Gly Leu Asn Tyr Pro Asp Glu Ser Phe Ser
1               5                   10                  15

Glu Ala Ile Pro Ile Phe Asp Lys
            20

<210> SEQ ID NO 50
<211> LENGTH: 16
<212> TYPE: PRT
<213> ORGANISM: Bos taurus

<400> SEQUENCE: 50

Phe Ser Ser Ser Thr Glu Thr Trp Leu Leu Gly Asp Ala Phe Leu Arg
1               5                   10                  15

<210> SEQ ID NO 51
<211> LENGTH: 380
<212> TYPE: PRT
<213> ORGANISM: Bos taurus
```

```
<400> SEQUENCE: 51

Met Lys Trp Leu Val Leu Leu Gly Leu Val Ala Phe Ser Glu Cys Ile
1               5                   10                  15

Val Lys Ile Pro Leu Arg Arg Leu Lys Thr Met Arg Asn Val Ser
            20                  25                  30

Gly Lys Asn Met Leu Asn Asn Phe Leu Lys Glu His Ala Tyr Ser Leu
                35                  40                  45

Ser Gln Ile Ser Phe Arg Gly Ser Asn Leu Thr Thr His Pro Leu Arg
        50                  55                  60

Asn Ile Lys Asp Leu Val Tyr Met Gly Asn Ile Thr Ile Gly Thr Pro
65                  70                  75                  80

Pro Gln Glu Phe Gln Val Val Phe Asp Thr Ala Ser Ser Asp Leu Trp
                85                  90                  95

Val Pro Ser Asp Phe Cys Thr Ser Pro Ala Cys Ser Thr His Val Arg
            100                 105                 110

Phe Arg His Leu Gln Ser Ser Thr Phe Arg Leu Thr Asn Lys Thr Phe
                115                 120                 125

Arg Ile Thr Tyr Gly Ser Gly Arg Met Lys Gly Val Val His Asp
130                 135                 140

Thr Val Arg Ile Gly Asn Leu Val Ser Thr Asp Gln Pro Phe Gly Leu
145                 150                 155                 160

Ser Ile Glu Glu Tyr Gly Phe Glu Gly Arg Ile Tyr Asp Gly Val Leu
                165                 170                 175

Gly Leu Asn Tyr Pro Asn Ile Ser Phe Ser Gly Ala Ile Pro Ile Phe
            180                 185                 190

Asp Lys Leu Lys Asn Gln Arg Ala Ile Ser Glu Pro Val Phe Ala Phe
            195                 200                 205

Tyr Leu Ser Lys Asp Glu Arg Glu Gly Ser Val Val Met Phe Gly Gly
        210                 215                 220

Val Asp His Arg Tyr Tyr Glu Gly Glu Leu Asn Trp Val Pro Leu Ile
225                 230                 235                 240

Gln Ala Gly Asp Trp Ser Val His Met Asp Arg Ile Ser Ile Glu Arg
                245                 250                 255

Lys Ile Ile Ala Cys Ser Asp Gly Cys Lys Ala Leu Val Asp Thr Gly
            260                 265                 270

Thr Ser Asp Ile Val Gly Pro Arg Leu Val Asn Asn Ile His Arg
        275                 280                 285

Leu Ile Gly Ala Ile Pro Arg Gly Ser Glu His Tyr Val Pro Cys Ser
    290                 295                 300

Glu Val Asn Thr Leu Pro Ser Ile Val Phe Thr Ile Asn Gly Ile Asn
305                 310                 315                 320

Tyr Pro Val Pro Gly Arg Ala Tyr Ile Leu Lys Asp Arg Gly Arg
                325                 330                 335

Cys Tyr Thr Thr Phe Gln Glu Asn Arg Val Ser Ser Thr Glu Thr
                340                 345                 350

Trp Tyr Leu Gly Asp Val Phe Leu Arg Leu Tyr Phe Ser Val Phe Asp
        355                 360                 365

Arg Gly Asn Asp Arg Ile Gly Leu Ala Arg Ala Val
370                 375                 380

<210> SEQ ID NO 52
<211> LENGTH: 380
<212> TYPE: PRT
<213> ORGANISM: Bos taurus
```

<400> SEQUENCE: 52

```
Met Lys Trp Leu Val Leu Leu Gly Leu Val Ala Phe Ser Glu Cys Ile
1               5                   10                  15

Val Lys Ile Pro Leu Arg Arg Val Lys Thr Met Thr Lys Thr Leu Ser
            20                  25                  30

Gly Lys Asn Met Leu Asn Asn Phe Val Lys Glu His Ala Tyr Arg Leu
        35                  40                  45

Ser Gln Ile Ser Phe Arg Gly Ser Asn Leu Thr Ile His Pro Leu Arg
    50                  55                  60

Asn Ile Arg Asp Phe Phe Tyr Val Gly Asn Ile Thr Ile Gly Thr Pro
65                  70                  75                  80

Pro Gln Glu Phe Gln Val Ile Phe Asp Thr Gly Ser Ser Glu Leu Trp
                85                  90                  95

Val Pro Ser Ile Phe Cys Asn Ser Ser Thr Cys Ser Lys His Asp Arg
            100                 105                 110

Phe Arg His Leu Glu Ser Ser Thr Phe Arg Leu Ser Arg Thr Phe
        115                 120                 125

Ser Ile Thr Tyr Gly Ser Gly Arg Ile Glu Ala Leu Val Val His Asp
    130                 135                 140

Thr Val Arg Ile Gly Asp Leu Val Ser Thr Asp Gln Gln Phe Gly Leu
145                 150                 155                 160

Cys Leu Glu Glu Ser Gly Phe Glu Gly Met Arg Phe Asp Gly Val Leu
                165                 170                 175

Gly Leu Ser Tyr Thr Asn Ile Ser Pro Ser Gly Ala Ile Pro Ile Phe
            180                 185                 190

Tyr Lys Leu Lys Asn Glu Gly Ala Ile Ser Glu Pro Val Phe Ala Phe
        195                 200                 205

Tyr Leu Ser Lys Asp Glu Arg Glu Gly Ser Val Val Met Phe Gly Gly
    210                 215                 220

Ala Asp His Arg Tyr Tyr Lys Gly Glu Leu Asn Trp Ile Pro Leu Met
225                 230                 235                 240

Lys Ala Gly Asp Trp Ser Val His Met Asp Arg Ile Ser Met Lys Arg
                245                 250                 255

Lys Val Ile Ala Cys Ser Gly Gly Cys Lys Ala Leu Val Asp Thr Gly
            260                 265                 270

Ser Ser Asp Ile Val Gly Pro Ser Thr Leu Val Asn Asn Ile Trp Lys
        275                 280                 285

Leu Ile Gly Ala Thr Pro Gln Gly Ser Glu His Tyr Val Ser Cys Ser
    290                 295                 300

Ala Val Asn Ser Leu Pro Ser Ile Ile Phe Thr Ile Lys Ser Asn Asn
305                 310                 315                 320

Tyr Arg Val Pro Gly Gln Ala Tyr Ile Leu Lys Asp Ser Arg Gly Arg
                325                 330                 335

Cys Phe Thr Ala Phe Lys Gly His Gln Gln Ser Ser Thr Glu Met
            340                 345                 350

Trp Ile Leu Gly Asp Val Phe Leu Arg Leu Tyr Phe Ser Val Phe Asp
        355                 360                 365

Arg Arg Lys Asp Arg Ile Gly Leu Ala Thr Lys Val
    370                 375                 380

<210> SEQ ID NO 53
<211> LENGTH: 379
<212> TYPE: PRT
<213> ORGANISM: Bos taurus
```

<400> SEQUENCE: 53

| | | | | | | | | | | | | | | |
|---|---|---|---|---|---|---|---|---|---|---|---|---|---|---|
|Met|Lys|Trp|Leu|Val|Leu|Leu|Gly|Leu|Val|Ala|Phe|Ser|Glu|Cys|Ile
|1| | | |5| | | | |10| | | | |15|
|Val|Lys|Ile|Pro|Leu|Arg|Arg|Val|Lys|Thr|Met|Arg|Asn|Ala|Ile|Ser
| | | |20| | | | |25| | | | |30| |
|Gly|Lys|Asn|Thr|Leu|Asn|Asn|Ile|Leu|Lys|Glu|His|Ala|Tyr|Arg|Leu
| | | |35| | | | |40| | | | |45| |
|Pro|Gln|Ile|Ser|Phe|Arg|Gly|Ser|Asn|Leu|Thr|His|Pro|Leu|Arg|Asn
| |50| | | | |55| | | | |60| | | |
|Ile|Arg|Asp|Leu|Phe|Tyr|Val|Gly|Asn|Ile|Thr|Ile|Gly|Thr|Pro|Pro
|65| | | | |70| | | | |75| | | | |80
|Gln|Glu|Phe|Gln|Val|Ile|Phe|Asp|Thr|Gly|Ser|Ser|Asp|Leu|Trp|Val
| | | | |85| | | | |90| | | | |95| |
|Ala|Ser|Ile|Phe|Cys|Asn|Ser|Ser|Cys|Ala|Ala|His|Val|Arg|Phe|
| | | | |100| | | | |105| | | | |110| |
|Arg|His|His|Gln|Ser|Ser|Thr|Phe|Arg|Pro|Thr|Asn|Lys|Thr|Phe|Arg
| | | |115| | | | |120| | | | |125| | |
|Ile|Thr|Tyr|Gly|Ser|Gly|Arg|Met|Lys|Gly|Val|Val|His|Asp|Thr|
| | |130| | | | |135| | | | |140| | | |
|Val|Arg|Ile|Gly|Asp|Leu|Val|Ser|Thr|Asp|Gln|Pro|Phe|Gly|Leu|Cys
|145| | | | |150| | | | |155| | | | |160
|Leu|Lys|Asp|Ser|Gly|Phe|Lys|Gly|Ile|Pro|Phe|Asp|Gly|Ile|Leu|Gly
| | | | |165| | | | |170| | | | |175| |
|Leu|Ser|Tyr|Pro|Asn|Lys|Thr|Phe|Ser|Gly|Ala|Phe|Pro|Ile|Phe|Asp
| | | |180| | | | |185| | | | |190| | |
|Lys|Leu|Lys|Asn|Glu|Gly|Ala|Ile|Ser|Glu|Pro|Val|Phe|Ala|Phe|Tyr
| | | |195| | | | |200| | | | |205| | |
|Leu|Ser|Lys|Asp|Lys|Gln|Glu|Gly|Ser|Val|Val|Met|Phe|Gly|Gly|Val
| |210| | | | |215| | | | |220| | | | |
|Asp|His|Arg|Tyr|Tyr|Lys|Gly|Glu|Leu|Asn|Trp|Val|Pro|Leu|Ile|Gln
|225| | | | |230| | | | |235| | | | |240|
|Val|Gly|Asp|Trp|Phe|Val|His|Met|Asp|Arg|Thr|Thr|Met|Lys|Arg|Lys
| | | | |245| | | | |250| | | | |255| |
|Val|Ile|Ala|Cys|Ser|Asp|Gly|Cys|Lys|Ala|Leu|Val|Asp|Thr|Gly|Thr
| | | |260| | | | |265| | | | |270| | |
|Ser|Asp|Ile|Val|Gly|Pro|Ser|Thr|Leu|Val|Asn|Asn|Ile|Trp|Lys|Leu
| | |275| | | | |280| | | | |285| | | |
|Ile|Arg|Ala|Arg|Pro|Leu|Gly|Pro|Gln|Tyr|Phe|Val|Ser|Cys|Ser|Ala
| |290| | | | |295| | | | |300| | | | |
|Val|Asn|Thr|Leu|Pro|Ser|Ile|Ile|Phe|Thr|Ile|Asn|Gly|Ile|Asn|Tyr
|305| | | | |310| | | | |315| | | | |320|
|Arg|Leu|Pro|Ala|Arg|Ala|Tyr|Ile|His|Lys|Asp|Ser|Arg|Gly|Arg|Cys
| | | |325| | | | |330| | | | |335| | |
|Tyr|Thr|Ala|Phe|Lys|Glu|His|Arg|Phe|Ser|Ser|Pro|Ile|Glu|Thr|Trp
| | | |340| | | | |345| | | | |350| | |
|Leu|Leu|Gly|Asp|Val|Phe|Leu|Arg|Arg|Tyr|Phe|Ser|Val|Phe|Asp|Arg
| | |355| | | | |360| | | | |365| | | |
|Gly|Asn|Asp|Arg|Ile|Gly|Leu|Ala|Arg|Ala|Val| | | | | |
| |370| | | | |375| | | | | | | | | |

<210> SEQ ID NO 54
<211> LENGTH: 379
<212> TYPE: PRT
<213> ORGANISM: Bos taurus

<400> SEQUENCE: 54

```
Met Lys Trp Leu Val Leu Leu Gly Leu Val Ala Phe Ser Glu Cys Ile
1               5                   10                  15
Val Lys Ile Pro Leu Arg Arg Val Lys Thr Met Arg Asn Ala Ile Ser
            20                  25                  30
Gly Lys Asn Thr Leu Asn Asn Ile Leu Lys Glu His Ala Tyr Arg Leu
        35                  40                  45
Pro Gln Ile Ser Phe Arg Gly Ser Asn Leu Thr His Pro Leu Arg Asn
    50                  55                  60
Ile Arg Asp Leu Phe Tyr Val Gly Asn Ile Thr Ile Gly Thr Pro Pro
65                  70                  75                  80
Gln Glu Phe Gln Val Ile Phe Asp Thr Gly Ser Ser Asp Leu Trp Val
                85                  90                  95
Ala Ser Ile Phe Cys Asn Ser Ser Cys Ala Ala His Val Arg Phe
            100                 105                 110
Arg His His Gln Ser Ser Thr Phe Arg Pro Thr Asn Lys Thr Phe Arg
            115                 120                 125
Ile Thr Tyr Gly Ser Gly Arg Met Lys Gly Val Val His Asp Thr
130                 135                 140
Val Arg Ile Gly Asp Leu Val Ser Thr Asp Gln Pro Phe Gly Leu Cys
145                 150                 155                 160
Leu Lys Asp Ser Gly Phe Lys Gly Ile Pro Phe Asp Gly Ile Leu Gly
                165                 170                 175
Leu Ser Tyr Pro Asn Lys Thr Phe Ser Gly Ala Phe Pro Ile Phe Asp
            180                 185                 190
Lys Leu Lys Asn Glu Gly Ala Ile Ser Glu Pro Val Phe Ala Phe Tyr
        195                 200                 205
Leu Ser Lys Asp Lys Gln Glu Gly Ser Val Val Met Phe Gly Gly Val
    210                 215                 220
Asp His Arg Tyr Tyr Lys Gly Glu Leu Asn Trp Val Pro Leu Ile Gln
225                 230                 235                 240
Val Gly Asp Trp Phe Val His Met Asp Arg Ile Thr Met Lys Arg Lys
                245                 250                 255
Val Ile Ala Cys Ser Asp Gly Cys Lys Ala Leu Val Asp Thr Gly Thr
            260                 265                 270
Ser Asp Ile Val Gly Pro Ser Thr Leu Val Asn Asn Ile Trp Lys Leu
        275                 280                 285
Ile Arg Ala Arg Pro Leu Gly Pro Gln Tyr Phe Val Ser Cys Ser Ala
    290                 295                 300
Val Asn Thr Leu Pro Ser Ile Ile Phe Thr Ile Asn Gly Ile Asn Tyr
305                 310                 315                 320
Arg Leu Pro Ala Arg Ala Tyr Ile His Lys Asp Ser Arg Gly Arg Cys
                325                 330                 335
Tyr Thr Ala Phe Lys Glu His Arg Phe Ser Ser Pro Ile Glu Thr Trp
            340                 345                 350
Leu Leu Gly Asp Val Phe Leu Arg Arg Tyr Phe Ser Val Phe Asp Arg
        355                 360                 365
Gly Asn Asp Arg Ile Gly Leu Ala Arg Ala Val
    370                 375
```

<210> SEQ ID NO 55
<211> LENGTH: 379
<212> TYPE: PRT
<213> ORGANISM: Bos taurus

<400> SEQUENCE: 55

```
Met Lys Trp Ile Val Leu Leu Gly Leu Val Ala Phe Ser Glu Cys Ile
1               5                   10                  15

Val Lys Ile Pro Leu Arg Gln Val Lys Thr Met Arg Lys Thr Leu Ser
            20                  25                  30

Gly Lys Asn Met Leu Lys Asn Phe Leu Lys Glu His Pro Tyr Arg Leu
        35                  40                  45

Ser Gln Ile Ser Phe Arg Gly Ser Asn Leu Thr Ile His Pro Leu Arg
    50                  55                  60

Asn Ile Met Asn Leu Val Tyr Val Gly Asn Ile Thr Ile Gly Thr Pro
65                  70                  75                  80

Pro Gln Glu Phe Gln Val Val Phe Asp Thr Gly Ser Ser Asp Leu Trp
                85                  90                  95

Val Pro Ser Phe Cys Thr Met Pro Ala Cys Ser Ala Pro Val Trp Phe
            100                 105                 110

Arg Gln Leu Gln Ser Ser Thr Phe Gln Pro Thr Asn Lys Thr Phe Thr
        115                 120                 125

Ile Thr Tyr Gly Ser Gly Ser Met Lys Gly Phe Leu Ala Tyr Asp Thr
    130                 135                 140

Val Arg Ile Gly Asp Leu Val Ser Thr Asp Gln Pro Phe Gly Leu Ser
145                 150                 155                 160

Val Val Glu Tyr Gly Leu Glu Gly Arg Asn Tyr Asp Gly Val Leu Gly
                165                 170                 175

Leu Asn Tyr Pro Asn Ile Ser Phe Ser Gly Ala Ile Pro Ile Phe Asp
            180                 185                 190

Asn Leu Lys Asn Gln Gly Ala Ile Ser Glu Pro Val Phe Ala Phe Tyr
        195                 200                 205

Leu Ser Lys Asn Lys Gln Glu Gly Ser Val Val Met Phe Gly Gly Val
    210                 215                 220

Asp His Gln Tyr Tyr Lys Gly Glu Leu Asn Trp Ile Pro Leu Ile Glu
225                 230                 235                 240

Ala Gly Glu Trp Arg Val His Met Asp Arg Ile Ser Met Lys Arg Thr
                245                 250                 255

Val Ile Ala Cys Ser Asp Gly Cys Glu Ala Leu Val His Thr Gly Thr
            260                 265                 270

Ser His Ile Glu Gly Pro Gly Arg Leu Val Asn Asn Ile His Arg Leu
        275                 280                 285

Ile Arg Thr Arg Pro Phe Asp Ser Lys His Tyr Val Ser Cys Phe Ala
    290                 295                 300

Thr Lys Tyr Leu Pro Ser Ile Thr Phe Ile Ile Asn Gly Ile Lys Tyr
305                 310                 315                 320

Pro Met Thr Ala Arg Ala Tyr Ile Phe Lys Asp Ser Arg Gly Arg Cys
                325                 330                 335

Tyr Ser Ala Phe Lys Glu Asn Thr Val Arg Ser Arg Ser Glu Thr Trp
            340                 345                 350

Ile Leu Gly Asp Ala Phe Leu Arg Arg Tyr Phe Ser Val Phe Asp Arg
        355                 360                 365

Gly Asn Asp Arg Ile Gly Leu Ala Arg Ala Val
    370                 375
```

<210> SEQ ID NO 56
<211> LENGTH: 379
<212> TYPE: PRT
<213> ORGANISM: Bos taurus

<400> SEQUENCE: 56

```
Met Lys Trp Ile Val Leu Leu Gly Leu Val Ala Phe Ser Glu Cys Ile
1               5                   10                  15

Val Lys Ile Pro Leu Arg Gln Val Lys Thr Met Arg Lys Thr Leu Ser
            20                  25                  30

Gly Lys Asn Met Leu Lys Asn Phe Leu Lys Glu His Pro Tyr Arg Leu
        35                  40                  45

Ser Gln Ile Ser Phe Arg Gly Ser Asn Leu Thr Ile His Pro Leu Arg
    50                  55                  60

Asn Ile Met Asn Leu Val Tyr Val Gly Asn Ile Thr Ile Gly Thr Pro
65                  70                  75                  80

Pro Gln Glu Phe Gln Val Val Phe Asp Thr Gly Ser Ser Asp Leu Trp
                85                  90                  95

Val Pro Ser Phe Cys Thr Met Pro Ala Cys Ser Ala Pro Val Trp Phe
            100                 105                 110

Arg Gln Leu Gln Ser Ser Thr Phe Gln Pro Thr Asn Lys Thr Phe Thr
        115                 120                 125

Ile Thr Tyr Gly Ser Gly Ser Met Lys Gly Phe Leu Ala Tyr Asp Thr
    130                 135                 140

Val Arg Ile Gly Asp Leu Val Ser Thr Asp Gln Pro Phe Gly Leu Ser
145                 150                 155                 160

Val Val Glu Tyr Gly Leu Glu Gly Arg Asn Tyr Asp Gly Val Leu Gly
                165                 170                 175

Leu Asn Tyr Pro Asn Ile Ser Phe Ser Gly Ala Ile Pro Ile Phe Asp
            180                 185                 190

Asn Leu Lys Asn Gln Gly Ala Ile Ser Glu Pro Val Phe Ala Phe Tyr
        195                 200                 205

Leu Ser Lys Asn Lys Gln Glu Gly Ser Val Val Met Phe Gly Gly Val
    210                 215                 220

Asp His Gln Tyr Tyr Lys Gly Glu Leu Asn Trp Ile Pro Leu Ile Glu
225                 230                 235                 240

Ala Gly Glu Trp Arg Val His Met Asp Arg Ile Ser Met Lys Arg Thr
                245                 250                 255

Val Ile Ala Cys Ser Asp Gly Cys Glu Ala Leu Val His Thr Gly Thr
            260                 265                 270

Ser His Ile Glu Gly Pro Gly Arg Leu Val Asn Asn Ile His Arg Leu
        275                 280                 285

Ile Arg Thr Arg Pro Phe Asp Ser Lys His Tyr Val Ser Cys Phe Ala
    290                 295                 300

Thr Lys Tyr Leu Pro Ser Ile Thr Phe Ile Ile Asn Gly Ile Lys Tyr
305                 310                 315                 320

Pro Met Thr Ala Arg Ala Tyr Ile Phe Lys Asp Ser Arg Gly Arg Cys
                325                 330                 335

Tyr Ser Ala Phe Lys Glu Asn Thr Val Arg Thr Ser Arg Glu Thr Trp
            340                 345                 350

Ile Leu Gly Asp Ala Phe Leu Arg Arg Tyr Phe Ser Val Phe Asp Arg
        355                 360                 365

Gly Asn Asp Arg Ile Gly Leu Ala Gln Ala Val
    370                 375
```

<210> SEQ ID NO 57
<211> LENGTH: 380
<212> TYPE: PRT
<213> ORGANISM: Bos taurus

<400> SEQUENCE: 57

```
Met Lys Trp Leu Val Leu Leu Gly Leu Val Ala Phe Ser Glu Cys Ile
1               5                   10                  15
Val Lys Ile Pro Leu Arg Arg Val Lys Thr Met Arg Lys Thr Leu Ser
            20                  25                  30
Gly Lys Asn Thr Leu Asn Asn Phe Leu Lys Glu His Pro Tyr Arg Leu
        35                  40                  45
Ser His Ile Ser Phe Arg Gly Ser Asn Leu Thr Thr Leu Pro Leu Arg
    50                  55                  60
Asn Ile Arg Asp Met Leu Tyr Val Gly Asn Ile Thr Ile Gly Thr Pro
65                  70                  75                  80
Pro Gln Glu Phe Gln Val Val Phe Asp Thr Gly Ser Ser Asp Leu Trp
                85                  90                  95
Val Pro Ser Asp Phe Cys Thr Ser Pro Ala Cys Ser Thr His Val Arg
            100                 105                 110
Phe Arg His Phe Gln Ser Ser Thr Phe Arg Pro Thr Thr Lys Thr Phe
        115                 120                 125
Arg Ile Ile Tyr Gly Ser Gly Arg Met Lys Gly Val Val Ala His Asp
    130                 135                 140
Thr Val Arg Ile Gly Asn Leu Val Ser Thr Asp Gln Pro Phe Gly Leu
145                 150                 155                 160
Ser Met Ala Glu Tyr Gly Leu Glu Ser Arg Arg Phe Asp Gly Ile Leu
                165                 170                 175
Gly Leu Asn Tyr Pro Asn Leu Ser Cys Ser Gly Ala Ile Pro Ile Phe
            180                 185                 190
Asp Lys Leu Lys Asn Gln Gly Ala Ile Ser Asp Pro Ile Phe Ala Phe
        195                 200                 205
Tyr Leu Ser Lys Asp Lys Arg Glu Gly Ser Val Val Met Phe Gly Gly
    210                 215                 220
Val Asp His Arg Tyr Tyr Lys Gly Glu Leu Asn Trp Val Pro Leu Ile
225                 230                 235                 240
Arg Ala Gly Asp Trp Ile Val His Val Asp Arg Ile Thr Met Lys Arg
                245                 250                 255
Glu Val Ile Ala Cys Ser Asp Gly Cys Ala Ala Leu Val Asp Thr Gly
            260                 265                 270
Thr Ser Leu Ile Gln Gly Pro Gly Arg Val Ile Asp Asn Ile His Lys
        275                 280                 285
Leu Ile Gly Ala Thr Pro Arg Gly Ser Lys His Tyr Val Ser Cys Ser
    290                 295                 300
Val Val Asn Thr Leu Pro Ser Ile Ile Phe Thr Ile Asn Gly Ile Asn
305                 310                 315                 320
Tyr Pro Val Pro Ala Pro Ala Tyr Ile Leu Lys Asp Ser Arg Gly Tyr
                325                 330                 335
Cys Tyr Thr Ala Phe Lys Glu Gln Arg Val Arg Arg Ser Thr Glu Ser
            340                 345                 350
Trp Leu Leu Gly Asp Val Phe Leu Arg Leu Tyr Phe Ser Val Phe Asp
        355                 360                 365
Arg Gly Asn Asp Arg Ile Gly Leu Ala Arg Ala Val
    370                 375                 380
```

<210> SEQ ID NO 58
<211> LENGTH: 380
<212> TYPE: PRT
<213> ORGANISM: Bos taurus

<400> SEQUENCE: 58

```
Met Lys Trp Leu Val Leu Leu Trp Leu Val Ala Phe Ser Glu Cys Ile
1               5                   10                  15

Val Lys Ile Pro Leu Arg Gln Val Lys Thr Met Arg Lys Thr Leu Ser
            20                  25                  30

Gly Lys Asn Thr Leu Asn Asn Phe Leu Lys Glu His Thr Tyr Ser Leu
        35                  40                  45

Ser Gln Ile Ser Ser Arg Gly Ser Asn Leu Thr Ile His Pro Leu Arg
    50                  55                  60

Asn Ile Met Asp Met Leu Tyr Val Gly Asn Ile Thr Ile Gly Thr Pro
65                  70                  75                  80

Pro Gln Glu Phe Gln Val Val Phe Asp Thr Gly Ser Ser Asp Leu Trp
                85                  90                  95

Val Pro Ser Val Phe Cys Gln Ser Leu Ala Cys Ala Thr Lys Val Met
            100                 105                 110

Phe Ile His Leu His Ser Ser Thr Phe Arg His Thr Gln Lys Val Phe
        115                 120                 125

Asn Ile Lys Tyr Asn Thr Gly Arg Met Lys Gly Leu Leu Val Tyr Asp
    130                 135                 140

Thr Val Arg Ile Gly Asp Leu Val Ser Thr Asp Gln Pro Phe Cys Ile
145                 150                 155                 160

Ser Leu Ala Glu Val Gly Phe Asp Gly Ile Pro Phe Asp Gly Val Leu
                165                 170                 175

Gly Leu Asn Tyr Pro Asn Met Ser Phe Ser Gly Ala Ile Pro Ile Phe
            180                 185                 190

Asp Asn Leu Lys Asn Glu Gly Ala Ile Ser Glu Pro Val Phe Ala Phe
        195                 200                 205

Tyr Leu Ser Lys Asp Lys Arg Glu Gly Ser Val Val Met Phe Gly Gly
    210                 215                 220

Val Asp His Arg Tyr Tyr Lys Gly Glu Leu Asn Trp Val Pro Leu Ile
225                 230                 235                 240

Gln Ala Gly Gly Trp Thr Val His Val Asp Arg Ile Ser Met Lys Arg
                245                 250                 255

Lys Ile Ile Ala Cys Ser Gly Gly Cys Glu Ala Leu Val Asp Thr Gly
            260                 265                 270

Thr Ala Leu Ile Lys Gly Pro Arg Arg Leu Val Asn Asn Ile Gln Lys
        275                 280                 285

Leu Ile Gly Thr Thr Pro Arg Gly Ser Lys His Tyr Val Ser Cys Ser
    290                 295                 300

Val Val Asn Thr Leu Pro Ser Ile Ile Phe Thr Ile Asn Gly Ile Asn
305                 310                 315                 320

Tyr Pro Val Pro Ala Arg Ala Tyr Ile Leu Lys Asp Ser Glu Ser Asn
                325                 330                 335

Cys Tyr Thr Thr Phe Lys Glu Asn Thr Val Arg Thr Ser Arg Glu Thr
            340                 345                 350

Trp Ile Leu Gly Asp Val Phe Pro Arg Leu Tyr Phe Ser Val Phe Asp
        355                 360                 365

Arg Gly Asn Asp Arg Ile Gly Leu Ala Arg Ala Val
    370                 375                 380

<210> SEQ ID NO 59
<211> LENGTH: 380
<212> TYPE: PRT
<213> ORGANISM: Bos taurus
```

-continued

```
<400> SEQUENCE: 59

Met Lys Trp Leu Val Leu Leu Trp Leu Val Ala Phe Ser Glu Cys Ile
1               5                   10                  15

Val Lys Ile Pro Leu Arg Gln Val Lys Thr Met Arg Lys Thr Leu Ser
            20                  25                  30

Gly Lys Asn Thr Leu Asn Asn Phe Leu Lys Glu His Thr Tyr Ser Leu
        35                  40                  45

Ser Gln Ile Ser Ser Arg Gly Ser Asn Leu Thr Ile His Pro Leu Arg
    50                  55                  60

Asn Ile Met Asp Met Leu Tyr Val Gly Asn Ile Thr Ile Gly Thr Pro
65                  70                  75                  80

Pro Gln Glu Phe Gln Val Val Phe Asp Thr Gly Ser Ser Asp Leu Trp
                85                  90                  95

Val Pro Ser Val Phe Cys Gln Ser Leu Ala Cys Ala Thr Lys Val Met
            100                 105                 110

Phe Ile His Leu Tyr Ser Ser Thr Phe Arg His Thr Gln Lys Val Phe
        115                 120                 125

Asn Ile Lys Tyr Asn Thr Gly Arg Met Lys Gly Leu Leu Val Tyr Asp
    130                 135                 140

Thr Val Arg Ile Gly Asp Leu Val Ser Thr Asp Gln Pro Phe Cys Ile
145                 150                 155                 160

Ser Leu Ala Glu Val Gly Phe Asp Gly Ile Pro Phe Asp Gly Val Leu
                165                 170                 175

Gly Leu Asn Tyr Pro Asn Met Ser Phe Ser Gly Ala Ile Pro Ile Phe
            180                 185                 190

Asp Asn Leu Lys Asn Glu Gly Ala Ile Ser Glu Pro Val Phe Ala Phe
        195                 200                 205

Tyr Leu Ser Lys Asp Lys Arg Glu Gly Ser Val Val Met Phe Gly Gly
    210                 215                 220

Val Asp His Arg Tyr Tyr Lys Gly Glu Leu Asn Trp Val Pro Leu Ile
225                 230                 235                 240

Gln Ala Gly Gly Trp Thr Val His Val Asp Arg Ile Ser Met Lys Arg
                245                 250                 255

Lys Ile Ile Ala Cys Ser Gly Gly Cys Glu Ala Leu Val Asp Thr Gly
            260                 265                 270

Thr Ala Leu Ile Lys Gly Pro Arg Arg Leu Val Asn Asn Ile Gln Lys
        275                 280                 285

Leu Ile Gly Thr Thr Pro Arg Gly Ser Lys His Tyr Val Ser Cys Ser
    290                 295                 300

Val Val Asn Thr Leu Pro Ser Ile Ile Phe Thr Ile Asn Gly Ile Asn
305                 310                 315                 320

Tyr Pro Val Pro Ala Arg Ala Tyr Ile Leu Lys Asp Ser Glu Ser His
                325                 330                 335

Cys Tyr Thr Ala Phe Lys Glu Asn Thr Val Arg Thr Ser Arg Glu Thr
            340                 345                 350

Trp Ile Leu Gly Asp Val Phe Leu Arg Leu Tyr Phe Ser Val Phe Asp
        355                 360                 365

Arg Gly Asn Asp Arg Ile Gly Leu Ala Arg Ala Val
    370                 375                 380

<210> SEQ ID NO 60
<211> LENGTH: 380
<212> TYPE: PRT
<213> ORGANISM: Bos taurus
```

<400> SEQUENCE: 60

```
Met Lys Trp Leu Val Val Leu Gly Leu Val Ala Phe Ser Glu Cys Ile
1               5                   10                  15

Val Lys Ile Pro Leu Arg Arg Val Lys Thr Met Arg Lys Ala Leu Ser
            20                  25                  30

Gly Lys Asn Met Leu Asn Asn Phe Leu Lys Glu His Ala Tyr Arg Leu
        35                  40                  45

Ser Gln Ile Ser Phe Arg Gly Ser Asn Leu Thr Ser His Pro Leu Arg
    50                  55                  60

Asn Ile Lys Asp Leu Val Tyr Leu Ala Asn Ile Thr Ile Gly Thr Pro
65                  70                  75                  80

Pro Gln Glu Phe Gln Val Phe Leu Asp Thr Gly Ser Ser Asp Leu Trp
                85                  90                  95

Val Pro Ser Asp Phe Cys Thr Ser Pro Gly Cys Ser Lys His Val Arg
            100                 105                 110

Phe Arg His Leu Gln Ser Ser Thr Phe Arg Leu Thr Asn Lys Thr Phe
        115                 120                 125

Ser Ile Thr Tyr Gly Ser Gly Arg Ile Lys Gly Val Val Ala His Asp
    130                 135                 140

Thr Val Arg Ile Gly Asp Leu Val Ser Thr Asp Gln Pro Phe Ser Leu
145                 150                 155                 160

Ser Met Ala Glu Tyr Gly Leu Glu His Ile Pro Phe Asp Gly Ile Leu
                165                 170                 175

Gly Leu Asn Tyr Pro Asn Val Ser Ser Ser Gly Ala Ile Pro Ile Phe
            180                 185                 190

Asp Lys Leu Lys Asn Gln Gly Ala Ile Ser Glu Pro Val Phe Ala Phe
        195                 200                 205

Tyr Leu Ser Lys Asp Lys Gln Glu Gly Ser Val Val Met Phe Gly Gly
    210                 215                 220

Val Asp His Arg Tyr Tyr Arg Gly Lys Leu Asn Trp Val Pro Leu Ile
225                 230                 235                 240

Gln Ala Gly Asn Trp Ile Ile His Met Asp Ser Ile Ser Ile Glu Arg
                245                 250                 255

Lys Val Ile Ala Cys Ser Gly Gly Cys Val Ala Phe Val Asp Ile Gly
            260                 265                 270

Thr Ala Phe Ile Glu Gly Pro Lys Pro Leu Val Asp Asn Met Gln Lys
        275                 280                 285

Leu Ile Arg Ala Lys Pro Trp Arg Ser Lys His Tyr Val Ser Cys Ser
    290                 295                 300

Ala Val Asn Thr Leu Pro Ser Ile Thr Phe Thr Ile Asn Gly Ile Asn
305                 310                 315                 320

Tyr Pro Val Pro Gly Arg Ala Tyr Ile Leu Lys Asp Ser Arg Arg Arg
                325                 330                 335

Cys Tyr Ser Thr Phe Lys Glu Ile Pro Leu Ser Pro Thr Thr Glu Phe
            340                 345                 350

Trp Met Leu Gly Asp Val Phe Leu Arg Leu Tyr Phe Ser Val Phe Asp
        355                 360                 365

Arg Gly Asn Asp Arg Ile Gly Leu Ala Arg Ala Val
    370                 375                 380

<210> SEQ ID NO 61
<211> LENGTH: 380
<212> TYPE: PRT
<213> ORGANISM: Bos taurus
```

<400> SEQUENCE: 61

```
Met Lys Trp Leu Val Leu Leu Gly Leu Val Ala Phe Ser Glu Cys Ile
1               5                   10                  15

Phe Lys Ile Pro Leu Arg Arg Val Lys Thr Met Arg Lys Thr Leu Ser
            20                  25                  30

Gly Lys Asn Met Leu Asn Asn Phe Leu Lys Glu His Pro Tyr Lys Leu
        35                  40                  45

Ser Gln Ile Ser Phe Arg Gly Ser Asn Leu Thr Thr Leu Pro Leu Arg
    50                  55                  60

Asn Ile Trp Asp Ile Phe Tyr Ile Gly Thr Ile Thr Ile Gly Thr Pro
65                  70                  75                  80

Pro Gln Glu Phe Gln Val Val Phe Asp Thr Ala Ser Ser Asp Leu Trp
                85                  90                  95

Val Pro Ser Ile Ile Cys Asn Ser Ser Thr Cys Ser Thr His Val Arg
            100                 105                 110

Phe Arg His Arg Gln Ser Ser Thr Phe Arg Leu Thr Asn Lys Thr Phe
            115                 120                 125

Gly Ile Thr Tyr Gly Ser Gly Arg Met Lys Gly Val Val His Asp
        130                 135                 140

Thr Val Arg Ile Gly Asp Leu Val Ser Thr Asp Gln Pro Phe Gly Leu
145                 150                 155                 160

Ser Val Ala Glu Tyr Gly Phe Glu Gly Arg Arg Phe Asp Gly Val Leu
                165                 170                 175

Gly Leu Asn Tyr Pro Asn Ile Ser Phe Ser Lys Ala Ile Pro Ile Phe
            180                 185                 190

Asp Lys Leu Lys Asn Glu Gly Ala Ile Ser Glu Pro Val Phe Ala Phe
            195                 200                 205

Tyr Leu Ser Lys Asp Lys Gln Lys Gly Ser Val Val Met Phe Gly Gly
210                 215                 220

Val Asp His Arg Tyr Tyr Lys Gly Glu Leu Asn Trp Val Pro Leu Ile
225                 230                 235                 240

Arg Ala Gly Asp Trp Ser Val His Val Asp Arg Ile Thr Met Lys Gly
                245                 250                 255

Glu Val Ile Gly Cys Ser Asp Gly Cys Thr Ala Met Val Asp Thr Gly
            260                 265                 270

Ser Ser Asn Ile Gln Gly Pro Gly Arg Val Ile Asp Asn Ile His Lys
            275                 280                 285

Leu Ile Gly Ala Thr Pro Arg Gly Ser Lys His Tyr Val Ser Cys Ser
    290                 295                 300

Ala Val Ser Ala Leu Pro Ser Val Val Phe Thr Ile Asn Gly Ile Asn
305                 310                 315                 320

Tyr Pro Val Pro Ala Arg Ala Tyr Val Leu Lys Asp Phe Thr Gly Asn
                325                 330                 335

Cys Tyr Thr Thr Phe Lys Glu Lys Arg Val Arg Arg Ser Thr Glu Phe
            340                 345                 350

Trp Ile Leu Gly Glu Ala Phe Leu Arg Leu Tyr Phe Ser Val Phe Asp
            355                 360                 365

Arg Gly Asn Asp Arg Ile Gly Leu Ala Arg Ala Val
370                 375                 380
```

<210> SEQ ID NO 62
<211> LENGTH: 380
<212> TYPE: PRT
<213> ORGANISM: Bos taurus

<400> SEQUENCE: 62

```
Met Lys Trp Val Val Leu Leu Gly Leu Val Ala Phe Ser Glu Cys Ile
1               5                   10                  15
Val Lys Ile Pro Leu Arg Arg Val Lys Thr Met Arg Lys Thr Leu Ser
            20                  25                  30
Gly Lys Asn Met Leu Asn Asn Phe Leu Lys Glu His Gly Asn Arg Leu
        35                  40                  45
Ser Lys Ile Ser Phe Arg Gly Ser Asn Leu Thr Thr Leu Pro Leu Arg
    50                  55                  60
Asn Ile Glu Asp Leu Met Tyr Val Gly Asn Ile Thr Ile Gly Thr Pro
65                  70                  75                  80
Pro Gln Glu Phe Gln Val Val Phe Asp Thr Gly Ser Ser Asp Phe Trp
                85                  90                  95
Val Pro Ser Asp Phe Cys Thr Ser Pro Asp Cys Ile Thr His Val Arg
            100                 105                 110
Phe Arg Gln His Gln Ser Ser Thr Phe Arg Pro Thr Asn Lys Thr Phe
        115                 120                 125
Ser Ile Thr Tyr Gly Ser Gly Arg Met Arg Gly Val Val His Asp
    130                 135                 140
Thr Val Arg Ile Gly Asp Leu Val Ser Thr Asp Gln Pro Phe Gly Leu
145                 150                 155                 160
Ser Val Ser Glu Tyr Gly Phe Lys Asp Arg Ala Tyr Asp Gly Ile Leu
                165                 170                 175
Gly Leu Asn Tyr Pro Asp Glu Ser Phe Ser Glu Ala Ile Pro Ile Phe
            180                 185                 190
Asp Lys Leu Lys Asn Glu Gly Ala Ile Ser Glu Pro Ile Phe Ala Phe
        195                 200                 205
Tyr Leu Ser Lys Lys Arg Glu Gly Ser Val Val Met Phe Gly Gly
    210                 215                 220
Val Asp His Arg Tyr Tyr Lys Gly Glu Leu Asn Trp Val Pro Leu Ile
225                 230                 235                 240
Glu Glu Gly Asp Trp Ser Val Arg Met Asp Gly Ile Ser Met Lys Thr
                245                 250                 255
Lys Val Val Ala Cys Ser Asp Gly Cys Glu Ala Val Val Asp Thr Gly
            260                 265                 270
Thr Ser Leu Ile Lys Gly Pro Arg Lys Leu Val Asn Lys Ile Gln Lys
        275                 280                 285
Leu Ile Gly Ala Thr Pro Arg Gly Ser Lys His Tyr Val Tyr Cys Ser
    290                 295                 300
Ala Val Asn Ala Leu Pro Ser Ile Ile Phe Thr Ile Asn Gly Ile Asn
305                 310                 315                 320
Tyr Pro Val Pro Ala Arg Ala Tyr Ile Leu Lys Asp Ser Arg Gly Arg
                325                 330                 335
Cys Tyr Thr Ala Phe Lys Lys Gln Arg Phe Ser Ser Ser Thr Glu Thr
            340                 345                 350
Trp Leu Leu Gly Asp Ala Phe Leu Arg Val Tyr Phe Ser Val Phe Asp
        355                 360                 365
Arg Gly Asn Gly Arg Ile Gly Leu Ala Gln Ala Val
    370                 375                 380
```

<210> SEQ ID NO 63
<211> LENGTH: 15
<212> TYPE: PRT
<213> ORGANISM: Bos taurus

```
<400> SEQUENCE: 63

Arg Glu Gly Ser Val Val Met Phe Gly Val Asp His Arg Tyr
1               5                   10                  15

<210> SEQ ID NO 64
<211> LENGTH: 10
<212> TYPE: PRT
<213> ORGANISM: Bos taurus

<400> SEQUENCE: 64

Arg Leu Tyr Phe Ser Val Phe Asp Arg Gly
1               5                   10

<210> SEQ ID NO 65
<211> LENGTH: 16
<212> TYPE: PRT
<213> ORGANISM: Bos taurus

<400> SEQUENCE: 65

Asn Gln Gly Ala Ile Ser Asp Pro Ile Phe Ala Phe Tyr Leu Ser Lys
1               5                   10                  15

<210> SEQ ID NO 66
<211> LENGTH: 15
<212> TYPE: PRT
<213> ORGANISM: Bos taurus

<400> SEQUENCE: 66

Arg Glu Gly Ser Val Val Met Phe Gly Val Asp His Arg Tyr
1               5                   10                  15

<210> SEQ ID NO 67
<211> LENGTH: 11
<212> TYPE: PRT
<213> ORGANISM: Bos taurus

<400> SEQUENCE: 67

Lys Gly Leu Leu Val Tyr Asp Thr Val Arg Ile
1               5                   10

<210> SEQ ID NO 68
<211> LENGTH: 10
<212> TYPE: PRT
<213> ORGANISM: Bos taurus

<400> SEQUENCE: 68

Arg Leu Tyr Phe Ser Val Phe Asp Arg Gly
1               5                   10

<210> SEQ ID NO 69
<211> LENGTH: 18
<212> TYPE: PRT
<213> ORGANISM: Bos taurus

<400> SEQUENCE: 69

Lys Asn Glu Gly Ala Ile Ser Glu Pro Val Phe Ala Phe Tyr Leu Ser
1               5                   10                  15

Lys Asp

<210> SEQ ID NO 70
<211> LENGTH: 18
<212> TYPE: PRT
<213> ORGANISM: Bos taurus

<400> SEQUENCE: 70
```

```
Lys Asp Lys Gln Glu Gly Ser Val Val Met Phe Gly Gly Val Asp His
1               5                   10                  15

Arg Tyr

<210> SEQ ID NO 71
<211> LENGTH: 12
<212> TYPE: PRT
<213> ORGANISM: Bos taurus

<400> SEQUENCE: 71

Lys Thr Phe Ser Ile Thr Tyr Gly Ser Gly Arg Ile
1               5                   10

<210> SEQ ID NO 72
<211> LENGTH: 19
<212> TYPE: PRT
<213> ORGANISM: Bos taurus

<400> SEQUENCE: 72

Asp Lys Gln Glu Gly Ser Val Val Met Phe Gly Gly Val Asp His Arg
1               5                   10                  15

Tyr Tyr Arg

<210> SEQ ID NO 73
<211> LENGTH: 10
<212> TYPE: PRT
<213> ORGANISM: Bos taurus

<400> SEQUENCE: 73

Arg Leu Tyr Phe Ser Val Phe Asp Arg Gly
1               5                   10

<210> SEQ ID NO 74
<211> LENGTH: 18
<212> TYPE: PRT
<213> ORGANISM: Bos taurus

<400> SEQUENCE: 74

Lys Asn Gln Gly Ala Ile Ser Glu Pro Val Phe Ala Phe Tyr Leu Ser
1               5                   10                  15

Lys Asp
```

COMPOSITIONS AND METHODS FOR EARLY PREGNANCY DIAGNOSIS

CROSS REFERENCE TO RELATED APPLICATION

This application claims the priority of U.S. provisional application Ser. No. 61/013,603 (filed Dec. 13, 2007), the entire disclosure of which is incorporated herein by reference.

BACKGROUND OF THE INVENTION

I. Field of the Invention

The present invention relates generally to the fields of veterinary medicine, reproductive biology and diagnostics. More specifically, the present invention relates to methods and compositions for detecting early stage pregnancy.

II. Related Art

Pregnancy diagnosis allows for sound reproductive management in the dairy and beef industry. In general, artificial insemination is successful less than 50% of the time and the producer must either rely on overt signs of return to estrus (that are easily missed) or delay rebreeding until pregnancy failure is confirmed by one of the methods described above. Such delays are extremely costly and constitute a major economic loss to the industry.

An accurate pregnancy test for cattle which can be performed early and which has low false positives has long been sought. Several pregnancy tests are available, including a milk progesterone assay (Oltenacu et al., 1990; Markusfeld et al., 1990), estrone sulfate analysis (Holdsworth et al., 1982; Warnick et al., 1995), rectal palpation (Hatzidakis et al., 1993), ultrasound (Beal et al., 1992; Cameron and Malmo, 1993), and blood tests for pregnancy-specific antigens.

Each of these procedures has fallen short of expectations in terms of their practical, on-farm use. For example, measurements of milk or serum progesterone around day 18-22 yield unacceptably high rates of false positives (Oltenacu et al., 1990; Markusfeld et al., 1990). Rectal palpation can be used to detect pregnancy as early as day 35, but this procedure can lead to 5-10% or greater embryonic mortality (Oltenacu et al., 1990; Hatzidakis et al., 1993). Rectal palpation on day 50 causes less damage to the embryos, but has only marginal economic value because of its lateness (Oltenacu et al., 1990). Ultrasonography has an advantage over rectal palpation in accuracy, particularly before day 45 (Beal et al., 1992; Cameron and Malmo, 1993), but the instrument is expensive, its use requires considerable training, and there is a finite risk to the animal. A related procedure, Doppler sonography, is more accurate than rectal palpation (Cameron and Malmo, 1993), but again requires well trained personnel. The presence of estrone sulfate in urine or serum provides another test but is only useful after day 100 as concentrations rise (Holdsworth et al., 1982; Warnick et al., 1995).

The discovery of pregnancy-specific protein B (PSP-B) (Butler et al., 1982) provided a new approach to pregnancy diagnosis since it could be detected in the blood of pregnant cows by the fourth week of pregnancy (Sasser et al., 1986; Humblot et al., 1988). Others have developed immunoassays that may be based on an identical or immunologically similar antigen (Zoli et al., 1992a; Mialon et al., 1993; Mialon et al., 1994). In one case, the antigen (Mr ~67 kDa) was called bovine pregnancy-associated glycoprotein (boPAG; now boPAG-1) (Zoli et al., 1992a); in the second, it was designated as pregnancy serum protein 60 (PSP60) (Mialon et al., 1993; Mialon et al., 1994). The immunoassays for PSP-B/boPAG1/PSP60 have certain disadvantages. First, positive diagnosis in the fourth week of pregnancy remains somewhat uncertain because antigen concentrations in blood are low and somewhat variable. Second, boPAG1 concentrations rise markedly at term (Sasser et al., 1986; Zoli et al., 1992a; Mialon et al., 1993) and, due to the long circulating half-life of the molecule (Kiracofe et al., 1993), the antigen can still be detected 80-100 day postpartum (Zoli et al., 1992a; Mialon et al., 1993; Mialon et al., 1994; Kiracofe et al., 1993), compromising pregnancy diagnosis in cows bred within the early postpartum period. Thus, the test can be carried out in dairy cows at day 30 only if artificial insemination ("AI") is performed at or after 70 day post-partum.

Pregnancy-associated glycoproteins (PAGs) are structurally related to the pepsins. They are thought to be restricted to the hooved (ungulate) mammals and characterized by being expressed specifically in the outer epithelial cell layer (chorion/trophectoderm) of the placenta (Green et al., 2000; Hughes et al., 2003; Xie et al., 1997). At least some PAGs are catalytically inactive as proteinases, although each appears to possess a cleft capable of binding peptides (Guruprasad et al., 1996). It is estimated that cattle, sheep, and most probably all ruminant Artiodactyla possess dozens of PAG genes. The PAGs are highly diverse in sequence, with regions of hypervariability confined largely to surface-exposed loops.

Bovine pregnancy-associated glycoproteins (boPAGs/PSPB/PSP60) were discovered in attempts to develop pregnancy tests for livestock (Butler et al., 1982; Sasser et al., 1986; Zoli et al., 1991; Zoli et al., 1992a). In each attempt, rabbits were injected with extracts of placental cotyledons, and antibodies not directed against placental antigens were removed by adsorption with tissue extracts from non-pregnant animals. The resulting antisera provided the basis of an accurate pregnancy test for cattle and sheep as early as one month post-insemination.

Even in initial studies (Butler et al., 1982; Zoli et al., 1991; Xie et al., 1991; Xie et al., 1994; Xie et al., 1996), it was clear that the boPAGs were heterogeneous in molecular weight and charge, and as more isoforms have been purified it has become evident that they differ in their amino terminal sequences (Atkinson et al., 1993; Xie et al., 1997a). Further library screening has revealed additional transcripts in ruminants (Xie et al., 1994; Xie et al., 1995; Xie et al., 1997b) and the existence of PAGs in non-ruminant species such as the pig (Szafranska et al., 1995). PAG-like proteins (also known as 'pepsinogen F' or 'pepsin F') have been described in the horse and cat (Green et al., 1999; Guruprasad et al., 1996). Among the bovine PAGs that have been described are boPAG2, boPAG4, boPAG5, boPAG6, boPAG7, boPAG9, boPAG7v; boPAG9v; boPAG15; boPAG16; boPAG17; boPAG18; boPAG19; boPAG20 and boPAG21 (U.S. Pat. No. 6,869,770). Information regarding methods for diagnosing early pregnancy by assaying for such PAGs can be found, for example, in U.S. Pat. No. 6,869,770 and U.S. Patent App. Pub. No. 20050100975.

Most of the available tests for detecting pregnancy in cattle are less accurate prior to day 30 following breeding. Further, for many of the existing tests, skilled personnel are required. Thus, there is the need for an accurate and sensitive pregnancy test in cattle that can be performed quickly and easily prior to day 30 following breeding.

SUMMARY OF THE INVENTION

Therefore, one aspect of the present invention provides a sensitive and accurate test for early pregnancy. The present invention provides in one embodiment an early pregnancy test in which a specific polypeptide that includes a domain that is highly specific for a PAG can be detected with a high degree of sensitivity and specificity prior to the end of the fourth week of pregnancy. The ability to diagnose pregnancy at such an early stage is particularly useful in the dairy industry where animals are usually confined for at least part of the day and where intensive management is practiced. Further, embodiments of the present invention will find use in breeding programs for other animals.

In another aspect, the invention provides methods for detecting pregnancy in an animal comprising: (a) obtaining a sample from the animal; (b) contacting the sample with an antibody or antibody fragment, wherein the antibody or antibody fragment comprises a 2D9 antibody or fragment or variant thereof; and (c) detecting contacting of the antibody or antibody fragment with at least one pregnancy associated antigen (PAG) in the sample, wherein detection of the PAG indicates that the animal is pregnant. In one embodiment, an antibody used comprises a domain having greater than 97% sequence identity to SEQ ID NO:1 or greater than 92% sequence identity to SEQ ID NO:2. In some embodiments, the animal is a member of the suborder Ruminantia. In specific embodiments, the Ruminantian is a member of the family Bovidae. In other embodiments, the animal is a goat, a sheep, a member of the order Perissodactyla, a horse, a rhinoceros, a canine, a feline species, a human, or a panda.

A hybridoma cell line that produces 2D9 was deposited with the Patent Depository of the American Type Culture Collection (ATCC), Manassas, Va., 20110-2209 on Aug. 2, 2007 and assigned Patent Deposit No. PTA-8566 (Identification Reference MON-PAG-2D9). The deposit will be maintained under the terms of the Budapest Treaty on the International Recognition of the Deposit of Microorganisms for the Purposes of Patent Procedure. This deposit was made merely as a convenience for those of skill in the art and are not an admission that a deposit is required under 35 U.S.C. §112.

In certain embodiments, the domain has 98% or more sequence identity to SEQ ID NO:1, including 99% or more sequence identity to SEQ ID NO:1. In further embodiments, the domain comprises SEQ ID NO:1.

In some embodiments, the domain has 92% or more sequence identity to SEQ ID NO:2, including at least 93%, 94%, 95%, 96%, 97%, 98%, and 99% or more sequence identity to SEQ ID NO:2. In some specific embodiments, the domain comprises SEQ ID NO:2.

In some embodiments, the antibody or antibody fragment is further defined as an antibody comprising at least one light chain and at least one heavy chain. In specific embodiments, the light chain may have greater than 97% sequence identity to SEQ ID NO:1. In further embodiments, the heavy chain has greater than 95% sequence identity with SEQ ID NO:2. In more particular embodiments, the heavy chain has greater than 98% sequence identity with SEQ ID NO:2. In other embodiments, the heavy chain comprises SEQ ID NO:2.

In some other particular embodiments, the antibody comprises a light chain comprising SEQ ID NO:3 and a heavy chain comprising SEQ ID NO:4.

The antibody may be a monoclonal antibody or a polyclonal antibody. In one embodiment, the antibody is monoclonal antibody 2D9.

The PAG detected can be any PAG, such as boPAG4, boPAG6, boPAG9, boPAG16, boPAG17, boPAG19, boPAG20, and boPAG21. In one embodiment, the PAG is boPAG6.

In further embodiments, the invention pertains to methods for detecting pregnancy in a bovine animal comprising: (a) obtaining a sample from the animal; (b) contacting the sample with an 2D9 monoclonal antibody, and (c) detecting contacting of the antibody with one or more of boPAG4, boPAG6, boPAG9, boPAG16, boPAG17, boPAG19, boPAG20 or boPAG21 in the sample, wherein detection of the PAG(s) indicates that the animal is pregnant. The method for detecting pregnancy, for example, can be performed on day 15, 16, 17, 18, 19, 20, 21, 22, 23, 24, 25, 26, 27, 28, 29, 30, or more following artificial insemination.

A sample may be any sample known or suspected of containing a PAG. In specific embodiments, the sample is saliva, serum, plasma, blood, milk or urine. Any effective amount of sample can be obtained from the animal. For example, the amount may be about 5 µl, 10 µl, 15 µl, 20 µl, 25 µl, 30 µl, 40 µl, 50 µl, 60 µl, 70 µl, 80 µl, 90 µl, 100 µl, 150 µl, 200 µl, 250 µl, 300 µl, 350 µl, 400 µl, 450 µl, 500 µl, 550 µl, 600 µl, 700 µl, 800 µl, 900 µl, 1 ml, 1.5 ml, 2.0 ml, 2.5 ml, 3.0 ml, 3.5 ml, 4.0 ml, 4.5 ml, 5.0 ml, or more.

Any method of detecting contacting of the antibody or antibody fragment with a PAG that is known to those of ordinary skill in the art is contemplated by the methods of the present invention. For example, the method may comprise ELISA or Western blot. In particular embodiments, the PAG to be detected is boPAG2, boPAG4, boPAG5, boPAG6, boPAG7, boPAG9, boPAG7v, boPAG9v, boPAG15, boPAG16, boPAG17, boPAG18, boPAG19, boPAG20, or boPAG21. In specific embodiments, the PAG is boPAG6. In some embodiments of the present methods, more than one PAG in each sample is detected. When applied to species other than cattle, the present invention will allow detection of other PAGs produced at the time the trophoblast (pre-placenta) begins either to attach or to implant into the uterine wall of the mother. The "early" PAGs in these species may cross-react immunologically with the PAGs useful in detecting early pregnancy in cattle.

In particular embodiments, the ELISA is a sandwich ELISA comprising binding of a PAG to the antibody or antibody fragment fixed to a substrate and a second antibody preparation labeled with an enzyme. For example, the substrate to which the antibody or antibody fragment is fixed may be a tube, a well, a vial, a strip, a dipstick, or a biosensor. The enzyme, for example, may be alkaline phosphatase or horseradish peroxidase or any enzyme tag.

The present invention also generally pertains to an isolated and purified polypeptide encoded by a domain having greater than 97% sequence identity to SEQ ID NO:1 or greater than 92% sequence identity to SEQ ID NO:2. In particular embodiments, the domain comprises greater than 98% sequence identity to SEQ ID NO:1. In more particular embodiments, the domain comprises SEQ ID NO:1. There may be one or more additional amino acid residues attached to either the N-terminus or the C-terminus of the domain. In a particular embodiment, the polypeptide is SEQ ID NO:1. In some embodiments, the domain comprises greater than 95% sequence identity to SEQ ID NO:2. In more particular embodiments, the domain comprises greater than 98% sequence identity to SEQ ID NO:2. In a further particular embodiment, the polypeptide is SEQ ID NO:2. In other embodiments, the polypeptide comprises SEQ ID NO:3. In further embodiments, the polypeptide comprises SEQ ID NO:4.

The present invention also includes isolated and purified polynucleotides that encode a polypeptide that has a domain having greater than 97% sequence identity to SEQ ID NO:1 or greater than 92% sequence identity to SEQ ID NO:2. In some embodiments, the polynucleotide encodes a polypeptide having greater than 98% sequence identity to SEQ ID NO:1. In particular embodiments, polynucleotide encodes SEQ ID NO:1. In some embodiments, the polynucleotide encodes a polypeptide comprising a domain having greater than 95% sequence identity to SEQ ID NO:2. In more particular embodiments, the polynucleotide encodes a polypeptide having a domain that has greater than 98% sequence identity to SEQ ID NO:2. In more particular embodiments, the polynucleotide encodes a polypeptide comprising SEQ ID NO:2. In some embodiments, the polynucleotide comprises a nucleic acid sequence having greater than 98% identity to SEQ ID NO:5 or greater than 95% identity to SEQ ID NO:6. In some particular embodiments, the polynucleotide is SEQ ID NO:5, and in further particular embodiments, the polynucleotide is SEQ ID NO:6.

The present invention also generally pertains to a hybridoma cell that secretes monoclonal antibody 2D9.

The present invention also pertains to kits for detecting the presence of a PAG in an animal, wherein the kit includes an antibody or antibody fragment. In some embodiments, the antibody or antibody fragment comprises a light chain that comprises SEQ ID NO:3. In further embodiments, the antibody or antibody fragment comprises a heavy chain that comprises SEQ ID NO:4. In one embodiment, the antibody or antibody fragment is attached to a support. For example, the support may be a polystyrene plate, test tube, a strip, a dipstick, or a biosensor.

In some embodiments, the kit further includes a detectable label. For example, the detectable label may be a fluorescent tag attached to the antibody or antibody fragment. In other embodiments, the detectable label is a chemiluminescent tag. In further embodiments, the detectable label is an enzyme, such as alkaline phosphatase or horseradish peroxidase. The kit may further include a substrate for the enzyme. In further embodiments, the kit includes a buffer or diluent. The kit may also optionally include disposable pipettes. Other kit components, including reagent reservoirs, instructions and the like are well known to those of skill in the art and also are contemplated for use in the kits described herein.

The present invention also generally pertains to methods for detecting pregnancy in an animal comprising: (a) obtaining a sample from the animal; (b) contacting the sample with an antibody or antibody fragment provided by the invention; and (c) detecting a PAG in the sample by contacting it with the antibody or antibody fragment, wherein detection of one or more of boPAG4, boPAG6, boPAG9, boPAG16, boPAG17, boPAG19, boPAG20 or boPAG21, including all possible combinations thereof, indicates that the animal is pregnant.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Nucleic acid sequence of 2D9 light chain (SEQ ID NO:5). The start codon of the processed form (N-terminal amino acid) and the stop codon are indicated in bold.

FIG. 2. Nucleic acid sequence of 2D9 heavy chain (SEQ ID NO:6). The start codon of the processed form (N-terminal amino acid) and the stop codon are indicated in bold.

FIG. 3A, 3B. FIG. 3A—Peptide sequences of boPAG6 (top panel) and peptide sequences (bottom panel) identified in LC-MS-MS analysis (SEQ ID NOs:7-18) showed that PAGs eluted from 2D9-coated magnetic beads after immunoprecipitation of PAG enriched preparation mainly correspond to boPAG6. In order to identify all 2D9-binding components, an immuno-affinity chromatography purification of PAG enriched preparation was performed. The immuno-affinity column purified material was subjected to LC-MS-MS analysis. This analysis revealed that boPAG6 is the major 2D9 binding PAG and boPAG-4, boPAG-9, boPAG-20 and boPAG21 are minor 2D9 binding PAGs. FIG. 3B—Denaturing gel electrophoresis (SDS-PAGE) and Western blot analysis of PAGs purified from 2D9-immuno affinity chromatography of tissue extract prepared from day 55 bovine placenta. Both Coomassie stained gel and Western blot analysis with PAG polyclonal antibodies showed three protein bands at 67 kD, 55 kD and 50 kD as 2D9-binding PAGs. "Mz"=mass to charge ratio: peptide mass to charge of ionized peptide, minus water; "Charge"=ion charge state; "Mr(calc)"=peptide calculated molecular weight; "Start"=start amino acid of the protein that peptide aligns with; "End"=stop amino acid of the protein that peptide aligns with; "Score"=measure of peptide sequence confidence.

FIG. 6. The tables set forth show the accuracy of day 28 pregnancy diagnosis by using a lab-based ELISA compared to pregnancy diagnosis on day 28 ultrasound in two study sites, Wisconsin and California. Economics of a day 28 pregnancy test in dairy cow reproduction management was examined in this beta study. A lab-based PAG ELISA with polyclonal antibodies was used for pregnancy diagnosis. Wisconsin site used strictly synchronized breeding while California site used synchronized breeding plus breeding to heat. Approximately 1000 cows were used in the study per site. Blood samples were collected on day 28, shipped to lab for pregnancy testing. The results were returned to farms within 24 hrs to enable breeding decisions. Pregnancy status was also determined by ultrasound at the time of blood collection on day 28.

FIG. 7. Analysis results of breeding parameters in Wisconsin site trial. This site used a strictly synchronized breeding program with a day 28 pregnancy test (early resynch group) or with day 45 palpation (control group, late resynch). Results show a significant reduction in days between insemination and days open in the early resynch group (day 28 pregnancy test) compared to late resynch group (control group).

FIG. 8. Analysis results of breeding parameters in California site trial. This site used synchronized breeding plus breeding to heat with (early resynch group) and without (late resynch group) day 28 pregnancy test. Results show a significant reduction in days between insemination, number of inseminations and days open compared to late resynch group.

FIG. 10. Results of bovine pregnancy diagnosis performed with whole blood samples in the color test. The results are visually read. Tubes showing blue color reaction solution (tubes 1, 3, 6, 9, 10, 14 and 15) are positive result for pregnancy status and tubes showing clear background (tubes 2, 4, 5, 7, 8, 11, 12, 13 and 16) are negative (non-pregnant) for pregnancy status. For reading in a spectrophotometer, equal volume (0.4 ml) of stop solution (1N HCl) may be added to each tube. Addition of stop solution will turn the color to yellow. Then, the optical densities (OD) of each sample can be measured in a spectrophotometer at 630 nm.

FIG. 11A—Day 28 plasma panel. FIG. 11B—Day 55 plasma panel. All open cow samples in the day 28 and day 55 test panels produced a color intensity of 0.2 OD or less while pregnant plasma samples produced color intensity as high as 1.0 OD unit. In this assay, day 28 plasma samples showed a 100% sensitivity and 100% specificity when 0.2 OD color intensity was set as a cut-off. At the same color intensity cut-off, the day 55 plasma samples showed 95% sensitivity and 100% specificity in the plastic tube assay.

FIG. 12. Comparison of pregnancy testing of fresh plasma samples with PAG sandwich ELISA performed with polyclonal antibodies (Poly:Poly, top panel) and 2D9 monoclonal antibody and poly clonal antibody (Mono:Poly, bottom panel). Note a clear separation of open cow samples easily distinguished by using 0.2 OD cut-off color intensity. All pregnant cow samples had color intensity>0.2 OD units. The Mono:Poly assay had 100% sensitivity and 100% specificity in this experiment.

FIG. 14. Field testing results of color test compared to ultrasound results of 54 samples. The test identified all pregnant cows (100% sensitivity) with one false positive result compared to ultrasound results. There were 2 samples with inconclusive results in the color test later found to be 'open' cows. However, the color test identified 37 of 40 open cows (92.5% specificity) compared to ultrasound.

FIG. 16. Direct alignment of PAG isoforms 1, 4, 6, 9, 16, 17, 19, 20, and 21. Protein sequences for PAG isoforms and variants are given in SEQ ID NOs:51-62, derived from UniProt accessions Q29432, O46492, O46494, A5PJW4, O46497, A4FV16, Q9TTV8, Q9TTV7, A7MBA4, Q9TTV5, Q9TTV4, and Q9TTV3.

DETAILED DESCRIPTION OF ILLUSTRATIVE EMBODIMENTS

Figure 3B:
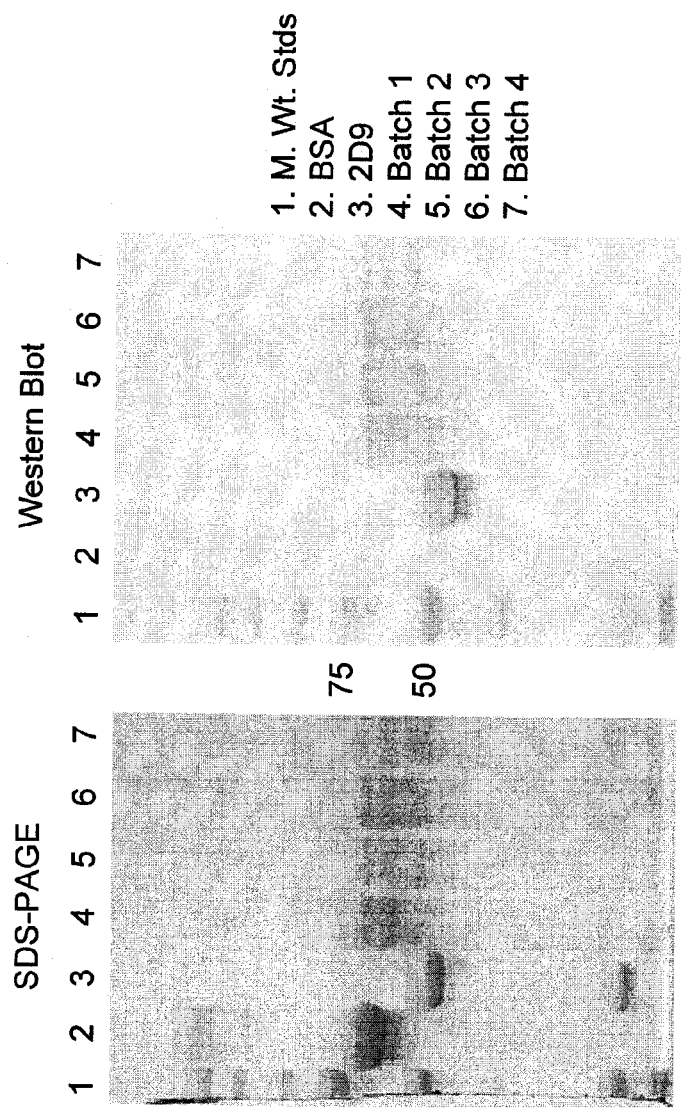

Despite the availability of several assays to detect pregnancy, there remains a need to provide improved assays for accurate and early detection of pregnancy, especially in cattle that are bred within two to three months postpartum or earlier. Certain embodiments of the present invention pertain to methods of determining pregnancy status of a cow by performing a color test to measure binding of a PAG in a sample obtained from the animal with a polypeptide, such as monoclonal antibody 2D9, an antibody which binds to PAGs indicative of bovine pregnancy. The color test can be performed early, such as 26 days following insemination. The color test can be used in any of a variety of formats, such as with test tubes or ELISA plates. In particular embodiments, the test utilizes a sandwich immunoassay principle that uses a second antibody. A color, such as a blue color, indicates a positive test, while tubes that are clear indicate a negative test. Embodiments of the present methods can be performed easily prior to 30 days following artificial insemination, and are highly sensitive and specific. Further, multiple samples can be easily and quickly analyzed concurrently, which further improves the value of the present methods.

Also provided are certain novel PAG-binding polypeptides that can be applied in methods to detect pregnancy in a subject, and polynucleotides encoding the polypeptides set forth herein. The remaining disclosure describes various features of the invention and their implementation.

I. Polypeptides

Some embodiments of the invention set forth herein pertain to isolated and purified polypeptides that include a PAG binding domain having greater than 97% sequence identity to SEQ ID NO:1 or greater than 92% sequence identity to SEQ ID NO:2. In some embodiments, the PAG binding domain has greater than 97.1%, 97.3%, 97.5%, 97.7%, 97.9%, 98.1%, 98.3%, 98.5%, 98.7%, 98.9%, 99.1%, 99.3%, 99.5%, 99.7%, 99.9%, or 100% sequence identity to SEQ ID NO:1. In some embodiments, the PAG binding domain has greater than 92.2%, 92.6%, 93.0%, 93.4%, 93.8%, 94.2%, 94.6%, 95.0%, 95.4%, 95.8%, 96.2%, 96.6%, 97.0%, 97.4%, 97.8%, 98.2%, 98.6%, 99.0%, 99.4%, 99.8%, or 100% sequence identity to SEQ ID NO:2.

A "polypeptide" as used herein refers to a consecutive amino acid segment of any length. In some embodiments of the present methods, the polypeptides employed therein are a consecutive amino acid that includes within its sequence an amino acid sequence having greater than 97% sequence identity to SEQ ID NO:1 or greater than 92% sequence identity to SEQ ID NO:2. One of ordinary skill in the art would understand how to generate such a polypeptide in view of the disclosure set forth herein using any of a number of experimental methods well-known to those of skill in the art.

The term "percent sequence identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (1988); Biocomputing: Informatics and Genome Projects (1993); Computer Analysis of Sequence Data, Part I (1994); Sequence Analysis in Molecular Biology (1987); and Sequence Analysis Primer (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

It is well understood by the skilled artisan that, inherent in the definition of a "polypeptide," is the concept that there is a limit to the number of changes that may be made within a defined portion of the molecule and still result in a molecule with an acceptable level sequence identity or function, e.g., ability of bind to a PAG.

An amino acid sequence of any length is contemplated within the definition of polypeptide as set forth herein, so long as the polypeptide retains the recited sequence identity. The PAG binding domain of the polypeptides set forth herein may have additional amino acids at either the C-terminal or N-terminal end. For example, the polypeptide equivalent may include 4, 5, 6, 7, 8, 9, 10, 15, 20, 50, 75, 100, 125, 150, 175, 200, 300, 400, 500, 600, 700, 800, 900, 1000, or more additional nucleic acids attached to either the C-terminal end or N-terminal end of the PAG binding domain.

Of course, a plurality of distinct polypeptides with different substitutions may easily be made and used in accordance with the invention.

The present invention may utilize polypeptides purified from a natural source or from recombinantly-produced material. Those of ordinary skill in the art would know how to produce these polypeptides from recombinantly-produced material. This material may use the 20 common amino acids in naturally synthesized proteins, or one or more modified or unusual amino acids. Generally, "purified" will refer to a polypeptide composition that has been subjected to fractionation to remove various other proteins, polypeptides, or peptides, and which composition substantially retains its activity. Purification may be substantial, in which the polypeptide is the predominant species, or to homogeneity, which purification level would permit accurate degradative sequencing.

Amino acid sequence mutants are encompassed by the present invention, and are included within the definition of "polypeptide." Amino acid sequence mutants of the polypeptide can be substitutional mutants or insertional mutants. Insertional mutants typically involve the addition of material at a non-terminal point in the peptide. This may include the insertion of a few residues; an immunoreactive epitope; or simply a single residue. The added material may be modified, such as by methylation, acetylation, and the like. Alternatively, additional residues may be added to the N-terminal or C-terminal ends of the peptide.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated by reference herein). It is known that certain amino acids may be substituted for other amino acids having a similar hydropathic index or score and still retain a similar biological activity. In making changes based upon the hydropathic index, the substitution of amino acids whose hydropathic indices are within +2 is preferred, those which are within +1 are particularly preferred, and those within +0.5 are even more particularly preferred.

It is understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0+1); glutamate (+3.0+1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within +2 is preferred, those which are within +1 are particularly preferred, and those within +0.5 are even more particularly preferred.

II. Polynucleotides

Various aspects of the present invention pertain to polynucleotides that encode a polypeptide that includes a domain having greater than 97% sequence identity to SEQ ID NO:1 or greater than 92% sequence identity to SEQ ID NO:2. Other embodiments set forth herein pertain to isolated and purified polynucleotides that encode a polypeptide having a domain that has greater than 97% sequence identity to SEQ ID NO:1 or greater than 92% sequence identity to SEQ ID NO:2. Also disclosed are polynucleotides comprising a nucleic acid sequence that has greater than 98% sequence identity to SEQ ID NO:5 or greater than 95% sequence identity to SEQ ID NO:6. SEQ ID NO:5 refers to the nucleic acid sequence of the cDNA that encodes the light chain of 2D9, and SEQ ID NO:6 refers to the nucleic acid sequence of the cDNA that encodes the heavy chain of 2D9.

In some embodiments, the polynucleotide has 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9%, or 100% sequence identity to SEQ ID NO:5. In some embodiments, the polynucleotide has greater than 95.2%, 95.4%, 95.6%, 95.8%, 96.0%, 96.2%, 96.4%, 96.6%, 96.8%, 97.0%, 97.2%, 97.4%, 97.6%, 97.8%, 98.0%, 98.2%, 98.4%, 98.6%, 98.8%, 99.0%, 99.2%, 99.4%, 99.6%, 99.8%, or 100% sequence identity to SEQ ID NO:6.

The polynucleotides may be obtained from natural sources or chemically synthesized using any method known to those of ordinary skill in the art. The present invention also encompasses chemically synthesized mutants of these sequences.

In certain embodiments, one may wish to employ constructs which include other elements, for example, those which include C-5 propyne pyrimidines. Oligonucleotides which contain C-5 propyne analogues of uridine and cytidine have been shown to bind RNA with high affinity (Wagner et al., 1993). In some embodiments, the polynucleotide encodes one or more additional amino acid segments that can bind to a PAG.

III. Antibodies and Antibody Fragments

Particular embodiments of the present invention involve antibodies or antibody fragments. The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with the present invention. Minibodies are sFv polypeptide chains which include oligomerization domains at their C-termini, separated from the sFv by a hinge region. Pack et al. (1992). The oligomerization domain comprises self-associating .alpha.-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in the present invention. Liu et al., 2003, describe "antibody like binding peptidomimetics" (ABiPs), which are peptides that act as pared-down antibodies and have certain advantages of longer serum half-life as well as less cumbersome synthesis methods.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more complementarity determining regions (CDRs) from a non-human (usually a mouse or rat) immunoglobulin. The non-human immunoglobulin providing the CDRs is called the "donor" and the human immunoglobulin providing the framework is called the "acceptor". A "humanized antibody" is an antibody comprising a humanized light chain and a humanized heavy chain immunoglobulin.

The term "antibody" includes polyclonal antibodies, monoclonal antibodies (mAbs), chimeric antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques. The antibodies set forth herein are capable of binding to a PAG.

"Polyclonal antibodies" are defined herein to refer to heterogeneous populations of antibody molecules derived from the sera of animals immunized with an antigen. These different antibodies may recognize several epitopes on the same antigen. A "monoclonal antibody" contains a substantially homogeneous population of antibodies specific to antigens, which population contains substantially similar epitope binding sites. MAbs may be obtained by methods known to those skilled in the art. See, e.g., Kohler and Milstein, 1975; U.S. Pat. No. 4,376,110; Ausubel et al., 1992); Harlow and Lane 1988; Colligan et al., 1993, the contents of which are each herein specifically incorporated by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

"Chimeric antibodies" are molecules different portions of which are derived from different animal species, such as those having variable region derived from a murine mAb and a human immunoglobulin constant region, which are primarily used to reduce immunogenicity in application and to increase yields in production. Chimeric antibodies and methods for their production are known in the art. Exemplary methods of production are described in Cabilly et al., 1984; Boulianne et al., 1984; and Neuberger et al., 1985, each of which are herein incorporated by reference in their entirety.

An "anti-idiotypic antibody" (anti-Id) is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). An exemplary method of producing such antibodies is found in U.S. Pat. No. 4,699,880, which is herein entirely incorporated by reference.

Antibodies of the present invention can include at least one heavy, at least one light chain, a heavy chain constant region, a heavy chain variable region, a light chain variable region and/or a light chain constant region, wherein a polyclonal Ab, monoclonal Ab, fragment and/or regions thereof include at least one heavy chain variable region or light chain variable region that binds a portion of a PAG.

Certain embodiments of the present invention pertain to methods for detecting pregnancy in an animal that involve obtaining a sample from the animal and contacting the sample with an antibody or antibody fragment, wherein the antibody or antibody fragment comprises a domain that binds to one or more of boPAG4, boPAG6, boPAG9, boPAG20 and/or boPAG21 and detecting contacting of the antibody or antibody fragment with PAG(s) in the sample, wherein detection of the PAG(s) indicates that the animal is pregnant. Any method known to those of ordinary skill in the art can be used to identify an antibody that binds to PAG. Examples of references which address methods for defining variable regions of IgGs include Mo et al. (1993) and Leibiger et al. (1999), herein specifically incorporated by reference.

IV. Detection Methods and Assay Formats

Certain embodiments of the present invention pertain to methods of detecting pregnancy in an animal that involves contacting a sample obtained from an animal with an antibody provided herein and detecting at least one pregnancy associated antigen in the sample, wherein detection of the PAG indicates the animal is pregnant. Any method known to those of ordinary skill in the art can be used to detect antibody or antibody fragments bound to a PAG in the sample.

The present invention therefore provides for the use of antibodies in the immunologic detection of PAGs. Various useful immunodetection methods have been described in the scientific literature, such as, e.g., Nakamura et al. (1987). Immunoassays, in their most simple and direct sense, are binding assays. Certain immunoassays are enzyme linked immunosorbent assays (ELISAs) and radioimmunoassays (RIA) Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes. Preferred samples, according to the present invention, are fluids, such as milk, urine, blood, serum or saliva.

In particular embodiments, the antibody is linked to a solid support, such as the inner wall of a tube or well, and the sample suspected of containing the PAG will be applied to the immobilized antibody.

Antibody-coated tube systems are described in U.S. Pat. No. 3,646,346 and WO 98/16832, each of which is herein specifically incorporated by reference. Presence of PAG-antibody complexes can then be detected under specific conditions. Optionally, such immune complexes can be quantified.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any PAG present in the sample. After this time, the sample-antibody composition will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Methods for the immunological determination of proteins and kits for carrying out the method can be found in U.S. Pat. No. 5,721,105, herein specifically incorporated by reference.

In particular embodiments, the method involves the use of a secondary binding ligand such as a second antibody and/or a biotin/avidin ligand binding arrangement, as is known in the art. The secondary antibody employed in the detection may itself be linked to a detectable label, wherein one would then simply detect this label, thereby allowing the amount of the primary immune complexes in the composition to be determined. Methods for the detection of a biomolecule in a test sample using immunocapture, biotin/avidin amplification, and horseradish peroxidase color production can be found in U.S. Patent App. Pub. No. 2003/508381.

Usually, the primary immune complexes may be detected by means of a second binding ligand that has binding affinity for the PAG or the PAG-specific first antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the PAG or anti-PAG antibody is used to form secondary immune complexes, as described above. The second binding ligand contains an enzyme capable of processing a substrate to a detectable product and, hence, amplifying signal over time. After washing, the secondary immune complexes are contacted with substrate, permitting detection.

In one embodiment of the invention, enzyme-linked immunoassay (ELISA) may be used. See, e.g., Engvall, 1980; Engvall, 1976; Engvall, 1977; Gripenberg et al., 1978; Makler et al., 1981; Sarangadharan et al., 1984. ELISA allows for substances to be passively adsorbed to solid supports such as plastic to enable facile handling under laboratory conditions. For a comprehensive treatise on ELISA the skilled artisan is referred to "ELISA; Theory and Practise" (Crowther, 1995).

The sensitivity of ELISA methods is dependent on the turnover of the enzyme used and the ease of detection of the product of the enzyme reaction. Enhancement of the sensitivity of these assay systems can be achieved by the use of fluorescent and radioactive substrates for the enzymes Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In one embodiment, the invention comprises a "sandwich" ELISA, where anti-PAG antibodies of the present invention are immobilized onto a selected surface, such as a well in a polystyrene microtiter plate, a tube, or a dipstick. Then, a test composition suspected of containing PAGs, e.g., a clinical sample, is contacted with the surface. After binding and washing to remove non-specifically bound immunocomplexes, the bound antigen may be detected by a second antibody to the PAG.

In another exemplary ELISA, polypeptides from the sample are immobilized onto a surface and then contacted with the anti-PAG antibodies. After binding and washing to remove non-specifically bound immune complexes, the bound antibody is detected. Where the initial antibodies are linked to a detectable label, the primary immune complexes may be detected directly. Alternatively, the immune complexes may be detected using a second antibody that has binding affinity for the first antibody, with the second antibody being linked to a detectable label.

Another ELISA in which the PAGs are immobilized involves the use of antibody competition in the detection. In this ELISA, labeled antibodies are added to the wells, allowed to bind to the PAG, and detected by means of their label. The amount of PAG in a sample is determined by mixing the sample with the labeled antibodies before or during incubation with coated wells. The presence of PAG in the sample acts to reduce the amount of antibody available for binding to the well, and thus reduces the ultimate signal.

Irrespective of the format employed, ELISAs have certain features in common, such as coating, incubating or binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These can include bovine serum albumin (BSA), casein, solutions of milk powder or other antigenically neutral proteins. The coating allows for blocking of nonspecific adsorption sites on the immobilizing surface and thus reduces the background caused by nonspecific binding of antisera onto the surface.

"Under conditions effective to allow immune complex (antigen/antibody) formation" means that the conditions preferably include diluting the antigens and antibodies with solutions such as BSA, bovine gamma globulin (BGG), evaporated or powdered milk, and phosphate buffered saline (PBS)/TWEEN. These added agents also tend to assist in the reduction of nonspecific background.

The "suitable" conditions also mean that the incubation is at a temperature and for a period of time sufficient to allow effective binding. Incubation steps are typically from about 1 h to 2 h to 4 h, at temperatures preferably on the order of 25° C. to 27° C., or may be overnight at about 4° C. or so.

To provide a detecting means, the second or third antibody will have an associated label to allow detection. Often, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-TWEEN).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzothiazoline-6-sulfonic acid [ABTS] and $H_2O_2$, in the case of peroxidase as the enzyme label. Quantitation is then achieved by measuring the degree of color generation, e.g., using a visible spectra spectrophotometer.

A variant of ELISA is the enzyme-linked coagulation assay, or ELCA (U.S. Pat. No. 4,668,621), which uses the coagulation cascade combined with the labeling enzyme RVV-XA as a universal detection system. The advantage of this system for the current invention, is that the coagulation reactions can be performed at physiological pH in the presence of a wide variety of buffers. It is therefore possible to retain the integrity of complex analytes.

Immunohistochemistry (IHC) may also be used according to the present invention in the identification of PAGs. This involves testing of both fresh-frozen and formalin-fixed, paraffin-embedded tissue blocks prepared from study by IHC. For example, each tissue block consists of 50 mg of residual "pulverized" placental tissue. The method of preparing tissue blocks from these particulate specimens has been successfully used in previous IHC studies of various prognostic factors, e.g., in breast, and is well known to those of skill in the art (Brown et al., 1990; Abbondanzo et al., 1990; Allred et al., 1990).

Briefly, frozen-sections may be prepared by rehydrating 50 mg of frozen "pulverized" placental tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections containing an average of about 500 remarkably intact placental cells.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

V. Purification of Proteins

Certain embodiments pertain to an isolated or purified polypeptide, or methods employing an isolated or purified polypeptide. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or polypeptide. The term "purified polypeptide, protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various techniques suitable for use in protein purification will be well known to those of skill in the art. These include, for example, precipitation with ammonium sulphate, PEG, antibodies and the like or by heat or acid pH denaturation of contaminating proteins, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the polypeptide always be provided in its most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

VI. Kits

In still further embodiments, the present invention provides kits for use with the immunodetection methods described above for the detection of PAGs, such as an immunodetection kit to diagnose pregnancy in a bovine. In specific embodiments, an antibody comprising a domain having greater than 97% sequence identity to SEQ ID NO:1 or greater than 92% sequence identity to SEQ ID NO:2 are included in the kit. The kit may include one or more container means. The container, for example, may be a vial, a tube, a flask, a vial, or a syringe.

In particular embodiments, the antibody is monoclonal antibody 2D9. In particular embodiments, the kit includes one or more tubes or wells of a microtiter plate with prebound antibody. Alternatively, the kit may include antibody prebound to a column matrix. The kit may allow for the assay of a single sample, or more than one sample. In some embodiments, the kit includes a plurality of microtiter plates or tubes coated with antibody which allow for immunodetection of numerous samples concurrently or consecutively.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

In some embodiments, the kits include a secondary antibody that has binding affinity for the first antibody. The second antibody may or may not be linked to a detectable label. In some further embodiments, the kit includes a third antibody that has binding affinity for the second antibody, the third antibody being linked to a detectable label. As noted above, a number of exemplary labels are known in the art and/or all such labels may be employed in connection with the present invention.

The kits may optionally include a suitably aliquoted composition of a PAG to provide for a positive control. The components of the kits may be packaged either in aqueous media and/or in lyophilized form.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of 2D9 Binding PAGs

Studies were undertaken to identify the proteins binding to 2D9, to characterize and sequence the 2D9 antibody, and to map the binding sites of PAG to 2D9. In order to accomplish this, two approaches (described below) were under taken.

Materials and Methods.

Immunoprecipitation of PAGs with 2D9-Coated Magnetic Beads.

Purified 2D9 was coupled to Tosyl-activated Dynal magnetic beads according to manufacturer's directions (Dynal). The antibody coated magnetic beads were incubated with 100 micrograms of PAG enriched preparation (obtained from day 55 placenta) for 30 min in 1×PBS and washed extensively with the same buffer. The bound proteins were eluted by using pH 3.0 acetic acid and subjected gel and Western blot analysis. Western blot was developed with rabbit anti-PAG polyclonal antibodies. The immuno-reactive protein bands were cut from SDS-PAGE and subjected to LC-MS-MS analysis after trypsin digestion (FIG. 3).

Immuno-Affinity Chromatography of Tissue Extracts Prepared from Caruncle (Endometrium) and Cotyledonary (Placenta) Tissues from Day 55 of Bovine Pregnancy.

Figure 4:
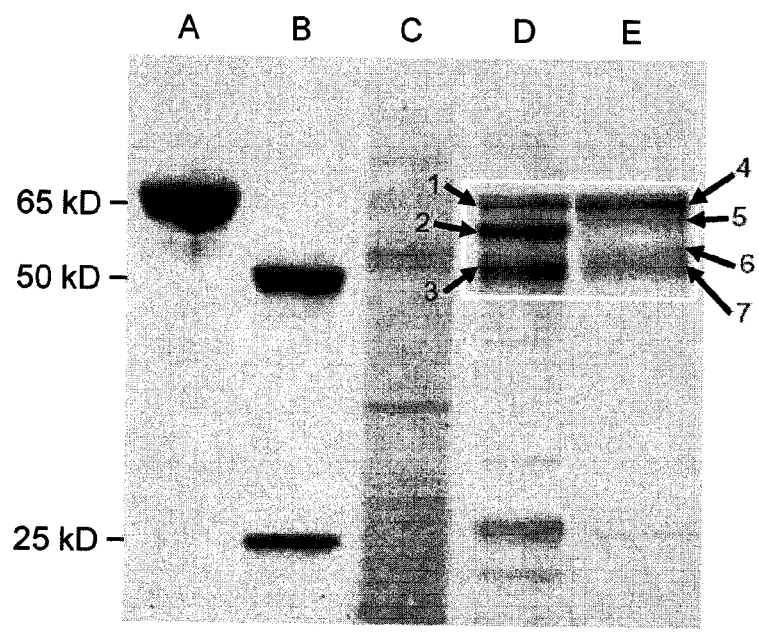
FIG. 4. Coomassie blue stained SDS-PAGE showing 2D9 binding PAGs purified by immuno-affinity chromatography of caruncle (endometrium) and cotyledon (placenta) tissue extracts. Protein bands 1 to 7 were cut and subjected trypsin digestion followed by LC-MS-MS analysis (SEQ ID NOS:7-18).

Briefly, purified 2D9 (10 mg) was coupled to 1 gram of CNBr-activated sepharose according to manufacturer's directions (Sigma, St. Louis). The 2D9-affinity resin (approximately 5.0 ml) was incubated with 25 ml tissue extract at pH 7.0, overnight for binding. Next day, the resin was packed in a column and washed with 1×PBS to remove unbound materials and eluted with pH 3.0 acetic acid. The pH of the eluted material was neutralized with 1M Tris immediately after elution to pH 7.0. The eluted material was subjected gel and Western blot analysis. Western blot was developed with rabbit anti-PAG polyclonal antibodies. The protein bands 1 to 7 were cut from SDS-PAGE and subjected to LC-MS-MS analysis after trypsin digestion (FIG. 4). The identities of peptide sequences were determined by using BLAST analysis.

The binding affinity of PAG to 2D9 was determined by log-log transformation of ELISA data (FIG. 5) developed with 2D9-binding antigen as PAG standards (purified by immuno-affinity chromatography). The assay was performed with a series of PAG standards ranging from 0.05 ng/ml to 50 ng/ml (0.083 nM to 8.3 nM). The ELISA assay was repeated 8 times. The data was analyzed with SoftMax™ (Molecular Devices, Inc., Sunnyvale, Calif.).

Results

Immunoprecipitation of PAGs with 2D9-Coupled Magnetic Beads.

SDS-PAGE and Western blot analysis of magnetic bead eluted material showed a single protein band at 67 kD. Peptide finger printing and LC-MS-MS analysis identified this protein band as boPAG6 (FIG. 3). However, this analysis did not reveal all PAGs binding to 2D9 since the analysis used 100 micrograms of PAG enriched preparation for immunoprecipitation experiment. This material was isolated by pepstatin-affinity chromatography of placental tissue extract at pH 5.0, followed by elution at pH 9.5. This preparation was also called 'acidic-PAGs', an enriched preparation of early PAG antigens. In order to identify all PAGs binding to 2D9, an immuno-affinity chromatography with tissue extracts were performed (see below).

Analysis of PAGs Purified from Tissue Extracts with 2D9-Immuno-Affinity Chromatography.

Coomassie blue staining of immuno-affinity column eluted material showed 3 protein bands with molecular weights 67 kD, 55 kD and 50 kD. All three protein bands were also found to be immuno-reactive in Western blot analysis with rabbit anti-PAG antibodies. Based on these results, all protein bands were cut after SDS-PAGE (FIG. 4) and subjected to peptide finger printing and LC-MS-MS. The identities of resulting peptide sequences were determined by BLAST analysis. Table 1 shows a summary of the peptide sequence results and their identification as PAGs corresponding to boPAG-4, boPAG-6, boPAG-9, boPAG-20 and boPAG21 sequences by BLAST analysis. For meaning of parameters in Table 1, see description of FIG. 3.

TABLE 1

Summary of peptide sequence results

| Mz | Charge | Mr (calc) | Start | End | Score | Peptide sequence |
|---|---|---|---|---|---|---|
| \multicolumn{7}{c}{Protein Band No.: Present in Bands 3, 5, 6 & 7} | | | | | | |
| \multicolumn{7}{c}{Bos Taurus (gi28603710) Pregnancy-associated glycoprotein 4} | | | | | | |
| 494.7897 | 2 | 969.5647 | 323 | 331 | 97.72% | VPGQAYILK (SEQ ID NO: 19) |
| 523.7799 | 2 | 1027.5127 | 362 | 369 | 99.00% | LYFSVFDR (SEQ ID NO: 20) |
| 544.7657 | 2 | 1069.5193 | 127 | 136 | 98.95% | TFSITYGSGR (SEQ ID NO: 21) |
| 608.8262 | 2 | 1197.6216 | 232 | 241 | 94.10% | GELNWIPLMK (SEQ ID NO: 22) |
| 671.695 | 3 | 1994.0513 | 195 | 212 | 99.00% | LKNEGAISEPVFAFYLSK (SEQ ID NO: 23) |
| 820.4574 | 3 | 2440.2678 | 172 | 194 | 87.95% | FDGVLGLSYTNISPSGAIPIFYK (SEQ ID NO: 24) |
| \multicolumn{7}{c}{Protein Band No.: Present in Bands 1, 2, 4 & 5} | | | | | | |
| \multicolumn{7}{c}{Bos Taurus (gi28603714) Pregnancy-associated glycoprotein 6} | | | | | | |
| 886.4235 | 2 | 1752.8722 | 196 | 211 | 88.08% | NEGAISEPVFAFYLSK (SEQ ID NO: 25) |
| 881.9394 | 2 | 1743.8865 | 147 | 162 | 95.46% | IGDLVSTDQPFGLCLK (SEQ ID NO: 26) |
| 809.7131 | 3 | 2408.1736 | 231 | 250 | 91.77% | GELNWVPLIQVGDWFVHMDR (SEQ ID NO: 27) |
| 671.6718 | 3 | 1994.0513 | 194 | 211 | 97.94% | LKNEGAISEPVFAFYLSK (SEQ ID NO: 28) |
| 615.3026 | 2 | 1210.6022 | 183 | 193 | 98.74% | TFSGAFPIFDK (SEQ ID NO: 29) |
| 592.9321 | 3 | 1757.8154 | 212 | 227 | 99.00% | DKQEGSVVMFGGVDHR (SEQ ID NO: 30) |
| 511.9066 | 3 | 1514.6936 | 214 | 227 | 90.49% | QEGSVVMFGGVDHR (SEQ ID NO: 31) |
| 467.2242 | 2 | 914.4286 | 362 | 368 | 91.26% | YFSVFDR (SEQ ID NO: 32) |
| \multicolumn{7}{c}{Protein Band No.: Present in Bands 2 & 5} | | | | | | |
| \multicolumn{7}{c}{Bos Taurus (gi28603720) Pregnancy-associated glycoprotein 9} | | | | | | |
| 467.2146 | 2 | 914.4286 | 362 | 368 | 99.00% | YFSVFDR (SEQ ID NO: 33) |
| 521.2636 | 2 | 1022.5185 | 138 | 146 | 99.00% | GFLAYDTVR (SEQ ID NO: 34) |
| 653.9534 | 3 | 1940.8727 | 214 | 230 | 96.15% | QEGSVVMFGGVDHQYYK (SEQ ID NO: 35) |
| 654.80054 | 2 | 1289.5962 | 126 | 137 | 97.70% | TFTITYGSGSMK (SEQ ID NO: 36) |
| 660.8375 | 2 | 1301.6768 | 350 | 360 | 94.72% | ETWILGDAFLR (SEQ ID NO: 37) |
| 734.6413 | 3 | 2183.0105 | 212 | 230 | 87.19% | NKQEGSVVMFGGVDHQYYK (SEQ ID NO: 38) |
| 739.9147 | 2 | 1459.8439 | 307 | 319 | 99.00% | YLPSITFIINGIK (SEQ ID NO: 39) |
| 817.7423 | 3 | 2432.2222 | 147 | 169 | 99.00% | IGDLVSTDQPFGLSVVEYGLEGR (SEQ ID NO: 40) |
| 875.3999 | 3 | 2605.2012 | 256 | 280 | 83.62% | TVIACSDGCEALVHTGTSHIEGPGR (SEQ ID NO: 41) |
| \multicolumn{7}{c}{Protein Band No.: Present in Bands 1 & 4} | | | | | | |
| \multicolumn{7}{c}{Bos Taurus (gi28603736) Pregnancy-associated glycoprotein 20} | | | | | | |
| 671.6718 | 3 | 1994.0513 | 195 | 212 | 97.94% | LKNEGAISEPVFAFYLSK (SEQ ID NO: 42) |
| 758.8157 | 2 | 1497.7511 | 215 | 228 | 80.98% | QKGSVVMFGGVDHR (SEQ ID NO: 43) |
| 886.4235 | 2 | 1752.8722 | 197 | 212 | 88.08% | NEGAISEPVFAFYLSK (SEQ ID NO: 44) |
| \multicolumn{7}{c}{Protein Band No.: Present in Bands 3, 5 & 7} | | | | | | |
| \multicolumn{7}{c}{Bos Taurus (gi28603738) Pregnancy-associated glycoprotein 21} | | | | | | |
| 516.7575 | 2 | 1013.497 | 362 | 369 | 99.00% | VYFSVFDR (SEQ ID NO: 45) |
| 544.7657 | 2 | 1069.5193 | 127 | 136 | 98.95% | TFSITYGSGR (SEQ ID NO: 46) |
| 694.3238 | 3 | 2061.9712 | 258 | 277 | 98.47% | VVACSDGCEAVVDTGTSLIK (SEQ ID NO: 47) |
| 753.6964 | 3 | 2240.1 | 148 | 168 | 99.00% | IGDLVSTDQPFGLSVSEYGFK (SEQ ID NO: 48) |
| 892.1082 | 3 | 2655.2744 | 171 | 194 | 99.00% | AYDGILGLNYPDESFSEAIPIFDK (SEQ ID NO: 49) |
| 915.4483 | 2 | 1810.8889 | 346 | 361 | 81.37% | FSSSTETWLLGDAFLR (SEQ ID NO: 50) |

This analysis showed that each of the 3 protein bands have more than one PAGs (Table 1). The 67 kD band contained peptides corresponding to boPAG6 and boPAG20. The 55 kD protein band contained peptides belonging to boPAG6 and boPAG9. The 50 kD protein band corresponded to boPAG4 and boPAG21 with boPAG9 as minor component. These results show that 2D9 monoclonal antibody binds to boPAG4, boPAG6, boPAG9, boPAG20 and boPAG21. This monoclonal antibody binds to epitopes common to all 5 PAGs. Sequence comparison showed a high degree of sequence identity among these PAGs.

Figure 5:
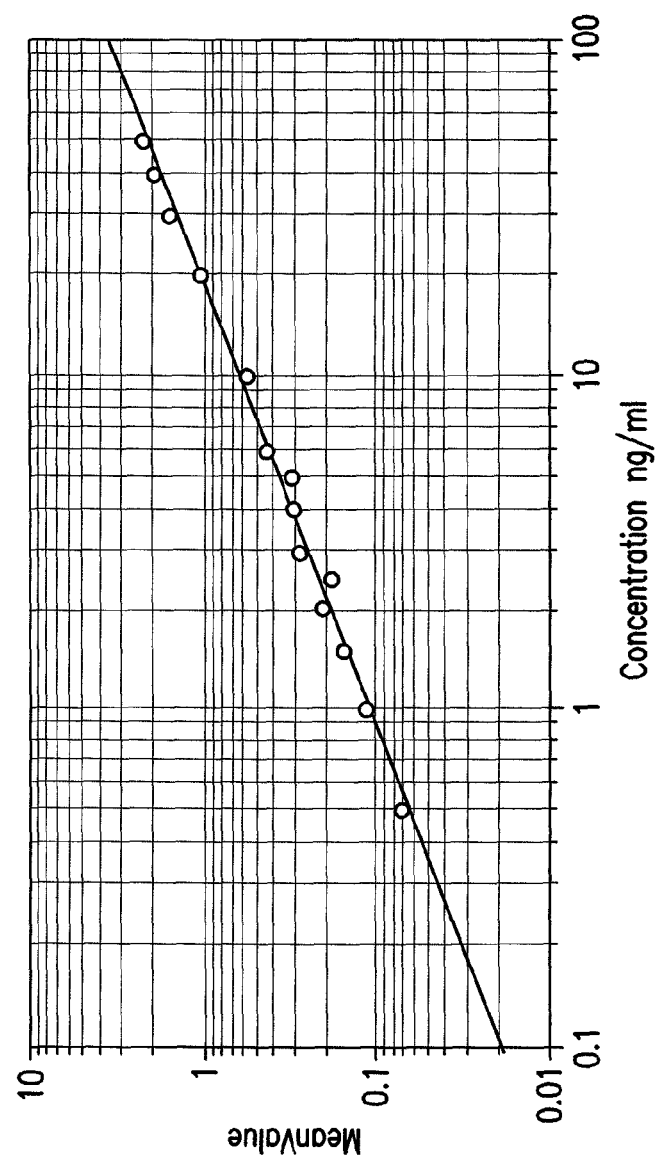
FIG. 5. Log-logit transformation of PAG ELISA standard curve developed with 2D9-antibody coated ELISA plates and immuno-affinity purified PAGs as standards. The assay showed a linear response from 0.5 ng/ml to 50 ng/ml.

The PAG ELISA results (FIG. 5) obtained by using 2D9-binding PAGs as standards was used for calculating Kd value by using SoftMax™. The Kd value of 2D9 was determined to be 0.9 nM (FIG. 5). Thus, 2D9 is a high affinity monoclonal antibody for PAGs. These results show that 2D9, a PAG monoclonal antibody, binds to boPAG4, boPAG6, boPAG9, boPAG20 and boPAG21 from a day 55 placental tissue extracts. The identities of peptide sequences obtained by LC-MS-MS corresponded with a previously characterized sequences of these 5 PAGs (boPAG4, boPAG6, boPAG9, boPAG20 and boPAG21).

Example 2

Protein and mRNA Sequencing

Protein Sequencing of Purified 2D9.

The sequencing of 2D9 was performed in order to identify PAG-antigen binding sequences of 2D9. The sequencing of 2D9 was accomplished by protein and DNA sequencing methods. First, heavy and light chains of 2D9 antibody were separated by denaturing gel electrophoresis. The gel bands were excised and subjected to trypsin and chymotrypsin enzyme digestions, separately. The resulting peptides were separated and sequenced by LC-MS-MS (Liquid Chromatography-Mass Spectrometry-Mass Spectrometry) method. The peptides with >90% confidence score in the mass and sequence analysis were selected. The resulting peptide sequences were used to assemble ~80% of light chain sequence and ~50% of heavy chain sequence.

Sequencing of 2D9 Heavy and Light Chain mRNA.

In a second approach, mRNA corresponding to 2D9 heavy and light chains were sequenced by using reverse transcription-polymerase chain reaction (RT-PCR) technique with total RNA prepared from 2D9 PAG hybridoma cells.

Briefly, PAG monoclonal antibody producing hybridoma cells were grown in serum-free tissue culture medium to produce 1×10$^6$ cells. The cells were centrifuged and the resulting cell pellet was snap frozen in liquid nitrogen. The cell pellet was stored at −80° C. until use. The first strand complementary DNA (cDNA) was produced by using Cell-to-cDNA kit II purchased from Ambion, Inc., Austin, Tex. The RNA in the hybridoma cells was reverse transcribed to produce cDNA without a separate RNA extraction step. The resulting cDNA template was used for amplifying light and heavy chains by using polymerase chain reaction (PCR) with a set of primers designed for amplifying all subclasses of mouse heavy and light chains (Chardes et al., 1999). The resulting PCR product was sequenced. The sequence data was assembled with DNA STAR™ software package. The entire study was repeated to ensure sequence accuracy. Second repetition of PCR amplification and sequencing included additional primers to increase the coverage.

Sequence analysis showed that 2D9 heavy chain was derived from mouse IgG1 gamma subclass and the light chain was derived from kappa type. Heavy chain consisted of 448 amino acid residues and the light chain consisted of 219 amino acid residues. The amino acid sequence of 2D9 light chain is set forth as SEQ ID NO:3. The amino acid sequence of 2D9 heavy chain is set forth as SEQ ID NO:4. The nucleic acid sequence of 2D9 light chain is set forth as SEQ ID NO:5 (FIG. 1). The nucleic acid sequence of 2D9 heavy chain is set forth as SEQ ID NO:6 (FIG. 2).

Example 3

Feasibility Studies of an Immunoassay-Based Pregnancy Test in Cattle

A large-scale study was conducted to evaluate the economics of day 28 early pregnancy testing in the reproductive management of dairy cows. Study animals were located at two different sites, one in California and one in Wisconsin. 1,050 animals were assigned per site. Initial breeding was followed by either performance of an immunoassay based pregnancy test as described below, or by standard palpation. Samples were shipped to the laboratory overnight. The study used a sandwich ELISA optimized with rabbit anti-PAG polyclonal antibodies. The PAG ELISA used a cut off was 1.7 ng/ml, based on a trial study. Blood samples were collected on day 28 and shipped to laboratory for pregnancy testing. Pregnancy diagnosis was accomplished by PAG ELISA and a report of results was generated, and made available within 24 hours to farm personnel. Breeding decisions were made based on pregnancy diagnosis results from PAG test for early resynch group. Breeding decisions for the late resynch group (control) were made based on palpation at days 35 to 45. Results from the two sites are shown in FIGS. 6-8.

FIG. 6 shows the accuracy of a lab-based pregnancy diagnosis with PAG ELISA compared to ultrasound based pregnancy diagnosis. FIG. 6 show the accuracy of day 28 pregnancy diagnosis by using a lab-based ELISA compared to pregnancy diagnosis on day 28 ultrasound in two study sites, Wisconsin and California. Economics of a day 28 pregnancy test in dairy cow reproduction management was examined in this beta study. A lab-based PAG ELISA with polyclonal antibodies was used for pregnancy diagnosis. Wisconsin site used strictly synchronized breeding while California site used synchronized breeding plus breeding to heat. Approximately 1000 cows were used in the study per site. Blood samples were collected on day 28, shipped to lab for pregnancy testing. The results were returned to farms within 24 hrs to enable breeding decisions. Pregnancy status was also determined by ultrasound at the time of blood collection on day 28.

FIG. 7 and FIG. 8 show the results of breeding parameters used for determining economics of early pregnancy detection in the reproductive management of dairy cows in two different breeding schemes. The results clearly show that there is a significant reduction in the days open by 10 to 15 days in the early resynch group compared to controls. In addition, a reduction in the days between inseminations was observed in both sites.

These results show that early pregnancy testing with PAG ELISA after 27-30 days of insemination allowed earlier breeding compared to palpation. Early pregnancy testing significantly reduced 'days open' in re-breeding of cows. In addition, early pregnancy testing significantly reduced days between insemination. Breeding to heat strategy with early pregnancy testing was shown to reduce the number of inseminations per conception.

Example 4

On-Farm Test Concepts: Bovine Pregnancy Test (Strips)

A further study was conducted to evaluate the feasibility of use of 2D9 in developing an 'on-farm' pregnancy test with test strips. The test strips used lateral flow technology, which is the same technology used in home pregnancy tests. Lateral flow test strips have colloidal gold conjugated antibody at the sample application end and a capture antibody placed as a test line at the middle of the strip. If test antigen (PAG) is present in the sample, then gold conjugated antibody will bind to antigen and the resulting complex migrates towards test line. At the test line, the capture antibody (also raised against PAG) will bind to this complex and concentrate at the line. When sufficient complexes are retained at the test line as an antibody sandwich, a visible purple line will appear due to colloidal gold labeled antibody bound to test antigen. Lateral flow strips with more than 40 combinations of antibodies (including 2D9 as capture antibody) were produced and tested. None of the lateral flow strip combinations tested produced acceptable sensitivity and specificity. As a result, other rapid diagnostic test formats were evaluated for developing an 'on-farm' test. Among the formats evaluated, plastic tubes with internal fins showed promising results. Because of this, the tube format was selected for further optimization as a color test.

Example 5

On-Farm Test Concepts: Bovine Pregnancy Test (Multi-Well Plates)

Figure 9:
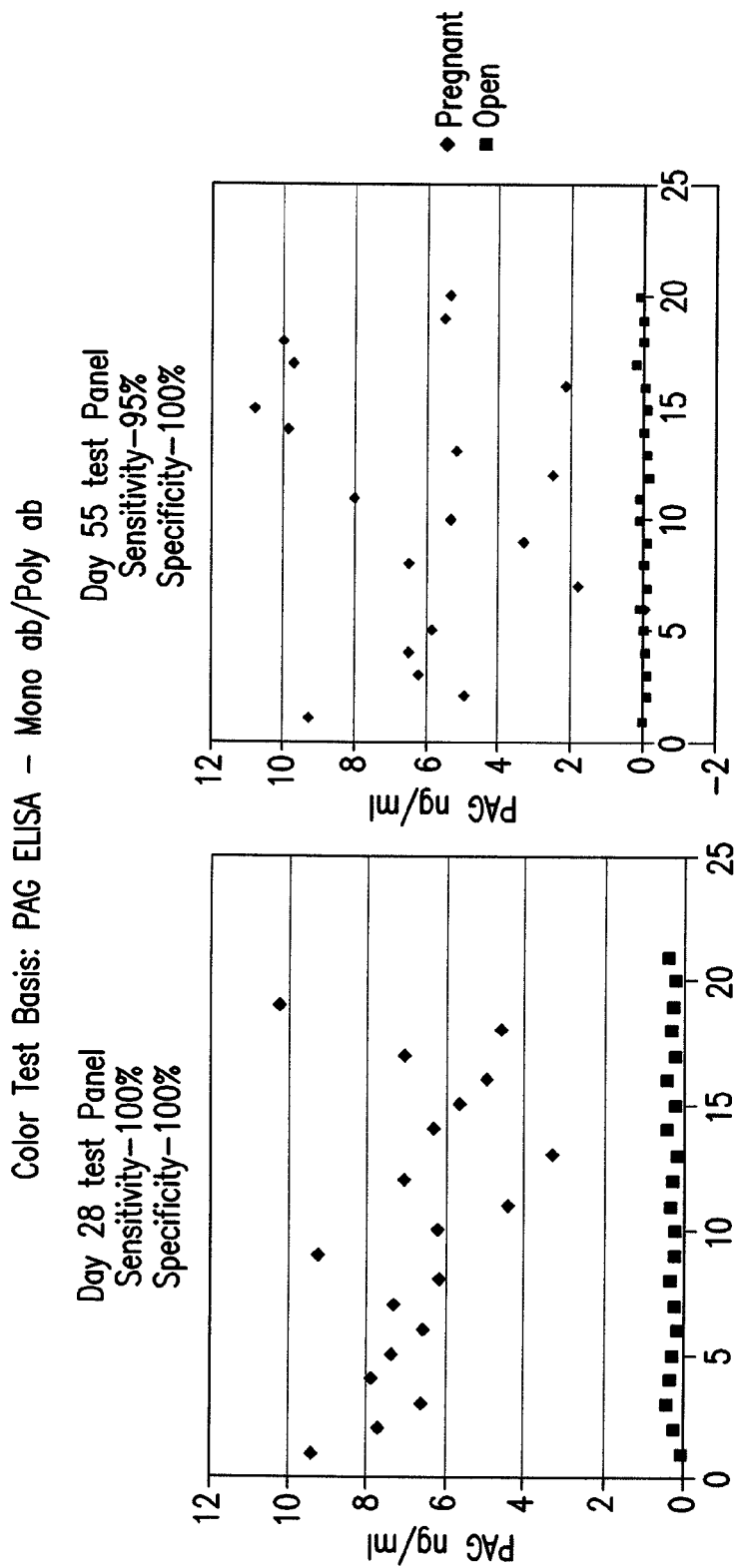
FIG. 9. Color test basis. Results of PAG immunoassay developed with 2D9 monoclonal antibody as capture antibody and biotin-labeled rabbit polyclonal antibody as second antibody. Plasma test panel (20 open and 20 pregnant) samples collected at day 28 and day 55 of pregnancy showed a complete separation of open cows (blue) compared to pregnant cows (pink). The near zero PAG value obtained for open cows suggested that a PAG standard may not be needed for qualitative detection of immunoreactive PAG in the test plasma.

In a further study, plasma samples collected from day 28 of confirmed pregnant cows was used to determine the sensitivity and specificity of the color test. Color intensity was determined by transferring the sample solution to a multi-well plate coated with 2D9. The plate was read in a plate reader (SpectraMax, Molecular Devices, Inc., CA). The plasma panel consisted of 20 pregnant and 20 open (non-pregnant) samples. Each sample was assayed in duplicate. Based on the optical density of color intensities obtained from the 40 samples, by using a 0.2 OD unit cut-off as a background color, the test showed 100% sensitivity and 100% specificity (FIG. 9).

Example 6

On-Farm Test Concepts: Bovine Color Pregnancy Test (Plastic Tubes)

Materials and Methods.

Following protocol describes the optimized procedure for pregnancy testing with 2D9-coated plastic tubes. The test can be performed with whole blood sample collected with K3EDTA blood collection tubes or with plasma samples.

Materials.

Tubes with internal ribs (#214-2131-010) were purchased from Evergreen Scientific Company, Los Angeles, Calif. PAG monoclonal antibody, 2D9 and rabbit polyclonal antibodies were purified by Protein G affinity chromatography. Biotin-labeling of rabbit polyclonal antibodies was accomplished by using Roche biotin-labeling kit (#1-418-165, Roche Applied Science, Indianapolis, Ind.) according to manufacturer's directions. Streptavidin-PolyHRP20 ® (#RDI-PHRP20-SA) was purchased from Research Diagnostics, Inc, Concord, Mass. Sure Blue Reserve® (#53-00-03) was procured from KPL, Inc, Gaithersburg, Md. SuperBlock with TWEEN20 ® (#37516) was acquired from Pierce Biotech, Rockford, Ill. Purified 2D9 monoclonal antibody in Phosphate Buffered Saline (pH7.4) with known concentration; Coating buffer: 0.1M $Na_2CO_3$, pH 9.3; Wash buffer: 1×PBS with 0.05% Tween20; Dilution buffer: 10% SuperBlock™ in wash buffer.

Biotin-Labeling of Polyclonal Antibodies.

Purified rabbit polyclonal antibody (1 mg) was used for biotin labeling according to recommended procedure by the kit manufacturer (Roche). Briefly, 7.6 μl of activated biotin reagent in DMSO was added to 1 mg of antibody in 1.0 ml of PBS solution in a 1.5 ml tube. The tube was placed on a rotary shaker with 45 rpm setting for 2 hours at room temperature. After this step, the contents were transferred to a dialysis Slide-A-Lyzer™ (Pierce Biotech, #63380) and dialyzed against 1×PBS at 4° C. for 16 hours with 2 buffer changes. Biotin labeled IgG was recovered from the Slide-A-lyzer and stored as 1:100 diluted stock with 1% BSA in PBS. This solution was diluted to 1:2000 with dilution buffer for pregnancy testing prior to use.

Antibody Coating of Tubes.

Purified monoclonal antibody, 2D9 was diluted in 0.1M sodium carbonate buffer (ph 9.3) to a concentration of 1.25 μg/ml for coating tubes. The tubes were coated with 0.5 μg of antibody in 0.4 ml of sodium carbonate buffer for 16 to 18 hours at 4° C. for coating. For incubation, the tubes were placed inside of a plastic container with an air-tight lid closed tightly plus a moist paper towel for humidity and held at 4° C. After incubation, the antibody solution was removed and the tubes were washed twice with wash buffer. The tubes were then blocked with 0.4 ml of superblock-TWEEN20 for 1 hr at 37° C. After incubation, the superblock was removed and the tubes were dried by placing them in a dry chamber for 2 hours at room temperature. Following this step, the tubes were sealed and stored at 4° C. in a humidity-free plastic container until use. The coated tubes were useable for 6 months with minimal loss in test performance Sample Collection.

Cows were bred to a synchronized heat using an OvSynch synchronization protocol. Approximately 200 cows were used for each synchronized breeding. A total of 815 cows were bred by artificial insemination (AI) and the day of AI was day 0. Blood sample from 800 cows were collected in tubes with anticoagulant K3EDTA (BD #366643) from cows on days 26 and 28 and shipped to laboratory in ice by overnight shipment. The blood samples were used directly in the color test upon receipt. The cows were checked for pregnancy status by ultrasound on day ~29 and re-confirmed by rectal palpation on day ~60. Pregnancy diagnosis data of 797 cows were available at the end of the study was used for analysis of test accuracy.

Color Test Procedure:

The blood samples were mixed by inversion up to 10 times to facilitate easy sample transfer. Four hundred microliters (0.4 ml) of blood was transferred to each tube and the tubes were incubated in a 37° C. water bath for 15 min. After this incubation, the blood sample was aspirated and the tubes were filled with wash buffer (1×PBS with 0.05% Tween20). The wash buffer was aspirated and the tubes were washed an additional 2 times with wash buffer. After the third wash, 0.4 ml of 1:2000 diluted biotin-labeled anti-PAG polyclonal antibody in dilution buffer (10% SuperblockT20™ in wash buffer) was added to each tube and incubated for 15 min at 37° C. in a water bath. Following the incubation, the tubes were aspirated and washed twice with wash buffer. Next, 0.4 ml of streptavidin-PolyHRP20 (1:30,000) in dilution buffer was added to each tube and incubated for 15 min at 37° C. in a water bath. After the third incubation, the content of each tube was aspirated and the tube was washed twice with wash buffer. Next, 0.4 ml of the HRP substrate, SureBlueReserve™, was added and incubated at room temperature for 15 min. Following incubation, a deep blue color was observed in tubes that received samples from pregnant cows (FIG. 10). Tubes that received samples from non-pregnant animals remained clear (FIG. 10). The color can be visually read to infer pregnancy status. However, to quantitate color in the laboratory, an equal volume of (0.4 ml) of stop solution (1N HCl) was added to each tube turning the blue color yellow. An aliquot (0.2 ml) from each sample was then transferred to ELISA plate and optical density was recorded at 430 nm. OD values above or equal to 0.2 were considered 'pregnant' and values below were considered 'open'. The color intensity cut off of 0.2 OD was previously established with plasma test panel samples was used for pregnancy diagnosis.

The following is a brief summary of the steps for the tube test procedure:
1. Add 400 µl of sample, 15 min at 37° C.
2. Wash 3× for blood, 2× for plasma
3. Add 400 µl of Biotin label, 15 min at 37° C.
4. Wash 2×
5. Add 400 µl of Poly-HRP20, 15 min at 37° C.
6. Wash 2×
7. Add 400 µl of SureBlue Reserve™
8. Read—5 min-15 min (Blue=pregnant; clear=open (non-pregnant))

Definitions of Test Analysis Parameters:
Sensitivity: Ability of the blood test to identify pregnant cows as pregnant
Specificity: Ability of blood test to identify open (non-pregnant) cows as open cow
Advantages of the color test: The test supplies include a purple cap blood tube (3.0 ml with K$_2$EDTA) for blood collection, pre-coated tubes, reagents, squirt bottle, and transfer pipettes. A 37° C. incubator/waterback/block is required. Unlike plate ELISA, this test does not require centrifuge for separating plasma since whole blood can be used directly in the test. The test also does not require equipments like plate shaker, equipment for washing (plate washer) or reading (plate reader). The washing can be accomplished with squirt bottles and transfer pipettes are used for the removal of wash buffer solution between washes. The color can be visually read. However, in the laboratory, at the end of the color test (after step 8), 0.4 ml of stop solution 1N HCl is added to all tubes and an aliquot (0.2 ml) is transferred to an ELISA plate and color intensity is recorded in a plate reader. The total assay time is approximately 2 hours compared to conventional plate ELISA (4 hours). This color assay can be optionally multiplexed, such as with 96-well, 48-well or 24-well plates.

Results.

Figure 11A:
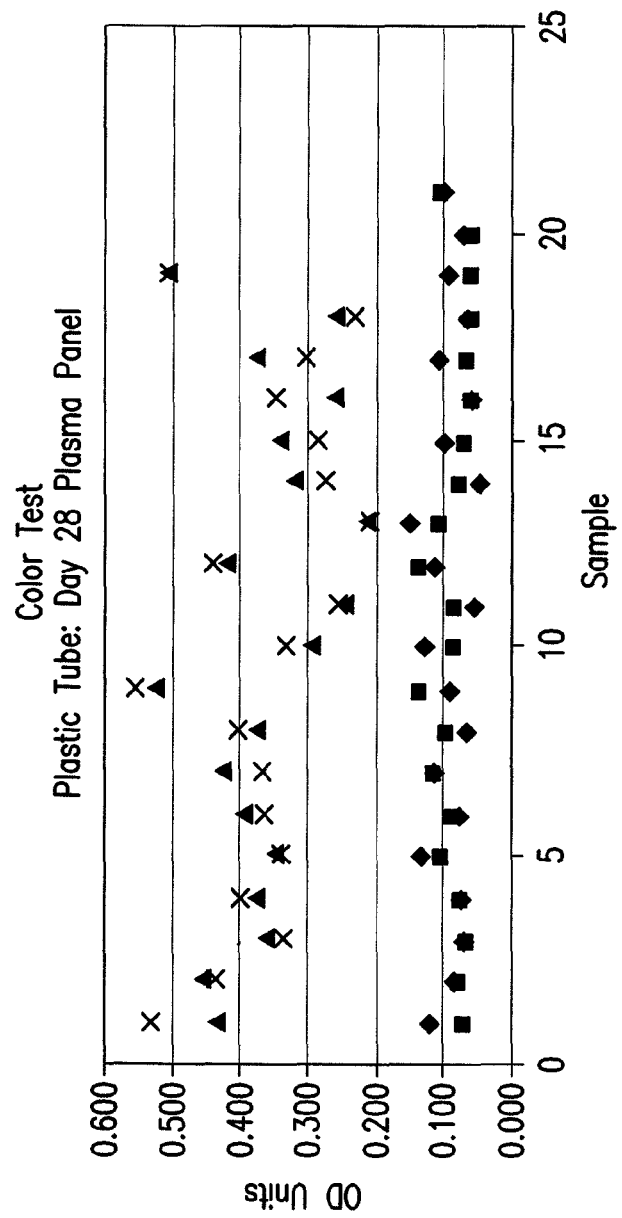
FIG. 11A, 11B. Results of color test performed with 2D9-coated plastic tubes.
Figure 11B:
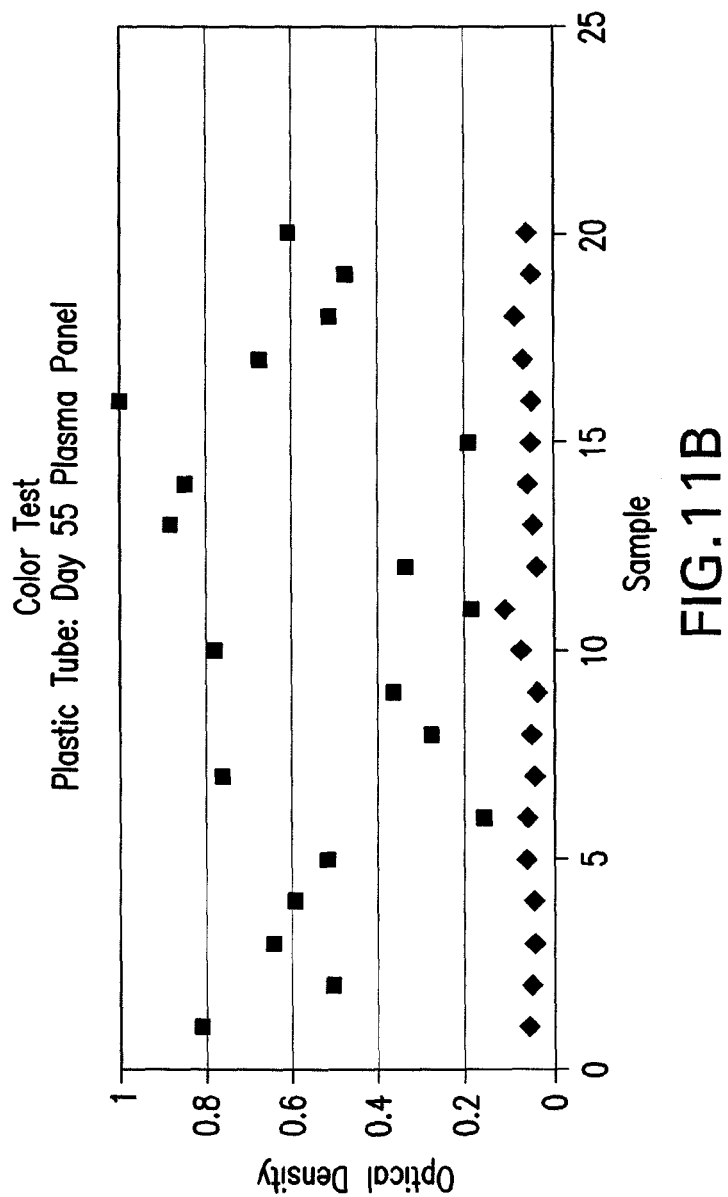

Results of the color test with day 28 plasma test panel (20 open and 20 pregnant samples) are shown in FIG. 11A, and results of the test with day 55 plasma test panel (20 open and 20 pregnant samples) are shown in FIG. 11B. All open samples have color intensity value≦0.2 OD while pregnant samples showed color intensity>0.2 OD.

By using this cut-off value, both test panels (FIGS. 11A and 11B) showed >95% sensitivity and specificity. A set fresh plasma samples were also tested in this system and shown to provide a clear separation of open cows and pregnant cows (FIG. 12).

Example 7

On-Farm Test Concepts: Bovine Color Pregnancy Test (Plastic Tubes)

Figure 13:
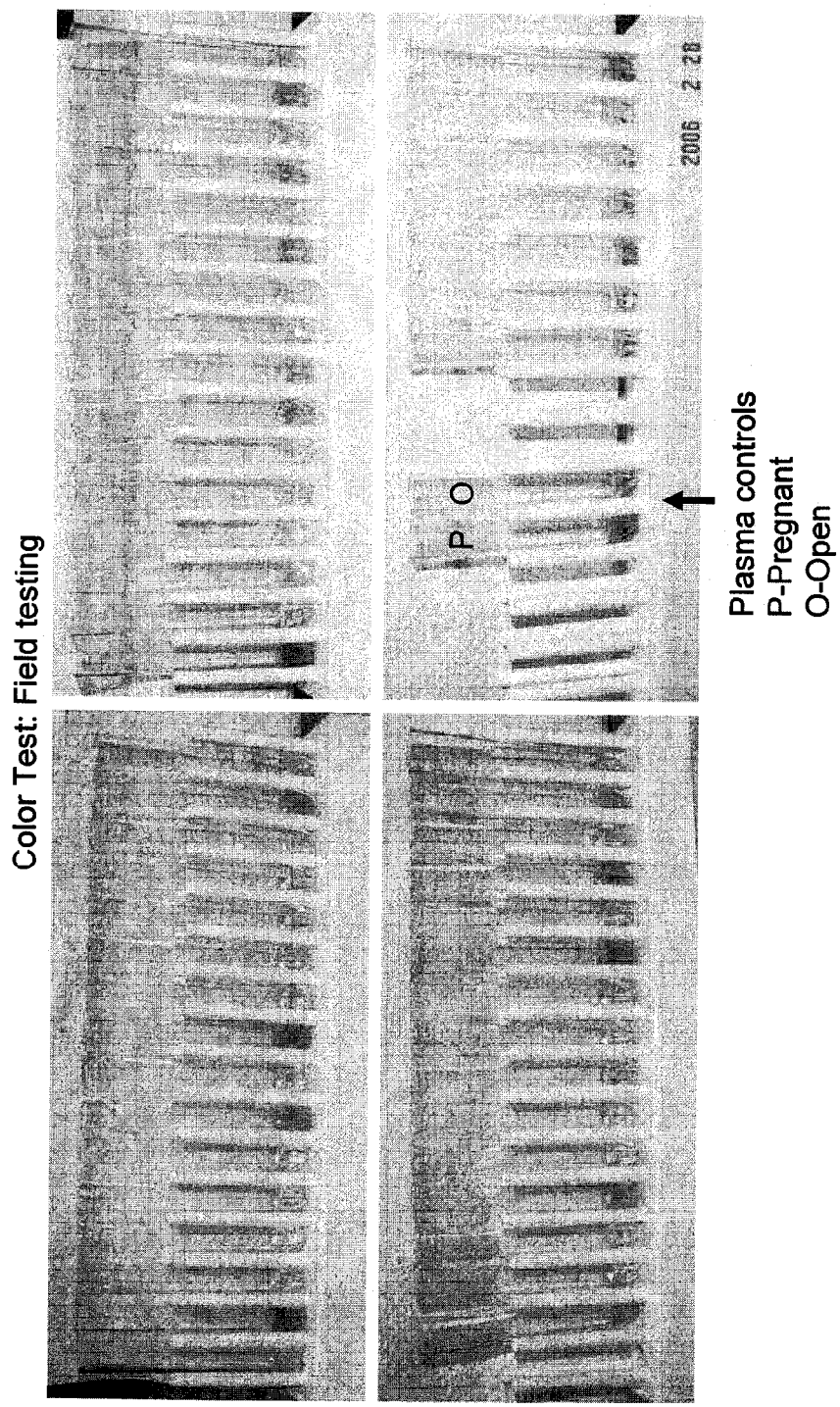
FIG. 13. Field testing of color test with blood samples. Fifty four blood samples collected from days 33-34 after breeding were tested and the color was visually read by 3 personnel. There was no disagreement observed in visual scoring of results among 3 individuals.

The test was performed 'on-farm' as described by using a 37° C. water bath and no additional equipment. In this field test, 58 blood samples were tested. Color test was performed with 0.4 ml of blood samples (FIG. 13) and pregnancy confirmation was accomplished by ultrasound (FIG. 14). The color was read by 3 personnel and there was no disagreement in visual scoring of test results. The color test was able to identify all 14 pregnant cows. All 3 individuals scored 'inconclusive' with 2 samples due to blue background and the samples were found to be 'open'. This field testing showed 100% sensitivity and 92.5% specificity (37/40) compared to ultrasound.

Example 8

Sandwich Immunoassay-Based Color Pregnancy Test (Plastic Tubes)

Materials and Methods.

A sandwich immunoassay based test was developed by using PAG monoclonal antibody, 2D9 as a capture antibody and biotin-labeled rabbit polyclonal antibody as second antibody. The PAG monoclonal antibody is coated inside of a transparent plastic tube or well and serves as a trap. The tubes used were internally ribbed tubes to increase surface area for antibody coating (Evergreen Scientific, Los Angeles, Calif.). The complex is detected with streptavidin-HRP (horseradish peroxidase)/HRP substrate system. Streptavidin Poly-HRP20 was obtained from Research Diagnostics Inc., Concord, Mass., and Horseradish Peroxidase was obtained from KPL, Inc., Gaithersburg, Md. Detection of the complex is indicated by a color (blue or yellow) in the tube or well, indicating the presence of PAGs in the sample. Information regarding the general establishment of an ELISA for the detection of PAGs in the serum of pregnant cows and heifers can be found in Green et al., 2005. The assay standard was 0.5 ng to 6.0 ng. The test takes about 4 hours to complete.

The test can be performed with simple laboratory supplies on a farm or comparable site. In this example, a 37° C. incubator and pipettes are the only components required beside reagent supplies. The color test concept can be combined with Ovsynch, Resynch and Timed Artificial Insemination (TAI) as part of a reproductive management tool for cattle. The test concept can also be extended to other analytes such as progesterone and other pregnancy antigens to increase the accuracy of diagnosis or to advance detection of pregnancy prior to day 26. Multiplexing can be performed by using, for example, 96-well or 48-well trays or by using multiple tubes.

TABLE 2

Assay reagents, supplies and supplier information.

| Item | Assay Reagent/Supplies | Purpose | Supplier Information |
|---|---|---|---|
| 1 | 2D9 Monoclonal antibody | Coating antibody | |
| 2 | Rabbit polyclonal antibody | Biotin-labeled second antibody | |
| 3 | Streptavidin-Poly Horseradish Peroxidase (HRP) 20 | Signal amplification | Research Diagnostics Inc., Concord, MA |
| 4 | Sure Blue Reserve ™ | Color substrate for HRP | KPL Inc, Gaithersburg, MD |
| 5 | Super Block | Used in blocking buffer, wash buffer and dilution buffer. | Pierce Biotechnology Inc., Rockford, IL |
| 6 | Internally ribbed tubes, 12 × 75 mm tube, polystyrene with 6 bottom ribs. | Tube used for the test | Evergreen Scientific, Los Angeles, CA |
| 7 | Phosphate Buffered Saline | Buffer medium for coating, blocking, washing & dilution of biotin-IgG, HRP reagents. | Roche |
| 8 | Biotin labeling kit (5 reactions) and Dialysis kit, Slide-A-Lyzer ™ | Preparation of biotin-labeled IgG | Roche |
| 9 | Tween 20 | Detergent used in buffer for coating, blocking, washing & dilution of biotin-IgG, HRP reagents at 0.05% conc. | Sigma Aldrich, St. Louis, MO. |
| 10 | Sodium Carbonate | Antibody coating buffer | Sigma Aldrich, St. Louis, MO. |

Results.

Pregnancy testing of 797 blood samples collected from day 26 and day 28 animals were evaluated for sensitivity and specificity by comparing to day 29 ultrasound and day 60 rectal palpation results. Plasma samples were obtained. A cut-off of 0.2 OD units for pregnancy diagnosis. Table 3 shows the accuracy of blood test compared to day 29 ultrasound based pregnancy diagnosis and day 60 rectal palpation.

TABLE 3

Analysis of blood test accuracy compared to day 29 ultrasound (US) and day 60 rectal palpation.

| | Day of blood test | | | |
|---|---|---|---|---|
| | Day 26 | | Day 28 | |
| | Number of cows tested | | | |
| | 357 | 357 | 797 | 797 |
| Pregnancy check | Day 29 US | Day 60 Palpation | Day 29 US | Day 60 Palpation |
| Sensitivity | 97.4% | 97.5% | 99.3% | 99.3% |
| Specificity | 90.1% | 91.2% | 90.9% | 91.2% |

These results show that a bovine pregnancy test developed with PAG monoclonal antibody, 2D9, provides commercially acceptable accuracy with low false-negative results. This antibody can be applied in developing rapid test formats for detecting pregnancy status of cows as early as day 26 after breeding with high sensitivity and specificity. Further analysis showed that the test accuracy can be improved to 99% sensitivity and 94% specificity by adjusting cut-off value to 0.35 OD units.

Example 9

Isolation of a Sub-Group of Early PAG Proteins Suitable for Developing a Bovine Pregnancy Test Tissue Collection.

Fetal cotyledon tissue was collected from early pregnant bovines 50 to 60 days after insemination. Fifty to sixty days of pregnancy is a preferred period in gestation because the sub-group of early PAG proteins represents a high percentage of the total PAG proteins at or about this stage of gestation. But while the percentage of the desirable, early PAG protein is high at or about 50 to 60 days after insemination, total protein and the amount of available tissue is small. At or about 61 to 250 days after insemination, total PAG protein and the quantity of fetal cotyledon and caruncle tissue is much greater.

Methods which May be Undertaken to Identify the Proteins Binding to 2D9 and to Map the Binding Sites of PAG to 2D9.

There are four approaches which may be taken in order to identify the proteins binding to 2D9, to characterize and sequence the 2D9 antibody, and to map the binding sites of PAG to 2D9. The following study was conducted:

1. Immunoprecipitation of PAGs (Obtained from Day 55 Placenta) with 2D9-Coated Magnetic Beads.

Purified 2D9 were coupled to Tosyl-activated Dynal magnetic beads according to manufacturer's directions (Dynal). The antibody coated magnetic beads were incubated with 100 micrograms of PAG enriched preparation for 30 min in 1×PBS and washed extensively with the same buffer. The bound proteins were eluted by using pH 3.0 acetic acid and subjected gel and Western blot analysis. Western blot was developed with rabbit anti-PAG polyclonal antibodies. The immuno-reactive protein bands were cut from SDS-PAGE and subjected to LC-MS-MS analysis after trypsin digestion.

The following method is an alternative immunoprecipitation method which may be performed:

2. Immunoprecipitation of PAGs (Obtained from Day 61 to 250 Placenta) with 2D9-Coated Magnetic Beads.

Purified 2D9 may be coupled to Tosyl-activated Dynal magnetic beads according to manufacturer's directions (Dynal). The antibody coated magnetic beads may be incubated with 100 micrograms of PAG preparation for 30 min in 1×PBS and washed extensively with the same buffer. The bound proteins may be eluted by using pH 3.0 acetic acid and subjected gel and Western blot analysis. Western blot may be developed with rabbit anti-PAG polyclonal antibodies. The immuno-reactive protein bands may then be cut from SDS-PAGE and subjected to LC-MS-MS analysis after trypsin digestion. A highly purified preparation of the sub-group of early PAG proteins (specifically PAGs 4, 6, 9, 20 and 21) may be purified using this procedure.

The following study was conducted:

3. Immuno-Affinity Chromatography of Tissue Extracts Prepared from Caruncle (Endometrium) and Cotyledonary (Placenta) Tissues from Day 55 of Bovine Pregnancy.

Briefly, purified 2D9 (10 mg) was coupled to 1 gram of CNBr-activated sepharose according to manufacturer's directions (Sigma, St. Louis). The 2D9-affinity resin (approximately 5.0 ml) was incubated with 25 ml tissue extract at pH 7.0, overnight for binding. Next day, the resin was packed in a column and washed with 1×PBS to remove unbound materials and eluted with pH 3.0 acetic acid. The pH of the eluted material was neutralized with 1M Tris immediately after elution to pH 7.0. The eluted material was subjected gel and Western blot analysis. Western blot was developed with rabbit anti-PAG polyclonal antibodies. The protein bands 1 to 7 were cut from SDS-PAGE and subjected to LC-MS-MS analysis after trypsin digestion. The identities of peptide sequences were determined by using BLAST analysis.

The following is an alternative chromatographic procedure which may be performed:

4. Immuno-Affinity Chromatography of Tissue Extracts Prepared from Caruncle (Endometrium) and Cotyledonary (Placenta) Tissues from Day 61 to 250 of Bovine Pregnancy.

Briefly, purified 2D9 (10 mg) may be coupled to 1 gram of CNBr-activated sepharose according to manufacturer's directions (Sigma, St. Louis). The 2D9-affinity resin (approximately 5.0 ml) may be incubated with 25 ml tissue extract at pH 7.0, overnight for binding. Next day, the resin may be packed in a column and washed with 1×PBS to remove unbound materials and eluted with pH 3.0 acetic acid. The pH of the eluted material may be neutralized with 1M Tris immediately after elution to pH 7.0. The eluted material may be subjected gel and Western blot analysis. Western blot may be developed with rabbit anti-PAG polyclonal antibodies. The protein bands 1 to 7 may be cut from SDS-PAGE and subjected to LC-MS-MS analysis after trypsin digestion. The identities of peptide sequences may then be determined by using BLAST analysis. A highly purified preparation of the sub-group of early PAG proteins (specifically PAGs 4, 6, 9, 20 and 21) may be purified using this procedure.

Example 10

Identification of Additional 2D9 Binding PAGs

The MAb 2D9 was found to recognize five PAG isoforms (4, 6, 9, 20, and 21) as summarized in Example 1. These isoforms were identified by LC/MS/MS peptide sequencing of purified PAGs samples obtained from placental tissues harvested 55 days post breeding. MAb 2D9 was further utilized for purification and identification of PAGs by coupling the antibody to a CNBr-activated resin to create an immuno-affinity column PAGs present in a purified sample may be bound (recognized) by 2D9. In a similar manner, PAGs present in bovine whole blood or plasma samples in the PAGs ELISA may be bound by 2D9 and elicit a positive ELISA response, indicating pregnancy Elution of purified PAGs during the immuno-purification procedure was modified by adjusting pH from 3.0 to 2.5 with immediate neutralization to pH 7.0 during eluent collection. Visualization of purified PAGs by SDS-PAGE with purified samples was performed essentially as described above (e.g. Example 1). Similar banding patterns, with three major bands between 50 and 75 kDa were seen.

In addition to placental tissues harvested from cows 55 days post breeding, PAGs were also purified from placental tissues harvested from cows 215 days post breeding. Certain members of the PAGs protein family (isoforms) are expressed earlier in gestation than others. The set of PAGs expressed earlier in gestation are commonly referred to as early PAGs and the set of PAGs expressed later in gestation are commonly referred to as late PAGs. Placental tissues from 55 days post breeding are representative of a gestation stage expressing early PAGs, while placental tissues from 215 days post breeding are representative of a gestation stage including late PAGs expression. Visualization of purified PAGs by SDS-PAGE from day 55 and day 215 placental tissues shows the same three bands between 50 and 75 kDa for both, however the proportion (intensity) of the higher molecular weight band is greater from day 215 placental tissues.

Figure 17:
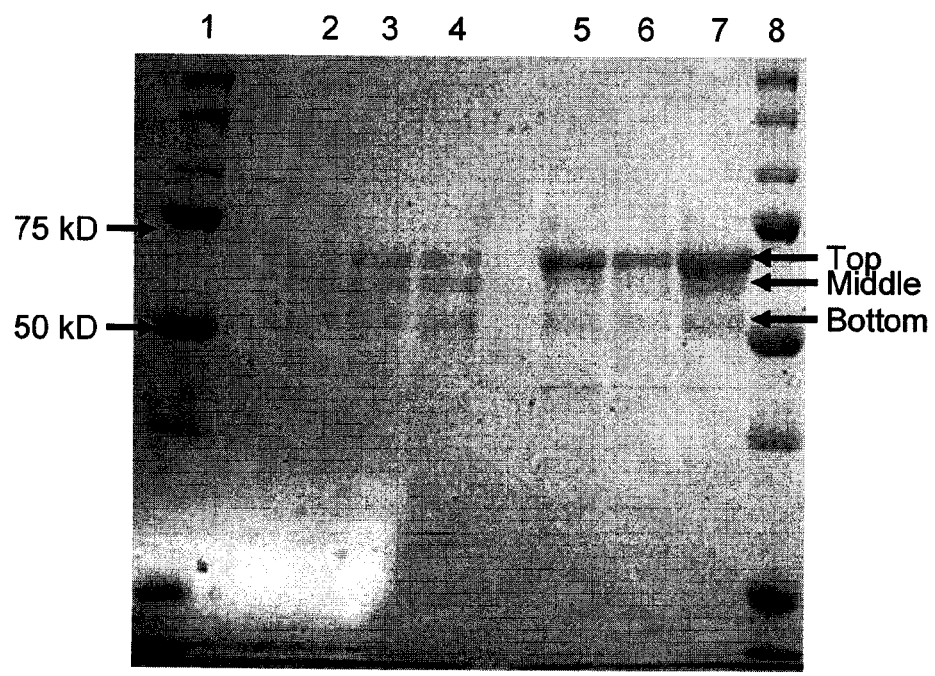
FIG. 17. SDS-PAGE gel of purified PAGs batches (5 μg each) stained with Coomassie blue illustrating the three PAGs bands (top, middle, and bottom bands) between 50 and 75 kD. 1) Protein standards (Bio-Rad Cat. #161-0374); 2) d55 caruncle; 3) d55 cotyledon; 4) d55 caruncle and cotyledon combined; 5) d215 caruncle; 6) d215 cotyledon; 7) d215 caruncle and cotyledon combined; 8) Protein standards (Bio-Rad Cat. #161-0374).

Peptides from PAGs samples from both day 55 and day 215 placental tissues were purified with a 2D9 immunoaffinity column and analyzed by LC/MS/MS peptide sequencing to identify the PAG isoform(s) present in the samples. Peptide sequences were compared with PAG isoform sequences obtained from UniProt database (www.uniprot.org) as listed in Table 4. Table 5 shows a summary of the peptide sequence results and their identification as PAGs corresponding to boPAG-16, boPAG-17, and boPAG-19 sequences by BLAST analysis. "Lanes" and "bands" (bottom, middle) referred to in Table 5 are shown in FIG. 17. A summary of the PAG isoforms characterized in the purified PAGs samples is shown in Table 6.

TABLE 4

PAG isoforms with UniProt accession numbers (SEQ ID NOs: 51-62).

| PAG isoform | Accession number |
| --- | --- |
| 1 | Q29432 |
| 4 | O46492 |
| 6 | O46494, A5PJW4 |
| 9 | O46497, A4FV16 |
| 16 | Q9TTV8 |
| 17 | Q9TTV7, A7MBA4 |
| 19 | Q9TTV5 |
| 20 | Q9TTV4 |
| 21 | Q9TTV3 |

TABLE 5

Summary of peptide sequence results (including SEQ ID NOs: 63-74).

| MH+ | Charge | Start | End | P (pep) | Peptide sequence |
|---|---|---|---|---|---|
| colspan=6 | Protein Band No.: Present in Bands Lane 2 (bottom), Lane 3 (middle), Lane 6 (middle), Lane 7 (middle and bottom) *Bos Taurus* (gi75074836) Pregnancy-associated glycoprotein 16 | | | | |
| 1389.65796 | 2 | 215 | 229 | 2.54E−05 | REGSVVMFGGVDHRY (SEQ ID NO: 63) |
| 1046.53052 | 2 | 361 | 370 | 6.28E−04 | RLYFSVFDRG (SEQ ID NO: 64) |
| 1770.90613 | 2 | 197 | 212 | 7.51E−06 | NQGAISDPIFAFYLSK (SEQ ID NO: 65) |
| colspan=6 | Protein Band No.: Present in Bands Lane 2 (bottom), Lane 3 (bottom), Lane 4 (bottom), Lane 5 (bottom), Lane 6 (bottom), Lane 7 (bottom) *Bos Taurus* (gi75074835) Pregnancy-associated glycoprotein 17 | | | | |
| 1389.65796 | 2 | 215 | 229 | 2.54E−05 | REGSVVMFGGVDHRY (SEQ ID NO: 66) |
| 1035.58337 | 2 | 138 | 148 | 1.69E−05 | KGLLVYDTVRI (SEQ ID NO: 67) |
| 1046.53052 | 2 | 361 | 370 | 6.28E−04 | RLYFSVFDRG (SEQ ID NO: 68) |
| 1771.89014 | 2 | 196 | 213 | 7.53E−07 | KNEGAISEPVFAFYLSKD (SEQ ID NO: 69) |
| colspan=6 | Protein Band No.: Present in Bands Lane 3 (middle), Lane 4 (middle), Lane 5 (middle), Lane 6 (middle) *Bos Taurus* (gi75051662) Pregnancy-associated glycoprotein 19 | | | | |
| 1760.83850 | 3 | 212 | 229 | 1.00E−06 | KDKQEGSVVMFGGVDHRY (SEQ ID NO: 70) |
| 1088.53711 | 2 | 126 | 137 | 4.36E−06 | KTFSITYGSGRI (SEQ ID NO: 71) |
| 2243.06616 | 3 | 213 | 231 | 1.32E−03 | DKQEGSVVMFGGVDHRYYR (SEQ ID NO: 72) |
| 1046.53052 | 2 | 361 | 370 | 9.55E−04 | RLYFSVFDRG (SEQ ID NO: 73) |
| 1770.90613 | 2 | 196 | 213 | 6.03E−09 | KNQGAISEPVFAFYLSKD (SEQ ID NO: 74) |

"MH+" = peptide mass to charge plus water;
"Charge" = ion charge state;
"P (pep)" = probability of peptide sequence;
"Start" = start amino acid of protein that peptide aligns with;
"End" = stop amino acid of protein that peptide aligns with.

TABLE 6

PAG isoforms characterized in Day 55 and Day 215 placental tissues.

| Day 55 Tissue Type | PAG Isoforms | Day 215 Tissue Type | PAG Isoforms |
|---|---|---|---|
| caruncle | 4, 6, 9, 16, 17, 21 | caruncle | 4, 6, 9, 17, 19, 21 |
| cotyledon | 4, 6, 9, 16, 17, 19, 21 | cotyledon | 4, 6, 9, 16, 17, 19, 21 |
| caruncle/cotyledon | 4, 6, 9, 17, 19 | caruncle/cotyledon | 4, 6, 9, 16, 17, 21 |

Figure 15:
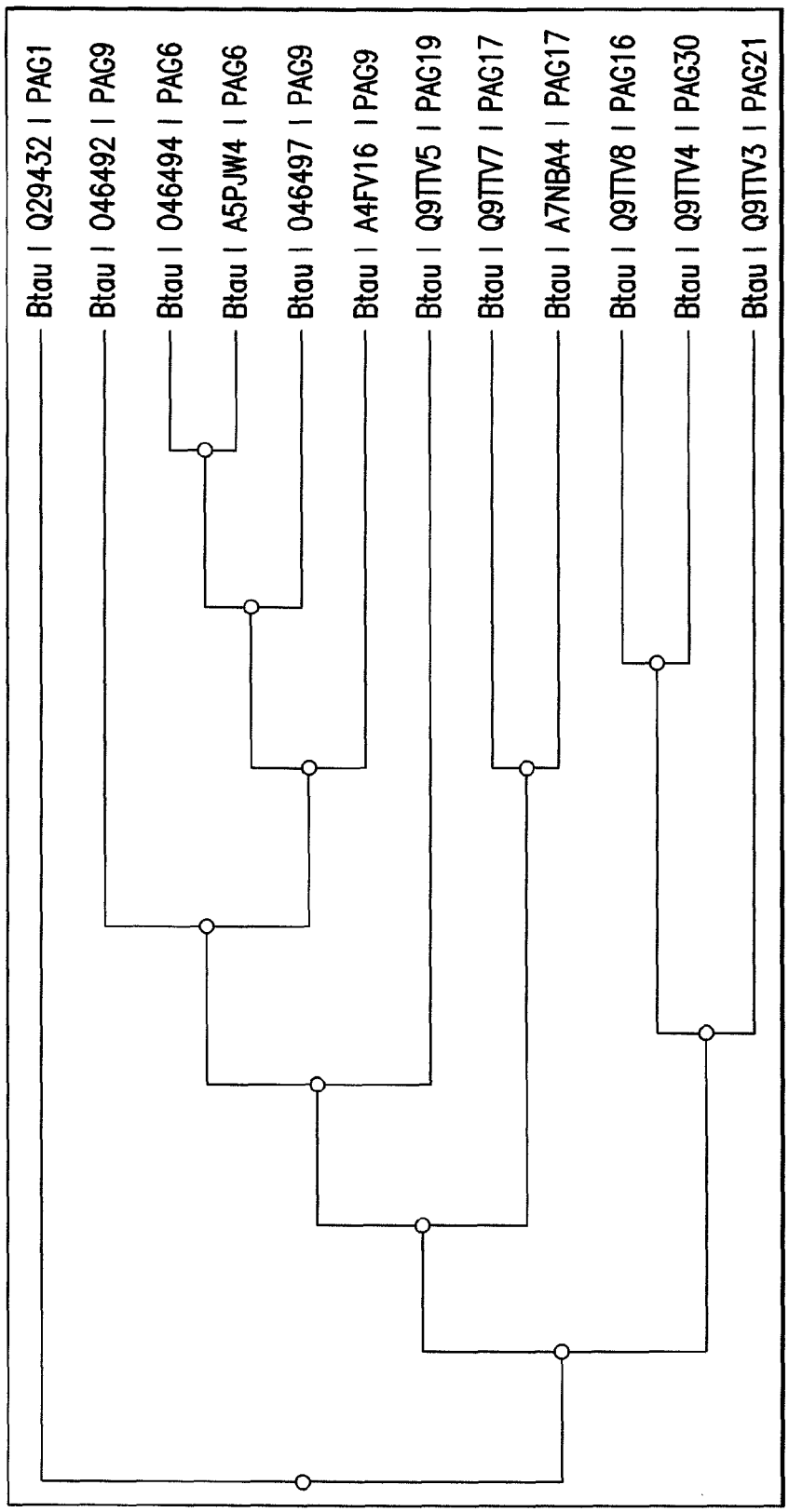
FIG. 15. PAG isoform protein sequence clusters generated by the Neighbors Phylogenetic Tree analysis package of PROTDIST (v. 3.5c), within BioEdit (v. 7.0.5.3; www.mbio.ncsu.edu/BioEdit/BioEdit.html; Hall, 1999).

Polypeptide sequences shown in Table 4 were aligned using PROTDIST v. 3.5c, e.g. from the PHYLIP package (Felsenstein, 1989). The Neighbor Phylogenetic Tree analysis package of PROTDIST was used on the aligned sequences to generate the tree shown in FIG. 15. Alignments of the PAGs are shown in FIG. 16. This analysis of PAG isoforms 1, 4, 6, 9, 16, 17, 19, 20, and 21 was performed to visualize the relatedness of the isoforms based on their regions of similarity and difference. According to the analysis, PAGs 4, 6, 9, 16, 17, 19, 20, and 21 cluster together, apart from PAG1.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 3,646,346
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,367,110
U.S. Pat. No. 4,376,110
U.S. Pat. No. 4,452,901
U.S. Pat. No. 4,668,621
U.S. Pat. No. 4,699,880
U.S. Pat. No. 5,721,105
U.S. Pat. No. 6,869,770
U.S. Patent Publn. 2003/508381
U.S. Patent Pubn. 20050100975
Abbondanzo et al., *Breast Cancer Res. Treat.*, 16:182(151), 1990.
Allred et al., *Breast Cancer Res. Treat.*, 16:182(149), 1990.
Atkinson et al., *J. Biol. Chem.*, 268(35):26679-26685, 1993.
Ausubel et al., In: *Current Protocols in Molecular Biology*, John, Wiley & Sons, Inc, NY, 1994; 1992.
Beal et al., *J. Anim. Sci.*, 70:924-929, 1992.
Biocomputing: Informatics and Genome Projects, Smith (Ed.), Academic Press, NY, 1993.

Boulianne et al., *Nature*, 312:643-646, 1984.
Brown et al., *Breast Cancer Res. Treat.*, 16: 192(#191), 1990.
Butler et al., *Biol. Reprod.*, 26:925-933, 1982.
Cabilly et al., *Proc. Natl. Acad. Sci. USA*, 91:3273-3277, 1984.
Cameron and Malmo, *Austr. Vet. J.*, 70:109-111, 1993.
Capaldi et al., *Biochem. Biophys. Res. Comm.*, 76:425, 1977.
Chardes et al., *FEBS Lett.*, 452(3):386-394, 1999.
Colligan et al., In: *Current Protocols in Immunology*, Greene Publ. Assoc. Wiley Interscien, NY, 1993.
Computational Molecular Biology, Lesk (Ed.), Oxford University Press, NY, 1988.
Computer Analysis of Sequence Data, Part I, Griffin and Griffin (Eds.), Humana Press, NJ, 1994.
Cumber et al., *J. Immunology*, 149B:120-126, 1992.
Engvall, *Lancet*, 2(8000):1410, 1976.
Engvall, *Med Biol.*, 55(4):193-200, 1977.
Engvall, *Methods Enzymol*, 70(A):419-39, 1980.
Felsenstein, *Cladistics* 5:164-166, 1989.
Green et al., *Theriogenology*, 63(5):1481-1503, 2005.
Green et al., *Biol Reprod* 62:1624-1631, 2000.
Green et al., *Biol Reprod* 60:1069-1077, 1999.
Gripenberg et al., *Scand J Immunol.*, 7(2):151-7, 1978.
Guruprasad et al. *Protein Eng* 9:849-856, 1996.
Hall, *Nucl. Acids. Symp. Ser.* 41:95-98, 1999.
Harlow and Lane, In: *Antibodies, a Laboratory Manual*, Cold Spring Harbor Laboratory, pp 139-281, 1988.
Hatzidakis et al., *J. Reprod. Fertil.*, 98:235-240, 1993.
Higgins and Sharp CABIOS. 5:151-153 (1989
Holdsworth et al., *J. Endocrin.*, 95:7-12, 1982.
Hughes et al., *Mol Biol Evol.* 20:1940-1945, 2003.
Humblot et al., *Theriogenol.*, 30:257-268, 1988.
Kiracofe et al., *J. Anim. Sci.*, 71:2199-2205, 1993.
Kohler and Milstein, *Nature*, 256:495-497, 1975.
Leibiger et al., *Biochem J.*, 338:529-538, 1999.
Liu et al. *Cell Mol. Biol.*, 49(2):209-216, 2003.
Makler et al., *Transfusion*, 21(3):303-312, 1981.
Markusfeld et al., *Br. Vet. J.*, 146: 504-508, 1990.
Mialon et al., *Reprod. Nutr. Dev.*, 33:269-282, 1993.
Mialon et al., *Reprod. Nutr. Dev.*, 34:65-72, 1994.
Mo et al., *Eur. J. Immunol.*, 23:2503-2510, 1993.
Nakamura et al., In: *Handbook of Experimental Immunology* ($4^{th}$ Ed.), Weir et al. (Eds.), 1:27, Blackwell Scientific Publ., Oxford, 1987.
Neuberger et al., *Nature*, 314:268-270, 1985.
Oltenacu et al., *J. Dairy Sci.*, 73:2826-2831, 1990.
Pack et al., *Biochem.*, 31:1579-1584, 1992.
PCT Appln. WO 98/16832
Sarngadharan et al., *Princess Takamatsu Symp.*, 15:301-8, 1984.
Sasser et al., *Biol. Reprod.*, 35:936-942, 1986.
Sequence Analysis in Molecular Biology, von Heinje (Ed.), Academic Press, 1987.
Sequence Analysis Primer, Gribskov and Devereux (Eds.), Stockton Press, NY, 1991.
Szafranska et al., *Biol. Reprod.*, 53:21-28, 1995.
Wagner et al., *Science*, 260(5113):1510-1513, 1993
Warnick et al., *Theriogenol.*, 44:811-825, 1995.
Xie et al., *Biol. Reprod.*, 51:1145-1153, 1994.
Xie et al., *Biol. Reprod.*, 54: 122-129, 1996.
Xie et al., *Biol. Reprod.*, 57:1384-1393, 1997.
Xie et al., *Proc. Natl. Acad. Sci. USA*, 88:10247-10251, 1991.
Xie et al., *Proc. Natl. Acad. Sci. USA*, 94:12809-12816, 1997.
Zoli et al., *Biol. Reprod.*, 45:1-10, 1991.
Zoli et al., *Biol. Reprod.*, 46:83-92, 1992.

What is claimed is:

1. An antibody produced by a hybridoma deposited as ATCC Accession Number PTA-8566, or an antigen-binding fragment thereof.

2. An isolated cell deposited under ATCC Accession Number PTA-8566, or a progeny cell thereof that produces antibody 2D9.

3. An isolated polynucleotide that encodes an antibody heavy or light chain domain, wherein the heavy or light chain domain is selected from the group consisting of:
   a) a polypeptide sequence comprising SEQ ID NO:1; and
   b) a polypeptide sequence comprising SEQ ID NO:2,
      wherein an antibody comprising said heavy or light chain binds immunologically to pregnancy associated glycoproteins (PAGs) PAG4, PAG6, PAG9, PAG16, PAG17, PAG19, PAG20 and PAG21.

4. The polynucleotide of claim 3, wherein the domain comprises SEQ ID NO:1.

5. The polynucleotide of claim 3, wherein the domain comprises SEQ ID NO:2.

6. The polynucleotide of claim 3, wherein the polynucleotide is further defined as encoding the polypeptide sequence of SEQ ID NO:3.

7. The polynucleotide of claim 3, wherein the polynucleotide is further defined as encoding the polypeptide sequence of SEQ ID NO:4.

8. The polynucleotide of claim 3, wherein the polynucleotide comprises SEQ ID NO:5.

9. The polynucleotide of claim 3, wherein the polynucleotide comprises SEQ ID NO:6.

10. An isolated polypeptide comprising an antibody heavy or light chain domain, wherein the heavy or light chain domain is selected from the group consisting of:
    a) a polypeptide sequence comprising SEQ ID NO:1; and
    a polypeptide sequence comprising SEQ ID NO:2,
       wherein an antibody comprising said heavy or light chain binds immunologically to PAG4, PAG6, PAG9, PAG16, PAG17, PAG19, PAG20 and PAG21.

11. The polypeptide of claim 10, wherein the polypeptide binds immunologically to at least a first PAG selected from the group consisting of PAG4, PAG6, PAG9, PAG16, PAG17, PAG19, PAG20, and PAG21.

12. An antibody or fragment thereof comprising the polypeptide of claim 10.

13. A method for detecting pregnancy in a bovine animal comprising:
   a) obtaining a sample from a bovine animal;
   b) contacting the sample with an antibody or fragment thereof according to claim 1, wherein the antibody is monoclonal antibody is 2D9 or a fragment thereof; and
   c) determining whether the sample contains at least a first pregnancy associated antigen (PAG) that is capable of being bound immunologically by the antibody or fragment thereof, wherein the presence of the PAG in the sample is indicative of pregnancy.

14. The method of claim 13, wherein determining whether the sample contains at least a first pregnancy associated antigen comprises ELISA, or Western blotting.

15. The method of claim 14, wherein the ELISA is a sandwich ELISA comprising binding of a PAG to the antibody or fragment thereof fixed to a substrate and a second antibody preparation labeled with an enzyme.

16. The method of claim 15, wherein said enzyme is alkaline phosphatase or horseradish peroxidase.

17. A kit comprising:
   (a) an antibody or fragment thereof according to claim 12; and
   (b) a container for the antibody or fragment thereof.

18. The kit of claim 17, further defined as containing means for detecting immunological binding between the antibody or fragment thereof and at least a first pregnancy associated antigen (PAG).

19. The kit of claim 17, wherein the antibody or fragment thereof is attached to a support.

20. The kit of claim 19, wherein said support is a polystyrene plate, test tube or dipstick.

21. The kit of claim 17, further comprising a detectable label.

22. The kit of claim 17, wherein the detectable label is a fluorescent or chemiluminescent tag.

23. The kit of claim 17, wherein the detectable label is an enzyme.

24. The kit of claim 23, wherein the enzyme is alkaline phosphatase or horseradish peroxidase.

25. A method of purifying at least a first pregnancy associated antigen (PAG), comprising:
   a) obtaining a sample comprising at least a first pregnancy associated antigen (PAG); and
   b) purifying the PAG relative to the sample based on the affinity of the PAG for the antibody or fragment thereof of claim 12.

26. The method of claim 25, wherein the sample is obtained from day 50 to 250 bovine placenta.

27. The method of claim 26, wherein the sample is obtained from day 61 to 250 bovine placenta.

28. The method of claim 25, wherein purifying comprises immunoprecipitation, western blot, or immuno-affinity chromatography.

* * * * *

UNITED STATES PATENT AND TRADEMARK OFFICE
CERTIFICATE OF CORRECTION

| | | |
|---|---|---|
| PATENT NO. | : 8,431,349 B2 | Page 1 of 1 |
| APPLICATION NO. | : 12/747514 | |
| DATED | : April 30, 2013 | |
| INVENTOR(S) | : Mathialagan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 16 days.

Signed and Sealed this
Sixth Day of January, 2015

Michelle K. Lee
*Deputy Director of the United States Patent and Trademark Office*